US006022708A

United States Patent [19]
de Sauvage et al.

[11] Patent Number: 6,022,708
[45] Date of Patent: Feb. 8, 2000

[54] FUSED

[75] Inventors: Frederic de Sauvage, Foster City; Arnon Rosenthal, Burlingame, both of Calif.

[73] Assignee: Genentech, Inc., South San Francisco, Calif.

[21] Appl. No.: 09/031,563

[22] Filed: Feb. 26, 1998

[51] Int. Cl.[7] .............................. C12P 21/02; C12N 1/21; C12N 5/10; C12N 15/63

[52] U.S. Cl. ................ 435/69.1; 435/252.3; 435/252.33; 435/254.2; 435/254.21; 435/320.1; 435/325; 435/358; 536/23.5

[58] Field of Search ................................ 435/69.1, 70.1, 435/70.3, 71.1, 71.2, 252.3, 252.33, 254.11, 254.2, 254.21, 320.1, 325, 358; 536/23.1, 23.2, 23.5

[56] References Cited

U.S. PATENT DOCUMENTS

| 5,602,171 | 2/1997 | Tang et al. | 514/455 |
| 5,710,173 | 1/1998 | Tang et al. | 514/447 |

FOREIGN PATENT DOCUMENTS

WO 96/35124 11/1996 WIPO.
WO 96/40276 12/1996 WIPO.

OTHER PUBLICATIONS

Akimaru et al., "Drosophila CBP is a co–activator of cubitus interruptus in hedgehog signalling" *Nature* 386:735–738 (Apr. 17, 1997).

Alcedo et al., "The Drosophila smoothened Gene Encodes a Seven–Pass Membrane Protein, a Putative Receptor for the Hedgehog Signal" *Cell* 86:221–232 (1996).

Alexandre et al., "Transcriptional activation of hedgehog target genes in Drosophila is mediated directly by the cubitus interruptus protein, a member of the GLI family of zinc finger DNA–binding proteins" *Genes & Development* 10(16):2003–2013 (Aug. 15, 1996).

Apelqvist et al., "Sonic hedgehog directs specialised mesoderm differentiation in the intestine and pancreas" *Current Biology* 7(10):801–804 (Oct. 1, 1997).

Bellusci et al., "Involvement of Sonic hedgehog (Shh) in mouse embryonic lung growth and morphogenesis" *Development* 124(1):53–63 (Jan. 1977).

Bitgood et al., "Hedgehog and Bmp genes are coexpressed at many diverse sites of cell–cell interaction in the mouse embryo" *Developmental Biology* 172(1):126–138 (Nov. 1995).

Bitgood et al., "Sertoli Cell Signaling by Desert Hedgehog Regulates the Male Germline" *Current Biology* 6(3):298–304 (1996).

Busson et al., "Genetic analysis of viable and lethal fused mutants of Drosophila melanogaster" *Roux's Archives of Developmental Biology* 197:221–230 (1988).

Chen and Struhl, "Dual roles for patched in sequestering and transducing Hedgehog" *Cell* 87(3):553–563 (Nov. 1, 1996).

Chiang et al., "Cyclopia and defective axial patterning in mice lacking Sonic hedgehog gene function" *Nature* 383(6599):407–413 (Oct. 3, 1996).

Chidambaram et al., "Mutations in the human homologue of the Drosophila patched gene in Caucasian and African–American nevoid basal cell carcinoma syndrome patients" *Cancer Research* 56(20):4599–4601 (Oct. 15, 1996).

Dominquez et al., "Sending and receiving the hedgehog signal: control by the Drosophila Gli protein Cubitus interruptus" *Science* 272(5268):1621–1625 (Jun. 14, 1996).

Echelard et al., "Sonic hedgehog, a member of a family of putative signaling molecules, is implicated in the regulation of CNS polarity" *Cell* 75:1417–1430 (1993).

Ekker et al., "Patterning activities of vertebrate hedgehog proteins in the developing eye and brain" *Current Biology* 5(8):944–955 (Aug. 1, 1995).

Ericson et al., "Sonic hedgehog induces the differentiation of ventral forebrain neurons: a common signal for ventral patterning within the neural tube" *Cell* 81(5):747–756 (Jun. 2, 1995).

Fan et al., "Patterning of mammalian somites by surface ectoderm and notochord: evidence for sclerotome induction by a hedgehog homolog" *Cell* 79(7):1175–1186 (Dec. 30, 1994).

Gailani et al., "The role of the human homologue of Drosophila patched in sporadic basal cell carcinomas" *Nature Genetics* 14:78–81 (Sep. 1996).

Hahn et al., "Mutations of the Human Homolog of Drosophila Patched in the Nevoid Basal Cell Carcinoma Syndrome" *Cell* 85:841–851 (1996).

Hammerschmidt et al., "Protein kinase A is a common negative regulator of Hedgehog signaling in the vertebrate embryo" *Genes & Development* 10(6):647–658 (Mar. 15, 1996).

Hanks et al., "Protein kinase catalytic domain sequence database: identification of conserved features of primary structure and classification of family members" *Methods in Enzymology* 200:38–62 (1991).

Hooper and Scott, "The Drosophila patched gene encodes a putative membrane protein required for segmental patterning" *Cell* 59:751–765 (1989).

Hynes et al., "Control of cell pattern in the neural tube by the zinc finger transcription factor and oncogene Gli–1" *Neuron* 19(1):15–26 (Jul. 1997).

Hynes et al., "Induction of Midbrain Dopaminergic Neurons by Sonic Hedgehog" *Neuron* 15:35–44 (1995).

Ingham et al., "Signalling by hedgehog family proteins in Drosophila and vertebrate development" *Curr. Opin. Genet. Dev.* 5:492–498 (1995).

(List continued on next page.)

*Primary Examiner*—Nancy Degen
*Assistant Examiner*—Robert Schwartzman
*Attorney, Agent, or Firm*—Craig G. Svoboda

[57] ABSTRACT

The present invention relates to nucleotide sequences, including expressed sequence tags (ESTs), oligonucleotide probes, polypeptides, vectors and host cells expressing, immunoadhesins, agonists and antagonists to human & vertebrate fused.

25 Claims, 31 Drawing Sheets

OTHER PUBLICATIONS

Jiang and Struhl, "Regulation of the Hedgehog and Wingless signalling pathways by the F box/WD40–repeat protein Slimb" *Nature* 391:493–496 (Jan. 29, 1998).

Johnson et al., "Ectopic expression of Sonic hedgehog alters dorsal–ventral patterning of somites" *Cell* 79:1165–1173 (1994).

Johnson et al., "Human Homolog of Patched, a Candidate Gene for the Basal Cell Nevus Syndrome" *Science* 272:1668–1671 (1996).

Krauss et al., "A functionally conserved homolog of the Drosophila segment polarity gene hh is expressed in tissues with polarizing activity in zebrafish embryos" *Cell* 75:1431–1444 (1993).

Krishnan et al., "Mediation of Sonic hedgehog–induced expression of COUP-TFII by a protein phosphatase" *Science* 278(5345):1947–1950 (Dec. 12, 1997).

Laufer et al., "Sonic hedgehog and Fgf–4 act through a signaling cascade and feedback loop to integrate growth and patterning of the developing limb bud" *Cell* 79(6):993–1003 (Dec. 16, 1994).

Lee et al., "Glil is a target of Sonic hedgehog that induces ventral neural tube development" *Development* 124(13):2537–2552 (Jul. 1997).

Li et al., "A single morphogenetic field gives rise to two retina primordia under the influence of the prechordal plate" *Development* 124(3):603–615 (Feb. 1997).

Macdonald et al., "Midline signalling is required for Pax gene regulation and patterning of the eyes" *Development* 121(10):3267–3278 (Oct. 1995).

Marigo et al., "Biochemical evidence that patched is the Hedgehog receptor" *Nature* 384(6605):176–179 (Nov. 14, 1996).

Marti et al., "Requirement of 19K form of Sonic hedgehog for induction of distinct ventral cell types in CNS explants" *Nature* 375(6529):322–325 (May 25, 1995).

Nakano et al., "A protein with several possible membrane–spanning domains encoded by the Drosophila segment polarity gene patched" *Nature* 341:508–513 (1989).

Nusslein–Volhard et al., "Mutations Affecting the Pattern of the Larval Cuticle in Drosophila Melanogaster" *Roux's Archives of Developmental Biology* 193(5):267–282 (1984).

Orenic et al., "Cloning and characterization of the segment polarity gene cubitus interruptus Dominant of Drosophila" *Genes & Development* 4(6):1053–1067 (Jun. 1990).

Oro et al., "Basal cell carcinomas in mice overexpressing sonic hedgehog" *Science* 276(5313):817–821 (May 2, 1997).

Perrimon, N., "Hedgehog and Beyond" *Cell* 80:517–520 (1995).

Pham et al., "The Suppressor of fused gene encodes a novel Pest protein involved in Drosophila segment polarity establishment" *Genetics* 140(2):587–598 (Jun. 1995).

Preat, "Characterization of Suppressor of fused, a complete suppressor of the fused segment polarity gene of Drosophila melanogaster" *Genetics* 132(3):725–736 (Nov. 1992).

Preat et al., "A putative serine/threonine protein kinase encoded by the segment–polarity fused gene of Drosophila" *Nature* 347(6288):87–89 (Sep. 6, 1990).

Preat et al., "Segmental polarity in Drosophila melanogaster: genetic dissection of fused in a Suppressor of fused background reveals interaction with costal-2" *Genetics* 135(4):1047–1062 (Dec. 1993).

Riddle et al., "Sonic hedgehog mediates the polarizing activity of the ZPA" *Cell* 75:1401–1416 (1993).

Robbins et al., "Hedgehog elicits signal transduction by means of a large complex containing the kinesin–related protein costal2" *Cell* 90(2):225–234 (Jul. 25, 1997).

Roberts et al., "Sonic hedgehog is an endodermal signal inducing Bmp–4 and Hox genes during induction and regionalization of the chick hindgut" *Development* 121:3163–3174 (1995).

Roelink et al., "Floor plate and motor neuron induction by different concentrations of the amino–terminal cleavage product of sonic hedgehog autoproteolysis" *Cell* 81(3):445–455 (May 5, 1995).

Sisson et al., "Costal2, a novel kinesin–related protein in the Hedgehog signaling pathway" *Cell* 90(2):235–245 (Jul. 25, 1997).

Stone et al., "The tumour–suppressor gene patched encodes a candidate receptor for Sonic hedgehog" *Nature* 384(14):129–134 (Nov. 1996).

Therond et al., "Functional domains of fused, a serine–threonine kinase required for signaling in Drosophila" *Genetics* 142(4):1181–1198 (Apr. 1996).

Therond et al., "Phosphorylation of the fused protein kinase in response to signaling from hedgehog" *Proc. Natl. Acad. Sci. USA* 93(9):4224–4228 (Apr. 30, 1996).

Unden et al., "Mutations in the human homologue of Drosophila patched (PTCH) in basal cell carcinomas and the Gorlin syndrome: different in vivo mechanisms of PTCH inactivation" *Cancer Research* 56(20):4562–4565 (Oct. 15, 1996).

Ungar et al., "Inhibition of protein kinase A phenocopies ectopic expression of hedgehog in the CNS of wild–type and cyclops mutant embryos" *Developmental Biology* 178(1):186–191 (Aug. 25, 1996).

van den Heuvel and Ingham, "Smoothened Encodes a Receptor–Like Serpentine Protein Required for Hedgehog Signalling" *Nature* 382:547–551 (1996).

Wicking et al., "Most germ–line mutations in the nevoid basal cell carcinoma syndrome lead to a premature termination of the Patched protein, and no genotype–phenotype correlations are evident" *American Journal of Human Genetics* 60(1):21–26 (Jan. 1997).

Xie et al., "Activating Smoothened mutations in sporadic basal–cell carcinoma" *Nature* 391(6662):90–92 (Jan. 1, 1998).

Zamecnik et al., "Inhibition of replication and expression of human T–cell lymphotropic virus type III in cultured cells by exogenous synthetic oligonucleotides complementary to viral RNA" *Proc. Natl. Acad. Sci.* 83:4143–4146 (1986).

Myers (1996) Human sequence tagged site SHGC–32400. GenBank accession No. G27519. GenBank record date Jun. 28, 1996. Accessed Nov. 9, 1998.

> length: 4880 bp (circular)

```
  1 CCCGGGGATC CTCTAGAGAT CCCTTCGACCT CGACCCACGC GTCCGCCCAC GCGTCCGCCC ACGCGTCCGG GGCGTCCCAG ATGTTGTGGA ACTGTCCCTG
    GGGCCCCTAG GAGATCTCTA GGGAGCTGGA GCTGGGTGCG CAGGCGGGTG CGCAGGCGGG TGCGCAGGCC CCGCAGGGTC TACAACACCT TGACAGGGAC

101 GATCTATAGC TCTTCACCGT CTCTACTTTC TTCCTTCTAA GAGATCCTGA AACCTCTGTC ATGGAAAAGT ACCACGTGTT GGAGATGATT GGAGAAGGCT
    CTAGATATCG AGAAGTGGCA GAGATGAAAG AAGGAAGATT CTCTAGGACT TTGGAGACAG TACCTTTTCA TGGTGCACAA CCTCTACTAA CCTCTTCCGA
  1                                                                            M  E  K  Y   H  V  L   E  M  I   G  E  G  S

201 CTTTTGGGAG GGTGTACAAG GGTCGAAGAA AATACAGTGC TCAGGTCGTG GCCCTGAAGT TCATCCCAAA ATTGGGGCGC TCAGAGAAGG AGCTGAGGAA
    GAAAACCCTC CCACATGTTC CCAGCTTCTT TTATGTCACG AGTCCAGCAC CGGGACTTCA AGTAGGGTTT TAACCCCGCG AGTCTCTTCC TCGACTCCTT
 15   F  G  R   V  Y  K   G  R  R  K   Y  S  A    Q  V  V    A  L  K  F    I  P  K    L  G  R    S  E  K  E    L  R  N

301 TTTGCAACGA GAGATTGAAA TAATGCGGGG TCTGCGGCAT CCCAACATTG TGCATATGCT TGACAGCTTT GAAACTGATA AAGAGGTGGT GGTGGTGACA
    AAACGTTGCT CTCTAACTTT ATTACGCCCC AGACGCCGTA GGGTTGTAAC ACGTATACGA ACTGTCGAAA CTTTGACTAT TTCTCCACCA CCACCACTGT
 48   L  Q  R   E  I  E  I    M  R  G    L  R  H   P  N  I  V    H  M  L    D  S  F    E  T  D  K    E  V  V    V  V  T

401 GACTATGCTG AGGGAGAGCT CTTTCAGATC CTAGAAGATG ACGGAAAAACT TCCTGAAGAC CAGGTTCAGG CCATTGCTGC CCAGTGGTG TCAGCCCTGT
    CTGATACGAC TCCCTCTCGA GAAAGTCTAG GATCTTCTAC TGCCTTTTGA AGGACTTCTG GTCCAAGTCC GGTAACGACG GGTCAACAC AGTCGGGACA
 81   D  Y  A  E    G  E  L    F  Q  I    L  E  D  D    G  K  L    P  E  D    Q  V  Q  A    I  A  A    Q  L  V    S  A  L  Y

501 ACTATCTGCA TTCCCACCGC ATCCTACACC GAGATATGAA GCCTCAGAAC ATCCTCCTCG TGGCATCAAG CCAAGGGTGG CTCTGTGACT TTGGATTTGC
    TGATAGACGT AAGGGTGGCG TAGGATGTGG CTCTATACTT CGGAGTCTTG TAGGAGGAGC ACCGTAGTTC GGTTCCCACC GAGACACTGA AACCTAAACG
115   Y  L  H   S  H  R    I  L  H  R    D  M  K    P  Q  N    I  L  L  A    K  G  G    I  K    L  C  D  F    G  F  A

601 CCGGCTATG AGCACCAATA CAATGGTGCT GACATCCATC AAAGGCACAC CACTCTATAT GTCTCCAGAG CTGGTGGAGG AGCGACCTCC CGACCACACA
    GGCCGATAC TCGTGGTTAT GTTACCACGA CTGTAGGTAG TTTCCGTGTG GTGAGATATA CAGAGGTCTC CAGCCACCTCC TCGCTGGAGG GCTGGTGTGT
148   R  A  M    S  T  N  T    M  V  L    T  S  I    K  G  T  P    L  Y  M    S  P  E    L  V  E  E    R  P  Y    D  H  T

701 GCGGACCTCT GGTCTGTTGG CTGCATATA TATGAACTGG CAGTAGGCAC CCCTCCCTTC TATGCTACAA GCATCTTTCA GCTGGTCAGC CTCATTCTCA
    CGCCTGGAGA CCAGACAACC GACGTATGAT ATACTTGACC GTCATCCGTG GGGAGGGAAG ATACGATGTT CGTAGAAAGT CGACCAGTCG GAGTAAGAGT
181   A  D  L  W    S  V  G    C  I  L    Y  E  L  A    V  G  T    P  P  F    Y  A  T  S    I  F  Q    L  V  S    L  I  L  K
```

```
1701 AGAGCAACAG CCTCCAGCAG CAATCTTGTT ATGGGACCTT CTTACAGGAC CTGATGGCTG TGATTCAGGC CTACTTTGCC TGTACCTTCA ATCTGAGAG
     TCTCGTTGTC GGAGTCGTC GTTAGAACAA TACCCTGGAA GAATGTCCTG GACTACCGAC ACTAAGTCCG GATGAAACGG ACATGGAAGT TAGACCTCTC
515   S   N   S      L   Q   Q      Q   S   W   Y      L   Q   D      L   M   A   V      I   Q   A      Y   F   A      C   T   F   N      L   E   R

1801 GAGCCAGACA AGTGACAGCC TGCAGGTGTT TCAGGAGGCT GCCAACCTTT GTTGGGGAAA TTCTGGACCT GCCAAGATGA AACCAGATGA CTCTGAGCAG
     CTCGGTCTGT TCACTGTCGG ACGTCCACAA AGTCCTCCGA CGGTTGGAAA CAACCCCTTT AAGACCTGGA CGGTTCTACT TTGGTCTACT GAGACTCGTC
548   S   Q   T      S   D   S   L      Q   V   F      Q   E   A      A   N   L   F      L   D   L      L   G   K      L   L   A   Q      P   D   D      S   E   Q

1901 ACTTTGCGGA GGGACAGCCT TATGTGCTTT ACTGTCCTGT GCGAAGCCAT GGATGGGAAC AGCCGGGCCA TCTCCAAAGC CTTTTACTCC AGCTTGCTGA
     TGAAACGCCT CCCTGTCGGA ATACACGAAA TGACAGGACA CGCTTCGGTA CCTACCCTTG TCGGCCCGGT AGAGGTTTCG GAAAATGAGG TCGAACGACT
581   T   L   R   R      D   S   L      M   C   F      T   V   L   C      E   A   M      D   G   N      S   R   A   I      S   K   A      F   Y   S      S   L   L   T

2001 CGACACAGCA GGTTGTCTTG GATGGGCTCC TTCATGGCTT GACAGTTCCA CAGCTCCCTG TCGAGGGAC AGGTGTGAGG GGTTCCTCGG CCGCCACT
     GCTGTGTCGT CCAACAGAAC CTACCCGAGG AAGTACCGAA CTGTCAAGGT GTCGAGGGAC AGCTCCCTG GTCGAGGAC AGGTGTGAGG CGGTCGGTGA
615   T   Q   Q      V   V   L      D   G   L   L      H   G   L      T   V   P      Q   L   P   V      H   T   P      Q   G   A      P   Q   V   S      Q   P   L

2101 GCGAGAGCAG AGTGAGGATA TACCTGGAGC CATTTCCTCT GCCCTGGCAG TGCTCCCTGT GGACTGCCCG ACTGCTGGGA TGCCAAGGAG
     CGCTCTCGTC TCACTCCTAT ATGGACCTCG GTAAAGGAGA CGGGACCGTC ACGAGGGACA CCTGACGGGC TGACGACCCT ACGGTTCCTC
648   R   E   Q      S   E   D   I      P   G   A      I   S   S      A   L   A   A      I   C   T      A   P   V      G   L   P   D      C   W   D      A   K   E

2201 CAGGTCTGTT GGCATTTGGC AAATCAGCTA ACTGAAGACA GCAGCCAGCT CAGGCCCATC CTCATCTCTG GCCTGCACCT TCCCATCCTG TGCCTGCACC
     GTCCAGACAA CCGTAAACCG TTTAGTCGAT TGACTTCTGT CGTCGGTCGA GTCCGGTAGG GAGTAGAGAC CGGACGTGGA AGGGTAGGAC ACGGACGTGG
681   Q   V   C   W      H   L   A      N   Q   L      T   E   D   S      Q   L   R   P   S      L   I   S   G      L   Q   H      P   I   L      C   L   H   L

2301 TTCTCAAGGT TCTATACTCC TGCTGCCTTG ACGACGGAAC AGTCACTCCC GAGGTGAGG GTCTACTGAA CCCTGTGAGG ACTTCCTCTC TGTTGATTCA
     AAGAGTTCCA AGATATGAGG ACGACGGAAC TGCTGCCTTG TCAGTGAGGG CTCCACTCC CAGATGACTT GGGACACTCT TGAAGGAGAG ACAACTAAGT
715   L   K   V      L   Y   S      C   C   L   V      S   E   G      L   C   R      L   L   G   Q      E   P   L      A   L   E      S   L   F   M      L   I   Q

2401 GGGCAAGGTA AAAGTAGTAG ATTGGGAAGA GTCTACTGAA GTGACACTCT ACTTCCTCTC CCTTCTTGTC TTTCGGCTCC AAAAACCTGC TTGTGGAATG
     CCCGTTCCAT TTTCATCATC TAACCCTTCT CAGATGACTT CACTGTGAGA TGAAGGAGAG GGAAGAACAG AAAGCCGAGG TTTTGGACGG AACACCTTAC
748   G   K   V      K   V   V   D      W   E   E      S   T   E      V   T   L   Y      F   L   S      L   L   V      F   R   L   Q      N   L   P      C   G   M

2501 GAGAAGCTAG GCAGTGACGT TGCTACTCTC CGCATGTCGT CTCTCTGTG AGTGCAGCAG CCTGTCTATT GGGACAGCTT GGTCAGCAAG
     CTCTTCGATC CGTCACTGCA ACGATGAGAG AAATGGGTAA GCGTACAGCA GAGAGAACAC TCACGTCGTC GGACAGATAA CCCTGTCGAA CCAGTCGTTC
781   E   K   L   G      S   D   V      A   T   L      F   T   H   S      H   V   V      S   L   V      S   A   A   A      C   L   L      G   Q   L      G   Q   Q   G
```

FIG. 1D

```
2601 GGGTGACCTT TGACCTCCAG CCCATGGAAT GGATGGCTGC AGCCACACAT GCCTTGTCTG CCCCTGCAGA GGTTCGGTTG ACTCCACCAG GTAGTTGTGG
     CCCACTGGAA ACTGGAGGTC GGGTACCTTA CCTACCGACG TCGGTGTGTA CGGAACAGAC GGGGACGTCT CCAAGCCAAC TGAGGTGGTC CATCAACACC
 815  V  T  F    D  L  Q    P  M  E  W    M  A  A     T  H  A  L     S  A  P  A  E    V  R  L     T  P  P  G    S  C  G

2701 ATTCTATGAT GGCCTCCTTA TCCTTCTGTT GCAGCTCCTC ACTGAGCAGG GGAAGGCTAG CCTAATCAGG GATATGTCCA GTTCAGAAAT GTGGACCGTT
     TAAGATACTA CCGGAGGAAT AGGAAGACAA CGTCGAGGAG TGACTCGTCC CCTTCCGATC GGATTAGTCC CTATACAGGT CAAGTCTTTA CACCTGGCAA
 848  F  Y  D    G  L  L  I    L  L  Q  L    L  T  E  Q  G    K  A  S    L  I  R    D  M  S  S    S  E  M    W  T  V

2801 TTGTGGCACC GCTTCTCCAT GGTCCTGAGG CTCCCCGAGG AGGCATCTGC ACAGGAAGGG GAGCTTTCGC TATCCAGTCC ACCAAGCCCT GAGCCAGACT
     AACACCGTGG CGAAGAGGTA CCAGGACTCC GAGGGGCTCC TCCGTAGACG TGTCCTTCCC CTCGAAAGCG ATAGGTCAGG TGGTTCGGGA CTCGGTCTGA
 881  L  W  H  R    F  S  M    V  L  R    L  P  E  E    A  S  A    Q  E  G    E  L  S  L    S  S  P    P  S  P    E  P  D  W

2901 GGACACTGAT TTCTCCCCAG GGCATGGCAG CCCTGCTGAG CCAGTTATGC CCCAGGAGCC CCAGTTTATA CTGAGCTGCC TGTCCCAGCA
     CCTGTGACTA AAGAGGGGTC CCGTACCGTC GGGACGACTC GGTCAATACG GGGTCCTCGG GGTCAAATAT GACTCGACGG ACAGGGTCGT
 915  T  L  I    S  P  Q    G  M  A  A    L  L  S    L  A  M    A  T  F  T    Q  E  P    Q  L  C    L  S  C  L    S  Q  H

3001 TGGAAGTATC CTCATGTCCA TCCTGAAGCA TCTGCTTTGC CCCTTTGCGC TGGACATGGA TGCTGACCTC CTTATAGTTG TCTTGGCCGA CCTCAGGGAC TCAGAAGTTG
     ACCTTCATAG GAGTACAGGT AGGACTTCGT AGACGAAACG GGGAAACGCG ACCTGTACCT ACGACTGGAG GAATATCAAC AGAACCGGCT GGAGTCCCTG AGTCTTCAAC
 948  G  S  I    L  M  S  I    L  K  H    L  L  C    P  S  F  L    N  Q  L    R  Q  A    P  H  G  S    E  F  L    P  V  V

3101 GTGCTCTCTG TCTGCCAGCT CCTTTGCTTC CCCTTTGCGC GATGCAAGTG GAGCTGCCCA TCAGCCTTCT CACACGCCTG GCCCTCATGG ATCCCACCTC
     CACGAGAGAC AGACGGTCGA GGAAACGAAG GGGAAACGCG CTACGTTCAC CTCGACGGGT AGTCGGAAGA GTGTGCGGAC CGGGAGTACC TAGGGTGGAG
 981  V  L  S  V    C  Q  L    L  Q  V     L  C  F    P  F  A  L    D  M  D    A  D  L    L  I  V  V    L  A  D    L  R  D    S  E  V  A

3201 CAGCCCATCT GCTGCAGGTC CGACGTCCAG ACGACGATGG TAGAAGGCAA CTACGTTCAC ATCTTCCGTT GATGCAAGTG GAGCTGCCCA CGTTCTCTC AGTTGCCCTC CTGAGTGACC AGCCACTGTT GACCTCCGAC
     GTCGGGTAGA CGACGTCCAG GCTGCAGGTC TGCTGCTACC ATCTTCCGTT GATGCAAGTG TAGAAGGCAA CTACGTTCAC CGTTCTCTC GCAAAGAGAG TCAACGGGAG GACTCACTGG CTGGAGGCTG
1015  A  H  L    L  Q  V     C  C  Y  H    L  P  L    M  Q  V    E  L  P  I     S  L  L    T  R  L    A  L  M  D    P  T  S

3301 TCTCAACCAG TTTGTGAACA CAGTGTCTGC CTCCCCTAGA GAGGGGATCT TGGTAGCAGA ACCATCGTCT CGTTCTCTC AGTTGCCCTC CTGAGTGACC AGCCACTGTT GACCTCCGAC
     AGAGTTGGTC AAACACTTGT GTCACAGACG GAGGGGATCT ACCATCGTCT TGGTAGCAGA GCAAAGAGAG TCAACGGGAG GACTCACTGG CTGGAGGCTG
1048  L  N  Q    F  V  N  T    V  S  A     S  P  R    T  I  V  S    F  L  S    V  A  L    L  S  D  Q    P  L  L    T  S  D

3401 CTTCTCTC TGCTGGCCCA TACTGCCAGG GTCCTGTCTC CAGCCCACTT GTCCTTTATC CAAGAGCTTC TGATGAATCC TATCGGCCCC
     GAAGAGAGAG ACGACCGGGT ATGACGGTCC CAGGACAGAG GGTCGGGTGAA CAGGAAATAG GTTCTCGAAG ACTACTTAGG ATAGCCGGGG
1081  L  L  S  L    L  A  H    T  A  R    V  L  S  P    S  H  L    S  F  I    Q  E  L  L    A  G  S    D  E  S    Y  R  P  L
```

FIG. 1E

```
4101  GCATGTGATT CCAGATTCCT GCGGTCCAGC CTCCAACTTT GGTGCCAGCT CTTTCTTATN TAATACACAA GCGCCAAYTC AACTGAGAGC TAAAGAGACT
      CGTACACTAA GGTCTAAGGA CGCCAGGTCG GAGGTTGAAA CCACGGTCGA GAAAGAATAN ATTATGTGTT CGCGGTTRAG TTGACTCTCG ATTTCTCTGA
1315  M  O

4201  AGAAAAGAGA TAAGCTGCCA ACTCAACTGA GAACAGGAAA CTNGAAGAGA TTTATATATA AAGCTTCTTC CTTCTCCCAG ATGCAGGATG TTTTCAACCA
      TCTTTTCTCT ATTCGACGGT TGAGTTGACT CTTGTCCTTT GANCTTCTCT AAATATATAT TTCGAAGAAG GAAGAGGGTC TACGTCCTAC AAAAGTTGGT

4301  GTAAATTTTA TTGCTGTTGG TGCCAGAGAA GAGTCCCTTT CTTCTCTACA TCCAGGGGCC NTTTTCTCCA ATAATGTGCC TTTAACTCTA GGGACCTGCC
      CATTTAAAAT AACGACAACC ACGGTCTCTT CTCAGGGAAA GAAGAGATGT AGGTCCCCGG NAAAAGAGGT TATTACACGG AAATTGAGAT CCCTGGACGG

4401  TCACGGACCT TAGGGAAAAA CCTCAACCTG AAAGATCTCT TCCTTTCTGG AGCTCCTTTA ATCTTCCCAG CAGGTTTTTG CCTTAGACGT GCTGGCCCCA
      AGTGCCTGGA ATCCCTTTTT GGAGTTGGAC TTTCTAGAGA AGGAAAGACC TCGAGGAAAT TAGAAGGGTC GTCCAAAAAC GGAATCTGCA CGACCGGGGT

4501  GGACAGTGAT GAAGACAGAG CCTGTCTCAG CTCTAGGCTG TGGGGATCAA TGCCATCAGT CCCTGTTATT GAGGGATTAT CCCTTAGCCA ACATTCCTAT
      CCTGTCACTA CTTCTGTCTC GGACAGAGTC GAGATCCGAC ACCCCTAGTT ACGGTAGTCA GGGACAATAA CTCCCTAATA GGGAATCGGT TGTAAGGATA

4601  CTGTGGGTGG GCGTGGAGAG TGTATCTTTT TTTGGGGTGT GTGTGTATAT GTGTGTGTGT ATGTGTGTGT CACACACACA GTTCTGTTTG TAAACTCTTT
      GACACCCACC CGCACCTCTC ACATAGAAAA AAACCCCACA CACACATATA CACACACACA TACACACACA CAAGACAAAC ATTTGAGAAA

4701  TAATAAAAGT TGTGCCTCAC CATACTTGAA GCTCCCAGGA CAAGGGTTGA GAGGCTCAAC CCCTCTTTCA GCTTCTATGT GGTGTTGGAG GTGCTGGTAT
      ATTATTTTCA ACACGGAGTG GTATGAACTT CGAGGGTCCT GTTCCCAACT CTCCGAGTTG GGGAGAAAGT CGAAGATACA CCACAACCTC CACGACCATA

4801  CGTGTTCACA CAAAAAAAAA AAAAAAAAAA AAAAAAAAAA AAAAAAAAAA
      GCACAAGTGT GTTTTTTTTT TTTTTTTTTT TTTTTTTTTT TTTTTTTTTT
```

FIG. 1F

CCCGGGCTATGAGCACCAATACAATGGTGCTGACATCCATCAAAGGCACACCACTCTATA
TGTCTCCAGAGCTGGTGGAGGAGCGACCATACGACCACACAGCGGACCTCTGGTCTGTTG
GCTGCATACTATATGAACTGGCAGTAGGCACCCCTCCCTTCTAATGCTACAAGCATCTTT
CAGCTGGTCAGCC

FIG. 2

```
hfused    1 MEKYHVLEMIGEGSFGRVYKGRRKYSAQVVALKFIPKLGRSEKELRNLQR
dfused    1 MDRYAVSSLVGQGSFGCVYKAQRDDKVVAIKVISKRGRSNRELKNLRR hfused   51 EIEIMRGLRHPNIVHMLDSFETDKEVVVTDYAEGELFQILEDDGKLPED
dfused   51 ECDIQARLKHPHVIEMVESFESKFDLFVVTEFALMDLHRYLSFNGAMPEE hfused  101 QVQAIAAQLVSALYYLHSHRILHRDMKPQNILLAKGGGIKLCDFGFARAM
dfused  101 HAQRVVCHLVSALYYLHSNRILHRDLKPQNVLLDKNMHAKLCDFGLARNM hfused  151 STNTMVLTSIKGTPLYMSPELVEERPYDHTADLWSVGCILYELAVGTPPF
dfused  151 TMGTHVLTSIKGTPLYMAPELLAEQPYDHQADMWSLGCIAYESMAGQPPF hfused  201 YATSIFQLVSLILKDPVRWPSTISPCFKNFLQGLLTKDPRQRLSWPDLLY
dfused  201 CATSILHLVKLIKHEDVKWPSTLSECRSFLQGLLEKDPSMRISWTQLLC
```

FIG. 3A

```
hfused  251  HPFIAGHVTIITEPAGPDLGTPPFTSRLPPELQVLKDEQAHRLAPKGNQSR
dfused  251  HPFVEGKL-YIAEVQAAQTSPFINPQLAKDTK--KSQQLRHVGADLGDVhfused  301  ILTQAYKRMAEEAMQKKHQNTGPALEQEDKTSKVAPGTAPLPRLGATPQE
dfused  297  LAALKLSDVANENLSTSRDSIN-AIAPSDIEQLETDVEDNVHRL-IVP-- hfused  351  SSLLAGILASELKSSWAKSGTGEVPSAPRENRTTPDC-ERAFPEERPEVL
dfused  343  ---FADISYRELPCG---TAAAARRAGAMPLINSQTCFVSGNSNMILNHL hfused  400  GQRSTDVVDLENEEPDSDNEWQHLLETTEPVPIQLKAPLTLLCNPDFCQR
dfused  387  NDNFAIEAPASSATKSMKSKLKLALNIKQSRSKDLEKRKLSQNLDNFSLR hfused  450  IQSQLHEAGGQILKGILEGASHILPAFRVLSSLLSSCSDSVALYSFCREA
dfused  437  LGQSIDIEVQRKTTEMLTQQSQAQQLQDRKTQQLKQSMHSTNDEKLSSDN
```

FIG. 3B

```
hfused  500  GLPGLLLSLLR·HSQESNSLQQQSWYGTFLQDLMAVIQAYFACTFNLE·R
dfused  487  SPPCLLPGWDSCDESQSPPIENDEWLAFLHRSIQELLDGEFDSLKQHNLV hfused  548  SQTSDSLQVFQEAANLFLDLLGKLLAQPDDSEQTLQRDSLMCFTVLCEAM
dfused  537  SIIVAPLRNSKAIPKV·LQSVAQLSLP····FVLAEQHLVAEAI··KGV hfused  598  DGNSRAISKAFYSSLLTTQQVVLDGLLHGLTVPQLPVHTPQGAPQVSQPL
dfused  580  YIDVKLVPNLMYACKLLSQRHLTD·····SAASLPAGTGVSLSRTVRSC hfused  648  REQSEDIPGAISALAAICTAPVGLPDCWDAKEQVCWHLAN·QLTEDSSQ
dfused  625  SDLSAEEMSTACSLYELVCHLVHQQQQFL···TQFCDAVAILAVNDMFIN hfused  697  LRPSLISGLQHPILCLHLLKVLYSCCLVSE··GLCRLLGQEPLALE·SLF
dfused  672  FLTHDFKDSRPVRLASCML·ALF·CCVLRELPENAELVEKIVFDSRLQLA
```

FIG. 3C

```
hfused  744  M L I Q G K V K V V D W E E S T E V T L Y F L S L L V F R L Q N L P C G - M E K L G S D V A T L F T
dfused  720  V L L Q S R H H L L - R Q R A C Q M - - - L L L A R F S L R G V Q C I W S G E L K S A L Q A W P M hfused  793  H S H V V S L V S A A A C L G Q L G Q Q G V T F D L Q P M E W M A A A T H A L S A P A E V R L T P
dfused  766  Q Q T C Q S L R L E A A Q T L D E L S Q F S F - F V A Q A T A hfused  843  P G S C G F Y D G L L I L L L Q L L T E Q G K A S L I R D M S S S E M W T V L W H R F S M V L R L P hfused  893  E E A S A Q E G E L S L S S P P S P E P D W T L I S P Q G M A A L L S L A M A T F T Q E P Q L C L S hfused  943  C L S Q H G S I L M S I L K H L L C P S F L N Q L R Q A P H G S E F L P V V V L S V C Q L L C F P F hfused  993  A L D M D A D L L I V V L A D L R D S E V A A H L L Q V C C Y H L P L M Q V E L P I S L L T R L A L
```

FIG. 3D

| | | |
|---|---|---|
| hfused | 1043 | MDPTSLNQFVNTVSASPRTIVSFLSVALLSDQPLLTSDLLSLLAHTARVL |
| hfused | 1093 | SPSHLSFIQELLAGSDESYRPLRSLLGHPENSVRAHTYRLLGHLLQHSMA |
| hfused | 1143 | LRGALQSQSGLLSLLLLGLGDKDPVVRCSASFAVGNAAYQAGPLGPALAA |
| hfused | 1193 | AVPSMTQLLGDPQAGIRRNVASALGNLGPEGLGEELLQCEVPQRLLEMAC |
| hfused | 1243 | GDPQPNVKEAALIALRSLQQEPGIHQVLVSLGASEKLSLLSLGNQSLPHS |
| hfused | 1293 | SPRPASAKHCRKLIHLLRPAHSM |

FIG. 3E

> length: 5125 bp (circular)

```
  1 CCCACGGGTC CGCCCACGCG TCCGGGGCGT CCCAGATGTT GTGGAACTGT CCCTGGATCT ATAGCTCTTC ACCGTCTCTA CTTTCTTCCT TCTAAGAGAT
    GGGTGCCCAG GCGGGTGCGC AGCCCCGCA  GGGTCTACAA CACCTTGACA GGGACCTAGA TATCGAGAAG TGGCAGAGAT GAAAGAAGGA AGATTCTCTA

101 CCTGAAACCT CTGTCATGGA AAAGTACCAC GTGTTGGAGA TGATTGGAGA AGGCTCTTTT GGGAGGGTGT ACAAGGGTCG AAGAAAATAC AGTGCTCAGG
    GGACTTTGGA GACAGTACCT TTTCATGGTG CACAACCTCT ACTAACCTCT TCCGAGAAAA CCCTCCCACA TGTTCCCAGC TTCTTTTATG TCACGAGTCC
  1             M  E  K  Y  H  V  L  E  M  I  G  E  G  S  F  G  R  V  Y  K  G  R  R  K  Y  S  A  Q  V
                ^Start of 1st ORF!

201 TCGTGGCCCT GAAGTTCATC CCAAAATTGG GGCGCTCAGA GAAGGAGCTG AGGAATTTGC AACGAGAGAT TGAAATAATG CGGGGTCTGC GGCATCCCAA
    AGCACCGGGA CTTCAAGTAG GGTTTTAACC CCGCGAGTCT CTTCCTCGAC TTGCTCTCTA ACTTTATTAC GCCCCAGACG CCGTAGGGTT
 30  V  A  L  K  F  I  P  K  L  G  R  S  E  K  E  L  R  N  L  Q  R  E  I  E  I  M  R  G  L  R  H  P  N

301 CATTGTGCAT ATGCTTGACA GCTTTGAAAC TGATAAAGAG GTGGTGGTGG TGCTGAGGGA GAGCTCTTTC AGATCCTAGA AGATGACGGA
    GTAACACGTA TACGAACTGT CGAAACTTTG ACTATTTCTC CACCACCACC ACGACTCCCT CTCGAGAAAG TCTAGGATCT TCTACTGCCT
 63  I  V  H  M  L  D  S  F  E  T  D  K  E  V  V  V  V  L  R  E  S  S  F  Q  I  L  E  D  D  G

401 AAACTTCCTG AAGACCAGGT TCAGGCCATT GCTGCCCAGT TGGTGTCAGC CCTGTACTAT CTGCATTCCC ACCGCATCCT ACACCGAGAT ATGAAGCCTC
    TTTGAAGGAC TTCTGGTCCA AGTCCGGTAA CGACGGGTCA ACCACAGTCG GGACATGATA GACGTAAGGG TGGCGTAGGA TGTGGCTCTA TACTTCGGAG
 96  K  L  P  E  D  Q  V  Q  A  I  A  A  Q  L  V  S  A  L  Y  Y  L  H  S  H  R  I  L  H  R  D  M  K  P  Q

501 AGAACATCCT CCTCGCCAAG GGTGGTGGCA TCAAGCTCTG AGTTCGAGAC ACTGAAACCT TTTGCCCGGG CTATGAGCAC GTGCTGACAT CCATCAAAGG
    TCTTGTAGGA GGAGCCGTTC CCACCACCGT AGTTCGAGAC TCAAGCTCTG TGACTTTGGA AAACGGGCCC GATACTCGTG CACGACTGTA GGTAGTTTCC
130  N  I  L  L  A  K  G  G  G  I  K  L  C  D  F  G  F  G  I  K  L  C  D  F  A  R  A  M  S  T  N  T  M  V  L  T  S  I  K  G

601 CACACCACTC TATATGTCTC CAGAGCTGGT GGAGGAGCGA CCATACGACC ACACAGCGGA CCTCTGGTCT GTTGGCTGCA TACTATATGA ACTGGCAGTA
    GTGTGGTGAG ATATACAGAG GTCTCGACCA CCTCCTCGCT GGTATGCTGG TGTGTCGCCT GGAGACCAGA CAACCGACGT ATGATATACT TGACCGTCAT
163  T  P  L  Y  M  S  P  E  L  V  E  E  R  P  Y  D  H  T  A  D  L  W  S  V  G  C  I  L  Y  E  L  A  V
```

FIG. 4A

```
701  GGCACCCCTC CCTTCTATGC TTTCAGCTGG TCAGCCTCAT TCTCAAGGAC CCTGTGCGCT CATCAGTCCC TGCTTTAAGA
     CCGTGGGGAG GGAAGATACG AAAGTTCGAC AGTCGGAGTA AGAGTTCCTG GGACACGCGA GTAGTCAGGG ACGAAATTCT
196  G  T  P  P  F  Y  A  T  S  I  F  Q  L  V  S  L  I  L  K  D  P  V  R  W  P  S  T  I  S  P  C  F  K  N

801  ACTTCCTGCA GGGACTGCTC ACCAAAGACC CCAGAGCTCT CCAGACCTCT TATATCACCC CTTTATTGCT GGTCATGTCA CCATAATAAC
     TGAAGGACGT CCCTGACGAG TGGTTTCTG  GTCCGTCGC  TGACAGGACC GGTCTGGAGA ATATAGTGGG GAAATAACGA CCAGTACAGT GGTATTATTG
230  F  L  Q  G  L  L  T  K  D  P  R  Q  R  L  S  W  P  D  L  L  Y  H  P  F  I  A  G  H  V  T  I  I  I  T

901  TGAGCCAGCA GGCCCAGATT TGGGGACCCC ATTCACCAGC CGCCTACCCC CAGAACTTCA GGTCCTAAAG GACGAACAGG CCCATCGGTT GGCCCCCAAG
     ACTCGGTCGT CCGGGTCTAA ACCCCTGGGG TAAGTGGTCG GCGGATGGGG GTCTTGAAGT CCAGGATTTC CTGCTTGTCC GGGTAGCCAA CCGGGGGTTC
263  E  P  A  G  P  D  L  G  T  P  F  T  S  R  L  P  P  E  L  Q  V  L  K  D  E  Q  A  H  R  L  A  P  K

1001 GGTAATCAGT CTCGCATCTT GACTCAGGCC TATAAACGCA TGGCTGAGGA GGCCATGCAG AAGAACACAG ACCTGCCCTT GAGCAAGAGG
     CCATTAGTCA GAGCGTAGAA CTGAGTCCGG ATATTTGCGT ACCGACTCCT CCGGTACGTC TCTTGTGTC  TGGACGGGAA CTCGTTCTCC
296  G  N  Q  S  R  I  L  T  Q  A  Y  K  R  M  A  E  E  A  M  Q  K  K  H  Q  N  T  G  P  A  L  E  Q  E  D

1101 ACAAGACCAG CAAGGTGGCT CCTGGCACAG CCCCTCTGCC CAGACTCGGG GCCACTCCTC AGGAATCAAG CCTCCTGCC  GGGATCTTAG CCTCAGAATT
     TGTTCTGGTC GTTCCACCGA GGACCGTGTC GGGGAGACGG GTCTGAGCGC CGGTGAGGAG TCCTTAGTTC GGAGGACGG  CCCTAGAATC GGAGTCTTAA
330  K  T  S  K  V  A  P  G  T  A  P  L  P  R  L  G  A  T  P  Q  E  S  S  L  L  A  G  I  L  A  S  E  L

1201 GAAGAGCAGC TGGGCTAAAT CAGGGACTGG AGAGGTGCCC TCTGCACCTC GGGAAAAACCG GATTGTGAAC GAGCATTCCC AGAGGAGAGG
     CTTCTCGTCG ACCCGATTTA GTCCCTGACC TCTCCACGGG AGACGTGGAG CCCTTTTGGC CTAACACTTG CTCGTAAGGG TCTCCTCTCC
363  K  S  S  W  A  K  S  G  T  G  E  V  P  S  A  P  R  E  N  R  T  T  P  D  C  E  R  A  F  P  E  E  R

1301 CCAGAGGTGC TGGGCCAGCG GAGCACTGAT GTAGTGGACC TGGAAAATGA GGAGCCAGAG CCTCGGTCG  AGTGACAATG CCTGCTAGAG ACCACTGAGC
     GGTCTCCACG ACCCGGTCGC CTCGTGACTA CATCACCTGG ACCTTTTACT CCTCGGTCTC GGAGCCAGC  TCACTGTTAC GGACGATCTC TGGTGACTCG
396  P  E  V  L  G  Q  R  S  T  D  V  V  D  L  E  N  E  E  P  D  S  D  N  E  W  Q  H  L  L  E  T  T  E  P

1401 CTGTGCCTAT TCAACTGAAG GTCCTCTCA  CCTTGCTGTG TAATCCTGAC TTCTGCCAGC GCATCCAGAG TCAGCTGCAT GAAGCTGGAG GGCAGATCCT
     GACACGGATA AGTTGACTTC CGAGGAGAGT GGAACGACAC ATTAGGACTG AAGACGGTCG CGTAGGTCTC AGTCGACGTA CTTCGACCTC CCGTCTAGGA
430  V  P  I  Q  L  K  A  P  L  T  L  L  C  N  P  D  F  C  Q  R  I  Q  S  Q  L  H  E  A  G  G  Q  I  L

1501 GAAAGGCATC TTGGAGGGTG CTTCCCACAT CCTGCCTGCA TTCCGGTCC  TGCAGTCTCT TCTCTCCCAG AAGGCCCAGG ACTCGTCAGA GACAAGGAAG
     CTTTCCGTAG AACCTCCCAC GAAGGGTGTA GGACGGACGT AAGGCCAGG  ACGTCAGAGA AGAGAGGGTC TTCCGGGTCC TGAGCAGTCT CTGTTCCTTC GTATTCCTTC
463  K  G  I  L  E  G  A  S  H  I  L  P  A  F  R  V  L  S  S  L  S  S  C  S  D  S  V  A  L  Y  S  F
```

FIG. 4B

```
1601 TGCCGGGAGG CAGGGCTTCC TGGGCTGCTG CTGAGTCTAC TCAGGCACAG AACAGCCTCC AGCAGCAATC TTGGTATGGG ACCTTCTTAC
     ACGGCCCTCC GTCCCGAAGG ACCCGACGAC GACTCAGATG AGTCCGTGTC TTGTCGGAGG TCGTCGTTAG AACCATACCC TGGAAGAATG
496  C  R  E  A  G  L  P  G  L  L  L  S  L  L  R  H  S  Q  E  S  N  S  L  Q  Q  Q  S  W  Y  G  T  F  L  Q

1701 AGGACCTGAT GGCTGTGATT CAGGCCTACT TTGCCTGTAC CTTCAATCTG GAGAGGAGCC AGACAAGTGA CAGCCTGCAG GTGTTTCAGG AGGCTGCCAA
     TCCTGGACTA CCGACACTAA GTCCGGATGA AACGGACATG GAAGTTAGAC CTCTCCTCGG TCTGTTCACT GTCGGACGTC CACAAAGTCC TCCGACGGTT
530  D  L  M  A  V  I  Q  A  Y  F  A  C  T  F  N  L  E  R  S  Q  T  S  D  S  L  Q  V  F  Q  E  A  A  N

1801 CCTTTTTCTG GACCTGTTGG GGAAACTGCT GGCCCAACCA GATGACTCTG AGCAGACTTT GCAGAGGGAC AGCCTTATGT GCTTTACTGT CCTGTGCGAA
     GGAAAAAGAC CTGGACAACC CCTTTGACGA CCGGGTTGGT CTACTGAGAC TCGTCTGAAA CGTCTCCCTG TCGGAATACA CGAAATGACA GGACACGCTT
563  L  F  L  D  L  L  G  K  L  L  A  Q  P  D  D  S  E  Q  T  L  Q  R  D  S  L  M  C  F  T  V  L  C  E

1901 GCCATGGATG GGAACAGCCG GGCCATCTCC AAAGCCTTTT ACTCCCAGCT TGCTGACACA CAGCAGGTTG TCTTGGATGG GCTCCTTCAT GGCTTGACAG
     CGGTACCTAC CCTTGTCGGC CCGGTAGAGG TTTCGGAAAA TGAGGTCGAA CGACTGCTGT GTCGTCCAAC AGAACCTACC CGAGGAAGTA CCGAACTGTC
596  A  M  D  G  N  S  R  A  I  S  K  A  F  Y  S  Q  L  L  T  T  Q  Q  V  V  L  D  G  L  L  H  G  L  T  V

2001 TTCCACAGCT CCCTGTCCAC ACTCCCCAAG GTAACCAGAG AGGTTCTCTT GACTTACTTG TTGCATAGGT CAGGCTCCGC TCTTTCTATT
     AAGGTGTCGA GGGACAGGTG TGAGGGGTTC CATTGGTCTC TCCAAGAGAA CTGAATGAAC AACGTATCCA GTCCGAGGCG AGAAAGATAA
630  P  Q  L  P  V  H  T  P  Q  G  N  Q  S  G  E  G  R  F  S  Q
                                                               ^Start of intron sequence 2101 GCCATCACCT AGATCGCACC TGGCATTAG  TAGGTGCTCA ATAAATAACT GTGAACTGAG AGAATGAATG GGGATCTGAG GGAAACAAAC AGACCTCATC
     CGGTAGTGGA TCTAGCGTGG ACCGTAAATC ATCCACGAGT TATTTATTGA CACTTGACTC TCTTACTTAC CCCTAGACTC CCTTGTTTG  TCTGGAGTAG 2201 CTGCATTCTT CCCACTCCCT TAGTTCCCT  ACTCCTGCTG GGTACAGCCA CGATAACCAGA GAGTACTGGT GCTATTGTCT AGGGCAAGAG CCTCAGGCCT TTGAGTTAC
     GACGTAAGAA GGGTGAGGGA ATCCAAGGGA TGAGGACGAC CCATGTCGGT GCTATTGGTCT CTCATGACCA CGATAACCAGA GAGTACTGGT GCTATTGTCT AGGGCAAGAG CCTCAGGCCT AACCTCAATG
1                                                                                                                        S  Y
                                                                                                    2nd ORF starts from here!^

2301 TCTTTGCTTT TCTCCACAGG AGCCCCGCAA GTGAGCCAGC CACTGCGAGA GCAGAGTGAG GATATACCTG GAGCCATTTC CTCTGCCCTG GCAGCCATAT
     AGAAACGAAA AGAGGTGTCC TCGGGGCGTT CACTCGGTCG GTGACGCTCT CGTCTCACTC CTATATGGAC CTCGGTAAAG GAGACGGGAC CGTCGGTATA
3    S  L  F  S  T  G  A  P  Q  V  S  Q  P  L  R  E  Q  S  E  D  I  P  G  A  I  S  S  A  L  A  A  I  C

2401 GCACTGCTCC TGTGGGACTG CCCGACTGCT GGGATGCCAA GGAGCAGGTC TGTTGGCATT TGGCAAATCA GCTAACTGAA GACAGCAGCC AGCTCAGGCC
     CGTGACGAGG ACACCCTGAC GGGCTGACGA CCCTACGGTT CCTCGTCCAG ACAACCGTAA ACCGTTTAGT CGATTGACTT CTGTCGTCGG TCGAGTCCGG
37   T  A  P  V  G  L  P  D  C  W  D  A  K  E  Q  V  C  W  H  L  A  N  Q  L  T  E  D  S  S  Q  L  R  P
```

FIG. 4C

```
2501  ATCCCCTCATC TCTGGCCTGC AGCATCCCAT AGTTCTATA CTCCTGCCTG CTTGTCAGTG AGGGCCTGTG CCGTCTTCTG
      TAGGGAGTAG AGACCGGACG TCGTAGGGTA TCAAGAGAT GAGGACGAC TCCCGGACAC GGCAGAAGAC
 70    S  L  I   S  G  L  Q   H  P  I   L  C  L    H  L  L  K    V  L  Y    S  C  C    L  V  S  E    G  L  C    R  L  L

2601  GGGCAGGAGC CCCTGGCCTT GGAATCCCTG TTTATGTTGA GGTAAAAGTA TTCAGGCAA GTAGATTGGG AAGAGTCTAC CTCCTACTTCC
      CCCGTCCTCG GGGACCGGAA CCTTAGGGAC AAATACAACT CCATTTCAT AAGTCCCGTT CATCTAACCC TTCTCAGATG GAGATGAAGG
103    G  Q  E   P  L  A  L    E  S  L    F  M  L   I    Q  G  K    V  K  V   V  D  W  E     S  T    E  V  T    L  Y  F  L

2701  TCTCCCTTCT TGTCTTTCGG CTCCAAAACC TGCCTTGTGG AATGGAGAAG CTAGGCAGTG ACGTTGCTAC TCTCTTTACC CATTCGCATG TCGTCTCTCT
      AGAGGGAAGA ACAGAAAGCC GAGGTTTTGG ACGGAACACG TTACCTCTTC GATCCGTCAC TGCAACGATG AGAGAAATGG GTAAGCGTAC AGCAGAGAGA
137    S  L  L   V  F  R    L  Q  N  L   P  C  G    M  E  K    L  G  S  D     V  A  T    L  F  T     H  S  H  V     V  S  L

2801  TGTGAGTGCA GCAGCCTGTC TATTGGGACA CAAGGGGTGA CCTTTGACCT CCAGCCCATG CTAGGCAGT ACGTTGCTGG CTGCAGCCAC ACATGCCTTG
      ACACTCACGT CGTCGGACAG ATAACCCTGT GTTCCCCACT GGAAACTGGA GGTCGGGTAC GATCCGTCA TGCAACGACC GACGTCGGTG TGTACGGAAC
170    V  S  A   A  A  C   L    L  G  Q    L  G  Q    Q  G  V  T    F  D  L    Q  P  M    E  W  M  A    A  A  T    H  A  L

2901  TCTGCCCCTG CAGAGGTTCG GTTGACTCCA CCAGGTAGTT CAACCTAAGA CACCTAAGAT ACTACCGGAG TGTTGCAGCT CCTCACTGAG CAGGGGAAGG
      AGACGGGGAC GTCTCCAAGC CAACTGAGGT GGTCCATCAA GTTGGATTCT TGATGGCCTC AATACCGGAG GAATAGGAAG ACAACGTCGA GGAGTGACTC GTCCCCTTCC
203    S  A  P  A   E  V  R    L  T  P   P  G  S  C    G  F  Y    D  G  L    L  I  L    L  Q  L    L  T  E     Q  G  K  A

3001  CTAGCCTAAT CAGGGATATG TCCAGTTCAG AAATGTGGAC CGTTTTGTGG GCAAAACACC GACTGGACAC TGATTTCTCC CCATGGTCCT GAGGAGGCAT CTGCACAGGA
      GATCGGATTA GTCCCTATAC AGGTCAAGTC TTTACACCTG GCAAAACACC CTGACCTGTG ACTAAAGAGG GGTACCAGGA CTCCTCCGTA GACGTGTCCT
237    S  L  I   R  D  M    S  S  S  E    M  W  T    V  L  W    H  R  F  S     M  V  L    R  L  P    E  E  A  S     A  Q  E

3101  AGGGGAGCTT TCGCTATCCA GTCCACCAAG GTCCCACAAG CAGGGGTTC CAGGGGCATG GTGGCGAAGA TGATTTCTCC GCAGCCCTGC CGTCGGACCG GTACCGGTGG
      TCCCCTCGAA AGCGATAGGT CAGGTGGTTC CAGGGTCAA GGCTGCCGTTC CTGACCTGTG ACTAAAGAGG CCAGGGGCATG CGACTAGTAG GTCCCGAAGG CTGGCCACCG CATGCCACC GCAGGCCGG GTACCGGTGG
270    G  E  L   S  L  S  S   P  P  S     M  W  T    V  L  W    H  R  F  S     M  V  L    R  L  P    E  E  A  S    A  Q  E

3201  TTTACCAGG AGCCCCAGTT TGCGTGTCC TGCCTGTCCC AGCATGGAAG TATCCTCATG TCCATCCTGA AGCATCCTGCT TTCCTGAATC TTGCCCCAGC TTCCTGAATC
      AAATGGGTCC TCGGGGTCAA AGCGATAGGT ACGGACAGGG ACGGACTACG TCGTACCTTTC ATAGGAGTAC AGGTAGGACT TCGTAGAGCA AACGGGGTCG AAGGACTTAG
303    F  T  Q  E    P  Q  L    C  L  S    C  L  S  Q    H  G  S    I  L  M    S  I  L  K    H  H  L    C  P  S    F  L  N  Q

3301  AACTGCGCCA GGCGCCTCAG GGCTCTGAGT TTCTCCCTGT CGTGGTGCTC GTGGTGCTC CTGAGGAAAC TCGAGGAAAC AGTCCTTCGC CTTCCCCTTT GGCCTGGACA TGGATGCTGA
      TTGACGCGGT CCGCGGAGTA CCCAGACTCA AAGAGGGACA AGACAGACA AGACAGACAG CTTGAAAAT TCGAGGAAAC AGTCCCTGAGA GGAAGGGAAAA CGGACCTGT ACCTACGACT
337    L  R  Q    A  P  H    G  S  E  F    L  P  V  V  L    S  V  C  Q    L  L  C    F  P  F    A  L  D  M    D  A  D
```

FIG. 4D

```
3401 CCTCCTTATA GTTGTCTTGG CCGACCTCAG GGACTCAGAA GTTGCAGCCC ATCTGCTGCA GGTCTGCTGC TACCATCTTC CGTTGATGCA AGTGGAGCTG
     GGAGGAATAT CAACAGAACC GGCTGGAGTC CCTGAGTCTT CAACGTCGGG TAGACGACGT CCAGACGACG ATGGTAGAAG GCAACTACGT TCACCTCGAC
370    L  L  I   V  V  L  A   D  L  R    D  S  E    V  A  A  H    L  L  Q     V  C  C     Y  H  L  P    L  M  Q    V  E  L

3501 CCCATCAGCC TTCTCACACG CCTGGCCCTC ATGGATCCCA CCTCTCTCAA CCAGTTTGTG AACACAGTGT CTGCCTCCCC TAGAACCATC GTCTCGTTTC
     GGGTAGTCGG AAGAGTGTGC GGACCGGGAG TACCTAGGGT GGAGAGAGTT GGTCAAACAC TTGTGTCACA GACGGAGGGG ATCTTGGTAG CAGAGCAAAG
403    P  I  S  L   L  T  R     L  A  L     M  D  P  T    S  L  N     Q  F  V    N  T  V  S    A  S  P    R  T  I    V  S  F  L

3601 TCTCAGTTGC CCTCCTGAGT GACCAGCCAC TGTTGACCTC CGACCTTCTC TCTCTGCTGG CCCATACTGC CAGGGTCCTG TCTCCCAGCC ACTTGTCCTT
     AGAGTCAACG GGAGGACTCA CTGGTCGGTG ACAACTGGAG GCTGGAAGAG AGAGACGACC GGGTATGACG GTCCCAGGAC AGAGGGTCGG TGAACAGGAA
437    S  V  A    L  L  S    D  Q  P  L    L  T  S    D  L  L     S  L  L  A    H  T  A     R  V  L    S  P  S  H     L  S  F

3701 TATCCAAGAG CTTCTGGCTG GCTCTGATGA ATCCTATCGG CCACCCAGAG GCCTCCTGGG AATTCTGTGC GGGCACACAC TTATAGGCTC
     ATAGGTTCTC GAAGACCGAC CGAGACTACT TAGGATAGCC GGTGGGTCTC CGGAGGACCC TTAAGACACG CCCGTGTGTG AATATCCGAG
470    I  Q  E     L  L  A  G     S  D  E     S  Y  R    P  L  R  S    L  L  G    H  P  E     N  S  V  R    A  H  T     Y  R  L

3801 CTGGGACACT TGCTCCAACA CAGCATGGCC CTGCGTGGGG CACTGCAGAG CCAGTCTGGA CTGCTCAGCC TTCTGCTGCT TGGGCTTGGA GACAAGGATC
     GACCCTGTGA ACGAGGTTGT GTCGTACCGG GACGCACCCC GTGACGTCTC GGTCAGACCT GACGAGTCGG AAGACGACGA ACCCGAACCT CTGTTCCTAG
503    L  G  H  L    L  Q  H     S  M  A     L  R  G  A    L  Q  S     Q  S  G     L  L  S  L    L  L  L     G  L  G    D  K  D  P

3901 CTGTTGTGCG GTGCAGTGCC AGCTTTGCTG TGGGCAATGC AGCCTACCAG TCGGATGGTC CGACCAGGAG ACCCTGGACG GCTGGTCCTC CCTGGCAGCT GCAGTGCCCA GTATGACCCA
     GACAACACGC CACGTCACGG TCGAAACGAC ACCCGTTACG TCGGATGGTC AGCCTACCAG GCTGGTCCTC TGGGACCTGC CGACCAGGAG GGACCGTCGA CGTCACGGGT CATACTGGGT
537    V  V  R    C  S  A     S  F  A  V     G  N  A     A  Y  Q     L  Q  S     Q  S  G     L  L  S  L     L  L  G    P  A     L  A  A    A  V  P  S    M  T  Q
```

```
4201  TCCATCAGGT ACTGGTGTCC CTGGGTGCCA GTGAGAAACT ATCCTTGCTC TCTCTGGGGA ATCAGTCACT GCCACACAGC AGTCCTAGGC CTGCCTCTGC
      AGTAGTCCA  TGACCACAGG GACCCACGGT CACTCTTTGA TAGGAACGAG AGAGACCCCT TAGTCAGTGA CGGTGTGTCG TCAGGATCCG GACGGAGACG
 637   H  Q  V   L  V  S     L  G  A  S    E  K  L    S  L  L    S  L  G  N    Q  S  L     P  H  S     S  P  R  P    A  S  A

4301  CAAACACTGC AGGAAACTCA TTCACCTCCT GAGGCCAGCC CATAGCATGT GATTCCAGAT TCCTGCGGTC CAGCCTCCAA CTTTGGTTGC CAGTCTCTTC
      GTTTGTGACG TCCTTTGAGT AAGTGGAGGA CTCCGGTCGG GTATCGTACA CTAAGGTCTA AGGACGCCAG GTCGGAGGTT GAAACCAACG GTCGAGAAAG
 670   K  H  C   R  K  L  I    H  L  L    R  P  A    H  S  M  O

4401  TTATTCTACT ACACAAGCCG CCAACTCAAC TGAGAGCTAA AGAGACTAGA AAAGAGATAA GCTGCCAACT CAACTGAGAA CAAGAAACTA GAAGAGATTT
      AATAAGATGA TGTGTTCGGC GGTTGAGTTG ACTCTCGATT TCTCTGATCT TTTCTCTATT CGACGGTTGA GTTGACTCTT GTTCTTTGAT CTTCTCTAAA

4501  ATATATAAAG CTTCTTCCTT CTCCCAGATG CAGGATGTTT TCAACCAGTA AATTTTATTG CTGTTGGTGC CAGAGAAGAG TCCTTTCTTC TCTACATCCA
      TATATATTTC GAAGAAGGAA GAGGGTCTAC GTCCTACAAA AGTTGGTCAT TTAAAATAAC GACAACCACG GTCTCTTCTC AGGAAAGAAG AGATGTAGGT

4601  GGGGCCTTTT CTCCAATAAT GTGCCTTTAA CTCTAGGGAC CTGCCTCACG GACCTTAGGG AAAAACCTCA ACCTGAAAGA TCTCTTCCTT TCTGAGCTC
      CCCCGGAAAA GAGGTTATTA CACGGAAATT GAGATCCCTG GACGGAGTGC CTGGAATCCC TTTTTGGAGT TGGACTTTCT AGAGAAGGAA AGACCTCGAG

4701  CTTTAATCTT CCCAGCAGGT TTTTGCCTTA GACGTGCTGG CCCCAGACA  GTGATGAAGA CAGAGCCTGT CTCAGCTCTA GGCTGTGGGG ATCAATGCCA
      GAAATTAGAA GGGTCGTCCA AAAACGGAAT CTGCACGACC GGGGTCCTGT CACTACTTCT GTCTCGAGAT GAGTCGAGAC CCGACACCCC TAGTTACGGT

4801  TCAGTCCCTG TTATTGAGGG ATTATCCCTT AGCCAACATT CCTATCTGTG GGTGGGCGTG GAGAGTGTAT CTTTTTTTGG GGTGTGTGTG TATATGTGTG
      AGTCAGGGAC AATAACTCCC TAATAGGGAA TCGGTTGTAA GGATAGACAT CCACCCGCAC CTCTCACATA GAAAAAAACC CCACACACAC ATATACACAC

4901  TGTGTATGTG TGTGTGTGTT GTTTGTAAAC TCTTTTAATA AAAGTTGTGC CTCACCATAC TTGAAGCTCC CAGGACAAGG GTTGAGAGGC
      ACACATACAC ACACACACAA CAAACATTTG AGAAAATTAT TTTCAACACG GAGTGGTATG AACTTCGAGG GTCCTGTTCC CAACTCTCCG

5001  TCAACCCCTC TTTCAGCTTC TATGTGGTGT TGGAGGTGCT GGTATCGTGT TCACACAAAA AAAAAAAAAA AAAAAAAAA AAAAAAAA
      AGTTGGGGAG AAAGTCGAAG ATACACCACA ACCTCCACGA ACCATAGCACA AGTGTGTTTT TTTTTTTTTT TTTTTTTTT TTTTTTTT

5101  AAAAAAAAAA AAAAAAAAAA AAAAA
      TTTTTTTTTT TTTTTTTTTT TTTTT
```

FIG. 4F

> length: 5252 bp (circular)

```
  1 GGAGCTTGGA GCTCCTAGGC TGGGGGCGTC CCAGATGTTG TGGAACTGTC CCTGGATCTA TAGCTCTTCA CCGTCTCTAC TTTCTTCCTT CTAAGAGATC
    CCTCGAACCT CGAGGATCCG ACCCCGCAG GGTCTACAAC ACCTTGACAG GGACCTAGAT ATCGAGAAGT GGCAGAGATG AAAGAAGGAA GATTCTCTAG

101 CTGAAACCTC TGTCATGGAA AAGTACCACG TGTTGGAGAT GATTGGAGAA GGCTCTTTTG GGAGGGTGTA CAAGGGTCGA AGAAAATACA GTGCTCAGGT
    GACTTTGGAG ACAGTACCTT TTCATGGTGC ACAACCTCTA CTAACCTCTT CCGAGAAAAC CCTCCCACAT GTTCCCAGCT TCTTTTATGT CACGAGTCCA
  1                      M  E  K  Y  H  V  L  E  M  I  G  E  G  S  F  G  R  V  Y  K  G  R  R  K  Y  S  A  Q  V
                         ^Translation ATG starts here 201 CGTGGCCCTG AAGTTCATCC CAAAATTGGG GCGCTCAGAG AAGGAGCTGA ACGAGAGATT GAAATAATGC GGGGTCTGCG GCATCCCAAC
    GCACCGGGAC TTCAAGTAGG GTTTTAACCC CGCGAGTCTC TTCCTCGACT TGCTCTCTAA CTTTATTACG CCCCAGACGC CGTAGGGTTG
 30  V  A  L  K  F  I  P  K  L  G  R  S  E  K  E  L  R  N  L  Q  R  E  I  M  R  G  L  R  H  P  N 301 ATTGTGCATA TGCTTGACAG CTTTGAAACT GATAAAGAGG TGGTGGTGGT GCTGAGGGAG GCTGAGGGAG AGCTCTTTCA GATCCTAGAA GATGACGAA
    TAACACGTAT ACGAACTGTC GAAACTTTGA CTATTTCTCC ACCACCACCA CGACTCCCTC TCGAGAAAGT TCTAGGATCTT CTACTGCCTT
 63  I  V  H  M  L  D  S  F  E  T  D  K  E  V  V  V  V  T  D  Y  A  E  G  E  L  F  Q  I  L  E  D  D  G  K 401 AACTTCCTGA AGACCAGGTT CAGGCCATTG CTGCCCAGTT GGTGTCAGCC CTGTACTATC TGCATTCCCA CCGCATCCTA CACCGAGATA TGAAGCCTCA
    TTGAAGGACT TCTGGTCCAA GTCCGGTAAC GACGGGTCAA CCACAGTCGG GACATGATAG GACATAAGGT GGCGTAGGAT GTGGCTCTAT ACTTCGGAGT
 97  L  P  E  D  Q  V  Q  A  I  A  A  Q  L  V  S  A  L  Y  Y  L  H  S  H  R  I  L  H  R  D  M  K  P  Q 501 GAACATCCTC CTCGCCAAGG GTGGTGGCAT CAAGCTCTGT GACTTTGGAT TTGCCCGGGC TATGAGCACC AATACAATGG TGCTGACATC CATCAAAGGC
    CTTGTAGGAG GAGCCGGTTCC CACCACCGTA GTTCGAGACA CTGAAACCTA AACGGGCCCG ATACTCGTGG TTATGTTACC ACGACTGTAG GTAGTTTCCG
130  N  I  L  L  A  K  G  G  G  I  K  L  C  D  F  G  F  A  R  A  M  S  T  N  T  M  V  L  T  S  I  K  G 601 ACACCACTCT ATATGTCTCC AGAGCTGGTG GAGGAGCGAC CATACGACCA CTCTGGTCTG TTGGCTGCAT ACTATATGAA CTGGCAGTAG
    TGTGGTGAGA TATACAGAGG TCTCGACCAC CTCCTCGCTG GTGTCGCCTG GAGACCAGAC AACCGACGTA TGATATACTT GACCGTCATC
163  T  P  L  Y  M  S  P  E  L  V  E  E  R  P  Y  D  H  T  A  D  L  W  S  V  G  C  I  L  Y  E  L  A  V  G
```

FIG. 5A

```
701  GCACCCCTCC CTTCTATGCT ACAAGCATCT TTCAGCTGGT CAGCCTCATT CTCAAGGACC CTGTGCGCTG GCCCTCAACC ATCAGTCCCT GCTTTAAGAA
     CGTGGGGAGG GAAGATACGA TGTTCGTAGA AAGTCGACCA GTCGGAGTAA GAGTTCCTGG GACACGCGAC CGGGAGTTGG TAGTCAGGGA CGAAATTCTT
197   T   P   P   F   Y   A   T   S   I   F   Q   L   V   S   L   I   L   K   D   P   V   R   W   P   S   T   I   S   P   C   F   K   N

801  CTTCCTGCAG GGACTGCTCA CCAAAGACCC ACGGCAGCGA CTGTCCTGGC CAGACCTCTT ATATCACCCC TTTATTGCTG GTCATGTCAC CATAATAACT
     GAAGGACGTC CCTGACGAGT GGTTTCTGGG TGCCGTCGCT GACAGGACCG GTCTGGAGAA TATAGTGGGG AAATAACGAC CAGTACAGTG GTATTATTGA
230   F   L   Q   G   L   L   T   K   D   P   R   Q   R   L   S   W   P   D   L   L   Y   H   P   F   I   A   G   H   V   T   I   I   T

901  GAGCCAGCAG GCCCAGATTT GGGGACCCCA TTCACCAGCC GCCTAAAGGG AGAACTTCAG GTCCTAAAGG ACGAACAGGC CCATCGGTTG GCCCCCAAGG
     CTCGGTCGTC CGGGTCTAAA CCCCTGGGGT AAGTGGTCGG CGGATGGGGG TCTTGAAGTC CAGGATTTCC TGCTTGTCCG GGTAGCCAAC CGGGGGTTCC
263   E   P   A   G   P   D   L   G   T   P   F   T   S   R   L   P   P   E   L   Q   V   L   K   D   E   Q   A   H   R   L   A   P   K   G

1001 GTAATCAGTC ACTCAGGCCT ATAAACGCAT GGCTGAGGAG GCCATGCAGA AGAAACATCA GAACACAGGA CCTGCCCTTG AGCAAGAGGA CTCAGAATTG
     CATTAGTCAG TGAGTCCGGA TATTTGCGTA CCGACTCCTC CGGTACGTCT TCTTTGTAGT CTTGTGTCCT GGACGGGAAC TCGTTCTCCT GAGTCTTAAC
297   N   Q   S   R   I   L   T   Q   A   Y   K   R   M   A   E   E   A   M   Q   K   K   H   Q   N   T   G   P   A   L   E   Q   E   D   S   E   L

1101 CAAGAGCAGC AAGGTGGCTC CTGGCACAGC CCCTCTGCCC AGACTCGGGG GGAATCAAGC CCACTCCTCA GGATCTTAGC CTCCTGGCCG GGATCTTAGC
     GTTCTCGTCG TTCCACCGAG GACCGTGTCG GGAGACGGG  TCTGAGCCCC CCTTAGTTCG GGTGAGGAGT CCTAGTTCG  GAGGACCGGC CCTAGAATCG GAGTCTTAAC
330   K   T   S   K   V   A   P   G   T   A   P   L   P   R   L   G   A   T   P   Q   E   S   S   L   L   A   G   I   L   A   S   E   L

1201 AAGAGACAGC GGGCTAAATC AGGGACTGGA GAGGTGCCCT CTGCACCTCG GGAAAACCGG ATTGTGAACG AGCATTCCCA GAGGAGAGGC
     TTCTCGTCGA CCCGATTTAG TCCCTGACCT CTCCACGGGA GACGTGGAGC CCTTTTGGCC TAACACTTGC TCGTAAGGGT CTCCTCTCCG
363   K   S   S   W   A   K   S   G   T   G   E   V   P   S   A   P   R   E   N   R   T   T   P   D   C   E   R   A   F   P   E   E   R   P

1301 CAGAGGTGCT GGGCCAGCGA GCCACTGATG TAGTGGACCT GGAAAATGAG GAGCCAGACA GTCGGTCTGT CACTGTTACT CTGCTAGAGA CCACTGAGCC
     GTCTCCACGA CCCGGTCGCT CGTGACTAC  ATCACCTGGA CCTTTTACTC CTCGGTCTGT CAGCCAGACA GTGACAATGA CACTGTTACT CACCGTCTGT GGTGACTCGG
397   E   V   L   G   Q   R   S   T   D   V   V   D   L   E   N   E   E   P   D   S   D   N   E   W   Q   H   L   L   E   T   T   E   P

1401 TGTGCCTATT CAACTGAAGG CTTGCTTGCT CTCCTCTCAC CTTGCTCTGT AATCCTGACT TCTGCCAGCG CATCCAGAGT CAGCTGCATG AAGCTGGAGG GCAGATCCTG
     ACACGGATAA GTTGACTTCC GAACGAGAGTG GAGGAGAGTG GAACGACACA TTAGGACTGA AGACGGTCGC GTAGGTCTCA GTCGACGTAC TTCGACCTCC CGTCTAGGAC
430   V   P   I   Q   L   K   A   P   L   T   L   L   C   N   P   D   F   C   Q   R   I   Q   S   Q   L   H   E   A   G   G   Q   I   L

1501 AAAGGCATCT TGGAGGGTGC TTTCCACATC CTGCCTGCAT TCCGGGTCCT GAGCAGTCTT CTCTCCAGCA GGCCCAGGA  CTCGTCAGAA CGTCACTAAG GCAGTGATTC TGTTGCCTTG TATTCCTTCT
     TTTCCGTAGA ACCTCCCACG AAAGGTGTAG GACGGACGTA AGGCCCAGGA CTCGTCAGAA GAGAGGTCGT CCGGGTCCT  GAGCAGTCTC TTCGACTCG  ACAACGAAC ATAAGGAAGA
463   K   G   I   L   E   G   A   S   H   I   L   P   A   F   R   V   L   S   S   L   L   S   S   C   S   D   S   V   A   L   Y   S   F   C
```

```
2501 ACTTCCCTCTC CCTTCTGTC TTTCGGCTCC AAAACCTGCC TTGTGGAATG GAGAAGCTAG GCAGTGACGT TGCTACTCTC TTTACCCATT CGCATGTCGT
     TGAAGGAGAG GGAAGAACAG AAAGCCGAGG TTTTGGACGG AACACCTTAC CTCTTCGATC CGTCACTGCA ACGATGAGAG AAATGGGTAA GCGTACAGCA
135    F  L  S    L  L  V    F  R  L  Q    N  L  P    C  G  M    E  K  L  G    S  D  V    A  T  L    F  T  H  S    H  V  V

2601 CTCTCTTGTG AGTGCAGCAG CCTGTCTATT GGGACAGCTT GGTCAGCAAG GGGTGACCTT TGACCTCCAG CCCATGAAT GGATGGCTGC AGCCACACAT
     GAGAGAACAC TCACGTCGTC GGACAGATAA CCCTGTCGAA CCAGTCGTTC CCCACTGGAA ACTGGAGGTC GGGTACCTTA CCTACCGACG TCGGTGTGTA
168    S  L  V    S  A  A  A    C  L  L    G  Q  L    G  Q  Q  G    V  T  F    D  L  Q    P  M  E  W    M  A  A    T  H

2701 GCCTTGTCTG CCCCTGCAGA GCTCCTCACT GAGGTACAGA TGGATCTTGG GATGGATGGG AAGTAAAGAG AGAGGAACTG GGCATTTTGG GGAGCCTCTG
     CGGAACAGAC GGGGACGTCT CGAGGAGTGA CTCCATGTCT ACCTAGAACC CTACCTACCC TTCATTTCTC TCTCCTTGAC CCGTAAAACC CCTCGGAGAC
201    A  L  S  A    P  A  E    L  L  T    E  V  Q  M    D  L  G    M  D  G    K  Q

2801 GACCAGAGGA ATGAAGAAGC AACCCACAGC CTTCCCTCTC AAGCTACTGT GCCTGTGATA TTTCCCGCCT GCCCTGGAAC CCCTCAGTA CTGACCCTTT
     CTGGTCTCCT TACTTCTTCG TTGGGTGTCG GAAGGGAGAG TTCGATGACA CGGACACTAT CGGAACCTTG AAGGGGCGA CGGGAGTCAT GACTGGGAAA

2901 GAAGGAAACC ATTCGCTGCG TCCAGTGGGA GATAAAATGA ATTCCCTGGG CATACACATG AGTTGTGAGG TCAGAGGGTT
     CTTCCTTTGG TAAGCGACGC AGGTCACCCT CTATTTTACT TAAGGGACCC GTATGTGTAC TCAACACTCC AGTCTCCCAA

3001 AAGGTTTGAT AAGAAAATGA AATAAGACGA CAGGGAAATA CTAGGTGGGA AAGCGGAAGG AATTATTTCT GGGACTTCCT TTACTTGTAA GTCAGGGACA
     TTCCAAACTA TCTTTTTACT TTATTCTGCT GTCCCTTTAT GATCCACCCT TTCGCCTTCC TTAATAAAGA CCCTGAAGGA AATGAACATT CAGTCCCTGT

3101 GGAATGAATA AAAGCATTTG GATTCCTGAC CAGGGACTG TTCTGTCTTT CCCCCCGCCC TCTTTCACTT TTATCTCTAG CAGGGAAGG CTAGCCTAAT CAGGGATATG
     CCTTACTTAT TTTCGTAAAC CTAAGGACTG AAGACAGAAA GGGGGGCGGG AGAAAGTGAA AATAGAGATC GTCCCCTTCC GATCGGATTA GTCCCTATAC

3201 TCCAGTTCAG AAATGTGGAC CGTTTTGTGT CACCGCTTCT GAGGCTCCCC CCATGGTCCT CTGCACAGGA GAGGAGGCAT CTGCACAGGA AGGGGAGCTT TCGCTATCCA
     AGTCAAGTC TTTACACCTG GCAAAACACA GTGGCGAAGA CTCCGAGGGG GGTACCAGGA GACGTGTCCT CTCCTCCGTA GACGTGTCCT TCCCCTCGAA AGCGATAGGT

3301 GTCCACCAAG CCCTGAGCCA GACTGGACAC TGATTTCTCC CCAGGGCATG GCAGCCCTGC TGAGCCTGGC CATGGCCACC TTTACCAGG AGCCCCAGTT
     CAGGTGGTTC GGGACTCGGT CTGACCTGTG ACTAAAGAGG GGTCCCGTAC CGTCGGGACG GTACCGGTGG AAATGGGTCC TCGGGGTCAA

3401 ATGCCTGAGC TGCCTGTCCC AGCATGGAAG TCCATCCTGA TATCCTCATG TCCTTCCCAGC AGCATCTGCT TTCCCTGAATC AACTGCGCCA GGCGCCTCAT
     TACGGACTCG ACGGACAGGG TCGTACCTTC AGGTAGGACT ATAGGAGTAC AGGGGTCG AACGGGGTCG TTGACGACTAG CCGCGGAGTA

3501 GGGTCTGAGT TTCTCCCTGT CGTGGTGCTC TCTGTCTGCC AGCTCCTTTG CTTCCCCTTT GCGCTGGACA TGGATGCTGA CCTCCTTATA GGTGTCTTGG
     CCCAGACTCA AAGAGGGACA GCACCACGAG AGACAGACGG TCGAGGAAAC TCGAGGAAAC CGCGACCTGT ACCTACGACT GGAGGAATAT CCACAGAACC
```

FIG. 5D

```
3601  CCGACCTCAG  GGACTCAGAA  GTTGCAGCCC  ATCTGCTGCA  GGTCTGCTGC  TACCATCTTC  CGTTGATGCA  AGTGGAGCTG  CCCATCAGCC  TTCTCACACG
      GGCTGGAGTC  CCTGAGTCTT  CAACGTCGGG  TAGACGACGT  CCAGACGACG  ATGGTAGAAG  GCAACTACGT  TCACCTCGAC  GGGTAGTCGG  AAGAGTGTGC

3701  CCTGGCCCTC  ATGGATCCCA  CCTCTCTCAA  CCAGTTTGTG  AACACAGTGT  CTGCCTCCCC  TAGAACCATC  GTCTCGTTTC  TCTCAGTTGC  CCTCCTGAGT
      GGACCGGGAG  TACCTAGGGT  GGAGAGAGTT  GGTCAAACAC  TTGTGTCACA  GACGGAGGGG  ATCTTGGTAG  CAGAGCAAAG  AGAGTCAACG  GGAGGACTCA

3801  GACCAGCCAC  TGTTGACCTC  CGACCTTCTC  CGGGTCCTG   CAGGGTCCTG  TCTCCCAGCC  ACTTGTCCTT  TATCCAAGAG  CTTCTGGCTG
      CTGGTCGGTG  ACAACTGGAG  GCTGGAAGAG  AGAGACGACC  GTCCCAGGAC  AGAGGGTCGG  TGAACAGGAA  ATAGGTTCTC  GAAGACCGAC

3901  GCTCTGATGA  ATCCTATCGG  CCCCTGCGCA  GCCTCCCTGG  CCACCCAGAG  AATTCTGTGC  GGGCACACAC  TTATAGGCTC  CTGGGACACT  TGCTCCAACA
      CGAGACTACT  TAGGATAGCC  GGGGACGCGT  CGGAGGGACC  GGTGGGTCTC  TTAAGACACG  CCCGTGTGTG  AATATCCGAG  GACCCTGTGA  ACGAGGTTGT

4001  CAGCATGGCC  CTGCGTGGGG  CACTGCAGAG  CCAGTCTCGA  CTGCTCAGCC  TTCTGCTGCT  TGGGCTTGGA  GACAAGGATC  CTGTTGTGCG  GTGCAGTGCC
      GTCGTACCGG  GACGCACCCC  GTGACGTCTC  GGTCAGACGT  GACGAGTCGG  AAGACGACGA  ACCCGAACCT  CTGTTCCTAG  GACAACACGC  CACGTCACGG

4101  AGCTTTGCTG  TGGGCAATGC  AGCCTACCAG  GCTGGTCCTC  TGGGACCTGC  CCTGGCAGCT  GCAGTGCCCA  GTATGACCCA  GCTGCTTGGA  GATCCTCAGG
      TCGAAACGAC  ACCCGTTACG  TCGGATGGTC  CGACCAGGAG  ACCCTGGACG  GGACCGTCGA  CGTCACGGGT  CATACTGGGT  CGACGAACCT  CTAGGAGTCC

4201  CTGGTATCCG  GCGCAATGTT  GCATCAGCTC  TGGGCAACTT  GGGACCTGAA  CCCTCCGGAG  GCCCTCATTG  ACAGTGCTGT  ACAGTGCGAA  GGCTCCTAGA
      GACCATAGGC  CGCGTTACAA  CGTAGTCGAG  ACCCGTTGAA  CCCTGGACTT  GGGAGGCCTC  CGGGAGTAAC  TGTCACGCTT  TCCTCGACAA  CCGAGGATCT

4301  AATGGCATGT  GGAGACCCCC  AGCCAAATGT  GAAGGAGGCT  TCTCTCTGGGA  GCCACACAGC  CCTGCAACAG  AGTCCTAGGC  TCCATCAGGT  ACTGGTGTCC
      TTACCGTACA  CCTCTGGGGG  TCGGTTTACA  CTTCCTCCGA  AGAGACCCT   CGGTGTGTCG  GGACGTTGTC  TCAGGATCCG  AGGTAGTCCA  TGACCACAGG

4401  CTGGGTGCCA  GTGAGAAACT  ATCCTTGCTC  TCTCTGGGGA  ATCAGTCACT  GCCACACTACT  CCTGCCCTGC  CTGCCCTCTGC  CAGCTCTTTC  AGGAAACTCA
      GACCCACGGT  CACTCTTTGA  TAGGAACGAG  AGAGACCCCT  TAGTCAGTGA  CGGTGTGATGA  CGGGAGACG   GACGGGAGACG  GTCGAGAAAG  TCCTTTGAGT

4501  TTCACCTCCT  GAGGCCAGCC  CATAGCATGT  GATTCCAGAT  CTAAGGTCTA  AGGACGCCAG  CAGCCTCCAA  CTTTGGTTGC  CAGCTCTTTC  TTATTCTACT
      AAGTGGAGGA  CTCCGGTCGG  GTATCGTACA  CTAAGGTCTA  GATTCCAGAT  TCCTGCGGTC  GTCGGAGGTT  GAAACCAACG  GTCGAGAAAG  AATAAGATGA

4601  CCAACTCAAC  TGAGAGCTAA  AGAGACTAGA  AAAGAGATAA  GCTGCCAACT  CAACTGAGAA  CAAGAAACTA  GAAGAGATTT  ATATATAAAG  CTTCTTCCTT
      GGTTGAGTTG  ACTCTCGATT  TCTCTGATCT  TTTCTCTATT  CGACGGTTGA  GTTGACTCTT  GTTCTTTGAT  CTTCTCTAAA  TATATATTTC  GAAGAAGAA
```

FIG. 5E

```
4701 CTCCCAGATG CAGGATGTTT TCAACCAGTA AATTTTATTG CTGTTGGTGC CAGAGAAGAG TCCTTTCTTC TCTACATCCA GGGGCCTTTT CTCCAATAAT
     GAGGGTCTAC GTCCTACAAA AGTTGGTCAT TTAAAATAAC GACAACCACG GTCTCTTCTC AGGAAAGAAG AGATGTAGGT CCCCGAAAA GAGGTTATTA

4801 GTGCCTTTAA CTCTAGGGAC CTGCCTCACG GACCTTAGGG AAAAACCTCA ACCTGAAAGA TCTCTTCCTT TCTGGAGCTC CTTTAATCTT CCCAGCAGGT
     CACGGAAATT GAGATCCCTG GACGGAGTGC CTGGAATCCC TTTTTGGAGT TGGACTTTCT AGAGAAGGAA AGACCTCGAG GAAATTAGAA GGGTCGTCCA

4901 TTTTGCCTTA GACGTGCTGG CCCCAGGACA GTGATGAAGA CAGAGCCTGT CTCAGCTCTA GGCTGTGGGG ATCAATGCCA TCAGTCCCTG TTATTGAGGG
     AAAACGGAAT CTGCACGACC GGGGTCCTGT CACTACTTCT GTCTCGGACA GAGTCGAGAT CCGACACCCC TAGTTACGGT AGTCAGGGAC AATAACTCCC

5001 ATTATCCCTT AGCCAACATT CCTATCTGTG GGTGGGCGTG GAGAGTGTAT CTTTTTTTGG GGTGTGTGTG TATATGTGTG TGTGTGTGTT
     TAATAGGGAA TCGGTTGTAA GGATAGACAT CCACCCGCAC CTCTCACATA GAAAAAAACC CCACACACAC ATATACACAC ACACACACAA

5101 TAATAGTTCT GTTTGTAAAC TCTTTTAATA AAAGTTGTGC CTCACCATAC TTGAAGCTCC CAGGACAAGG GTTGAGAGGC TCAACCCCTC TTTCAGCTTC
     ATTATCAAGA CAAACATTTG AGAAAATTAT TTTCAACACG GAGTGGTATG AACTTCGAGG GTCCTGTTCC CAACTCTCCG AGTTGGGGAG AAAGTCGAAG

5201 TATGTGGTGT TGGAGGTGCT GGTATCGTGT TCACACAAAA AAAAAAAAAA AA
     ATACACCACA ACCTCCACGA CCATAGCACA AGTGTGTTTT TTTTTTTTTT TT
```

FIG. 5F

FUSED

FIELD OF THE INVENTION

The present invention relates generally to signaling molecules, specifically to signaling and mediator molecules in the hedgehog (Hh) cascade which are involved in cell proliferation and differentiation.

BACKGROUND OF THE INVENTION

Development of multicellular organisms depends, at least in part, on mechanisms which specify, direct or maintain positional information to pattern cells, tissues, or organs. Various secreted signaling molecules, such as members of the transforming growth factor-beta (TGF-β), Wnt, fibroblast growth factors and hedgehog families have been associated with patterning activity of different cells and structures in Drosophila as well as in vertebrates. Perrimon, Cell: 80: 517–520 (1995).

Hedgehog (Hh) was first identified as a segment-polarity gene by a genetic screen in *Drosophila melanogaster,* Nusslein-Volhard et al, Roux. *Arch. Dev. Biol.* 193: 267–282 (1984), that plays a wide variety of developmental functions. Perrimon, supra. Although only one Drosophila Hh gene has been identified, three mammalian Hh homologues have been isolated: Sonic Hh (SHh), Desert Hh (DHh) and Indian Hh (IHh), Echelard et al, Cell 75: 1417–30 (1993); Riddle et al, Cell 75: 1401–16 (1993). SHh is expressed at high level in the notochord and floor plate of developing vertebrate embryos. In vitro explant assays as well as ectopic expression of SHh in transgenic animals show that SHh plays a key role in neuronal tube patterning, Echelard et al., supra., Krauss et al., Cell 75, 1431–44 (1993), Riddle et al, *Cell* 75: 1401–16 (1993), Roelink et al, *Cell* 81: 445–55 (1995). In vitro explant assays as well as ectopic expression of SHh in transgenic animals show that SHh plays a key role in neural tube patterning, Echelard et al. (1993), supra.; Ericson et al., *Cell* 81: 747–56 (1995); Marti et al, *Nature* 375: 322–5 (1995); Roelink et al. (1995), supra; Hynes et al, *Neuron* 19: 15–26 (1997). Hh also plays a role in the development of limbs (Krauss et al, Cell 75: 1431–44 (1993); Laufer et al, *Cell* 79, 993–1003 (1994)), somites (Fan and Tessier-Lavigne, Cell 79 1175–86 (1994); Johnson et al, *Cell* 79: 1165–73 (1994)), lungs (Bellusci et al., Develop. 124: 53–63 (1997) and skin (Oro et al, *Science* 276: 817–21 (1997). Likewise, IHh and DHh are involved in bone, gut and germinal cell development, Apelqvist et al., Curr. *Biol* 7: 801–4 (1997); Bellusci et al., *Development* 124: 53–63 (1997); Bitgood et al., Curr. *Biol.* 6: 298–304 (1996); Roberts et al., *Development* 121: 3163–74 (1995). SHh knockout mice further strengthened the notion that SHh is critical to many aspect of vertebrate development, Chiang et al., Nature 383: 407–13 (1996). These mice show defects in midline structures such as the notochord and the floor plate, absence of ventral cell types in neural tube, absence of distal limb structures, cyclopia, and absence of the spinal column and most of the ribs.

At the cell surface, the Hh signals is thought to be relayed by the 12 transmembrane domain protein Patched (Ptch) [Hooper and Scott, *Cell* 59: 751–65 (1989); Nakano et al., *Nature* 341: 508–13 (1989)] and the G-protein coupled like receptor Smoothened (Smo) [Alcedo et al., *Cell* 86: 221–232 (1996); van den Heuvel and Ingham, Nature 382: 547–551 (1996)]. Both genetic and biochemical evidence support a receptor model where Ptch and Smo are part of a multicomponent receptor complex, Chen and Struhl, *Cell* 87: 553–63 (1996); Marigo et al., *Nature* 384: 176–9 (1996); Stone et al., *Nature* 384: 129–34 (1996). Upon binding of Hh to Ptch, the normal inhibitory effect of Ptch on Smo is relieved, allowing Smo to transduce the Hh signal across the plasma membrane. Loss of function mutations in the Ptch gene have been identified in patients with the basal cell nevus syndrome (BCNS), a hereditary disease characterized by multiple basal cell carcinomas (BCCs). Disfunctional Ptch gene mutations have also been associated with a large percentage of sporadic basal cell carcinoma tumors, Chidambaram et al., *Cancer Research* 56: 4599–601 (1996); Gailani et al., *Nature Genet.* 14: 78–81 (1996); Hahn et al., *Cell* 85: 841–51 (1996); Johnson et al., Science 272: 1668–71 (1996); Unden et al., *Cancer Res.* 56: 4562–5 (1996); Wicking et al., *Am. J. Hum. Genet.* 60: 21–6 (1997). Loss of Ptch function is thought to cause an uncontrolled Smo signaling in basal cell carcinoma. Similarly, activating Smo mutations have been identified in sporatic BCC tumors (Xie et al., *Nature* 391: 90–2 (1998)), emphasizing the role of Smo as the signaling subunit in the receptor complex for SHh. However, the exact mechanism by which Ptch controls Smo activity still has yet to be clarified and the signaling mechanisms by which the Hh signal is transmitted from the receptor to downstream targets also remain to be elucidated. Genetic epistatic analysis in Drosophila has identified several segment-polarity genes which appear to function as components of the Hh signal transduction pathway, Ingham, *Curr. Opin. Genet. Dev.* 5: 492–8 (1995); Perrimon, supra. These include a kinesin-like molecule, Costal-2 (Cos-2) [Robbins et al., *Cell* 90: 225–34 (1997); Sisson et al, *Cell* 90: 235–45 (1997)], a protein designated fused [Preat et al., *Genetics* 135: 1047–62 (1993); Therond et al., *Proc. Natl Acad Sci. USA* 93: 4224–8 (1996)], a novel molecule with unknown function designated Suppressor offused [Pham et al., Genetics 140: 587–98 (1995); Preat, *Genetics* 132: 725–36 (1992)] and a zinc finger protein Ci. [Alexandre et al., *Genes Dev.* 10: 2003–13 (1996); Dominguez et al., *Science* 272: 1621–5 (1996); Orenic et al, *Genes Dev.* 4: 1053–67 (1990)]. Additional elements implicated in Hh signaling include the transcription factor CBP [Akimaru et al., *Nature* 386: 735–738 (1997)], the negative regulator slimb [Jiang and Struhl, *Nature* 391: 493–496 (1998)] and the SHh response element COUP-TFII [Krishnan et al., *Science* 278: 1947–1950 (1997)].

Mutants in Cos-2 are embryonicly lethal and display a phenotype similar to Hh over expression, including duplications of the central component of each segment and expansion domain of Hh responsive genes. In contrast, mutant embryos for fused and Ci show a phenotype similar to Hh loss of function including deletion of the posterior part of each segment and replacement of a mirror-like image duplication of the anterior part or each segment and replacement of a mirror-like duplication of the anterior part, Busson et al., Roux. Arch. Dev. *Biol.* 197: 221–230 (1988). Molecular characterizations of Ci suggested that it is a transcription factor which directly activates Hh responsive genes such as *Wingless* and *Dpp,* Alexandre et al., (1996) supra, Dominguez et al., (1996) supra. Likewise, molecular analysis offused reveals that it is structurally related to serine threonine kinases and that both intact N-terminal kinase domain and a C-terminal regulatory region are required for its proper function, Preat et al., *Nature* 347: 87–9 (1990); Robbins et al., (1997), supra; Therond et al., *Proc. Natl. Acad. Sci. USA* 93: 4224–8 (1996). Consistent with the putative opposing functions of Cos-2 andffused,fused mutations are suppressed by Cos-2 mutants and also by Suppressor of fused mutants, Preat et al., Genetics 135: 1047–62 (1993). However, whereas fused null mutations and N-terminal kinase domain mutations can be fully suppressed by Suppressor of fused mutations, C-terminus mutations of fused display a strong Cos-2 phenotype in a Suppressor of fused background. This suggests that the fused kinase domain can act as a constitutive activator of SHh signaling when Suppressor of Fused is not present. Recent studies have shown that the 92 kDa Drosophila fused, Cos-2 and Ci are present in a microtubule associated multiprotein complex and that Hh signaling leads to dissociation of this complex from microtubules, Robbins et al, *Cell* 90: 225–34 (1997); Sisson et al., *Cell* 90: 235–45 (1997). Both _fused and Cos-2 become phosphorylated in response to Hh treatment, Robbins et al., *supra;* Therond et al., *Genetics* 142: 1181–98 (1996), but the kinase(s) responsible for this activity(ies) remain to be characterized. To date, the only known vertebrate homologues for these components are members of the Gli protein family (e.g., Gli-1, Gli-2 and Gli-3). These are zinc finger putative transcription factors that are structurally related to Ci. Among these, Gli-1 was shown to be a candidate mediator of the SHh signal [Hynes et al., *Neuron* 15: 35–44 (1995), Lee et al., *Development* 124: 2537–52 (1997); Alexandre et al., *Genes Dev.* 10: 2003–13 (1996)] suggesting that the mechanism of gene activation in response to Hh may be conserved between fly and vertebrates. To determine whether other signaling components in the Hh cascade are evolutionarily conserved and to examine the function of fused in the Hh signaling cascade on the biochemical level, Applicants have isolated and characterized the human fused cDNA. Tissue distribution on the mouse indicates that fused is expressed in SHh responsive tissues. Biochemical studies demonstrate that fused is a functional kinase. Functional studies provide evidence that fused is an activator of Gli and that a dominant negative form of fused is capable of blocking SHh signaling in Xenopus embryos. Together this data demonstrated that fused is directly involved in Hh signaling.

Applicants have identified a cDNA encoding a human fused (hfused) polypeptide and thus have provided for the first time a vertebrate fused molecule.

SUMMARY OF THE INVENTION

In one embodiment, the invention provides an isolated nucleic acid molecule having at least about 80% sequence identity to (a) a DNA molecule encoding a fused polypeptide comprising the sequence of amino acids 1 to 260 of FIG. 1 (SEQ ID NO:24), or (b) the complement of the DNA molecule of (a); and encoding a polypeptide having fused biological activity. The sequence identity preferably is about 85%, more preferably about 90%, most preferably about 95%. In one aspect, the isolated nucleic acid has at least about 80%, preferably at least about 85%, more preferably at least about 90%, and most preferably at least about 95% sequence identity with a polypeptide having amino acid residues 1 to about 1315 of FIG. 1 (SEQ ID NO:2). Preferably, the highest degree of sequence identity occurs within the kinase domain (amino acids 1 to about 260 of FIG. 1 (SEQ ID NO:2)). Especially preferred are those nucleic acid molecule containing a coding sequence for a lysine at amino acid position 33. In a further aspect, the isolated nucleic acid molecule comprises DNA encoding a human fused polypeptide having amino acid residues 1 to about 260 of (SEQ ID NO:2 as shown in FIG. 1. In yet another aspect, the invention provides for an isolated nucleic acid comprising DNA having at least a 95% sequence identity to (a) a DNA molecule encoding the same mature polypeptide encoded by the cDNA in ATCC Deposit No. 209637 (designation: pRK5tkneo.hFused-1272), alternatively the coding sequence of clone pRK5tkneo.hFused-1272, deposited under accession number ATCC 209637. In a still further aspect, the invention provides for a nucleic acid comprising human fused encoding sequence of the cDNA in ATCC deposit No. 209637 (designation: pRK5tkneo.hFused-1272) or a sequence which hybridizes thereto under stringent conditions.

In another embodiment, the invention provides a vector comprising DNA encoding a vertebrateflsed polypeptide. A host cell comprising such a vector is also provided. By way of example, the host cells may be mammalian cells, (e.g. CHO cells), prokaryotic cells (e.g., E. coli) or yeast cells (e.g., *Saccharomyces cerevisiae*). A process for producing vertebrate fused polypeptides is further provided and comprises culturing host cells under conditions suitable for expression of vertebratefused and recovering the same from the cell culture.

In yet another embodiment, the invention provides an isolated vertebrate fised polypeptide. In particular, the invention provides isolated native sequence vertebrate fused polypeptide, which in one embodiment is a human fused including an amino acid sequence comprising residues 1 to about 1315 of (SEQ ID NO:2) as shown in FIG. 1. Human and other native vertebrate fused polypeptides with or without the initiating methionine are specifically included. Alternatively, the invention provides a vertebrate fused polypeptide encoded by the nucleic acid deposited under accession number ATCC 209637.

In yet another embodiment, the invention provides chimeric molecules comprising a vertebrate fused polypeptide fused to a heterologous polypeptide or amino acid sequence. An example of such a chimeric molecule comprises a vertebrate fused polypeptide fused to an epitope tag sequence or a constant region of an immunoglobulin.

In yet another embodiment, the invention provides an expressed sequence tag (EST) comprising the nucleotide sequences identified in FIG. 2 as 2515662 (SEQ ID NO:3).

In yet another embodiment, the invention provides for compounds and methods for developing antagonists against and agonist promoting fused modulation of Hedgehog signaling. In particular, an antagonist of vertebrate fused which blocks, prevents, inhibits and/or neutralized the normal functioning of fused in SH signaling pathway, including both small bioorganic molecules and antisense nucleotides.

In yet another embodiment, the invention provides for alternatively spliced variants of human fuised. In still yet a further embodiment, the invention provides a method of screening or assaying for identifying molecules that modulate the fused activation of hedgehog signaling. Preferably, the molecules either prevent interaction offused with its associative complexing proteins or prevent or inhibit dissociation of complexes. The assay comprises the incubation of a mixture comprising fused and a substrate (e.g., Gli, COUP-TFII, slimb, CBP, MBP) with a candidate molecule and detection of the ability of the candidate molecule to modulate fused phosphorylation of its substrate. The screened molecules preferably are small molecule drug candidates. In particular, the method relates to a technique for screening for antagonists or agonists of fused biological activity comprising:

(a) exposing the fused expressing target cells in culture to a candidate compound; and (b) analyzing cell lysates to asses the level and/or identity of phosphorylation; or (c) scoring phenotypic or functional changes in treated cells; and comparing the results to control cells which were not exposed to the candidate compound. In yet another embodiment, the method relates to a technique of diagnosing to determine whether a particular disorder is modulated by hedgehog signaling, comprising:
(a) culturing test cells or tissues;
(b) administering a compound which can inhibitfitsed modulated hedgehog signaling; and
(c) measuring the degree of kinase attenuation on the fised substrate in cell lysates or hedgehog mediated phenotypic effects in the test cells.

BRIEF DESCRIPTION OF THE DRAWINGS

FIGS. 1A–1F show the nucleotide (SEQ ID NO:1) and derived amino acid (SEQ ID NO:2) sequence of a native sequence of human fused polypeptide. Included are the kinase domain (residues 1 to about 260 (SEQ ID NO:24)) and the ATP binding site at about amino acid position 33.

FIG. 2 shows the EST 2515662 (SEQ ID NO:3) that was used in the cloning of the human full-length fused sequence.

FIGS. 3A–3E show a comparison between human and Drosophila fused (SEQ ID NOS: 2 and 23, respectively). Gaps introduced for optimal alignment are indicated by dashes. Identical amino acids are boxed. The lysine residue mutated infused-DN (dominant negative, lysine at amino acid position 33) is shown with a star.

FIGS. 4A–4F show the sequence of DNA28495 (SEQ ID NOS:4, 5 and 21) that was an incorrectly spliced variant of human fuised isolated from a fetal lung library. This clone contains a potential initiation methionine at position 116 followed by an open reading frame of 1944 bp. A second open reading frame is present from about position 2295 to 4349. There is one nucleotide difference between clone DNA28495 (SEQ ID NO:4) and clone DNA28494 (SEQ ID NO:6) located in the first ORF at position 1863 of clone DNA28495 (SEQ ID NO:4) (A vs. G) which changes the coding sequence from an Gln to a Arg at position 583. The first open reading frame of DNA28494 (SEQ ID NO:6) starts at residue 115 and is followed by a 630 amino acid long open reading frame.

FIGS. 5A–5F show the sequence of DNA28494 (SEQ ID NOS:6, 7 and 22) that was another incorrectly spliced variant of human fused isolated from a fetal lung library.

FIG. 8A, 1.0 mm; FIG. 8B, 1.62 mm; FIG. 8C, 0.14 mm; FIG. 8D, 0.17 mm; FIG. 8E, 2.0 mm; FIG. 8F, 3.1 mm.

(FIG. 9A) High magnification reveals differences in levels of expression within seminiferous tubules (FIG. 9C). Hybridization of the testis with a sense strand control probe to fused gave no hybridization (FIG. 9B).

(FIG. 10A) C3H10T1/2 cells were cotransfected with a p9XGliLus, ptkRenilla luciferase and fused or various fused mutants. Cells were harvested 48h after transfection and the luciferase activity was assayed as described in Example 7. (FIG. 10B) Fused transactivation of a Gli reporter construct. C3H10T1/2 cells were cotransfected with a p9XGliLuc reporter construct, ptkRenilla luciferase and a CMV driven expression vector for fused or various fused mutants. Cells were harvested 48 hours after transfection and the luciferase activity was assayed as described in the Examples. The data represents the mean of duplicative determinations.

(FIG. 11A) Dorsal view of tadpole stage embryos. Top embryo is fused-DN (SEQ ID NO. 25) injection and bottom embryo is the control; (FIG. 11B) Side view of tadpole stage embryo. Top embryo is fused-DN injection and bottom embryo is the control; (FIGS. 11C & 11D) Pax-6 staining of stage 16 neurula embryos injected with control DNA and fused-DN (SEQ ID NO:25), respectively; (FIG. 11E) SHh expression in the floor plate of neurula stage control embryo (left) or fused-DN injected embryo (right).

DETAILED DESCRIPTION OF THE PREFERRED EMBODIMENTS

I. Definitions

Figure 6:
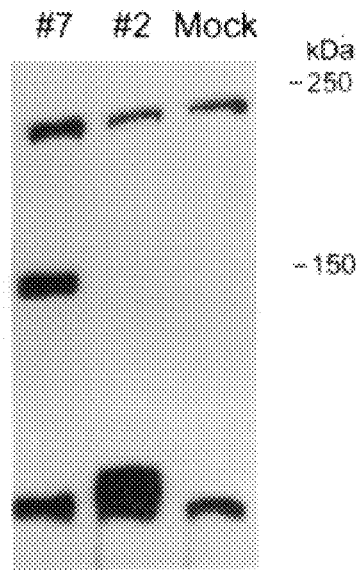
FIG. 6 is a western blot of the PCR product of an epitope tag of DNA 28495 (SEQ ID NO:5 and 21) and DNA28494 (SEQ ID NOS:5 and 22). A specific band of 150 kDa was detected in the cell pellet of cells transfected with the construct corresponding to clone DNA28494 (SEQ ID NO:6) and a specific band of approximately 100 kDa could be detected for clone DNA28495 (SEQ ID NO:4) (FIG. 6). These bands were not present in the mock transfected control. The presence of the 100 kDa band suggests the two open reading frames of DNA28494 (SEQ ID NO:6) can be spliced together to direct the synthesis of a large protein of 150 kDa. The absence of this band for DNA28495 (SEQ ID NO:4) suggested that this clone apparently cannot be correctly spliced.

The terms "vertebrate fitsed" and "vertebrate fused polypeptide" when used herein encompass native sequence vertebrate fused and vertebrate fused variants (which are further defined herein) having fused biological activity. Fused may be isolated from a variety of sources, such as from human tissue types or from another source, or prepared by recombinant or synthetic methods.

Figure 1B:
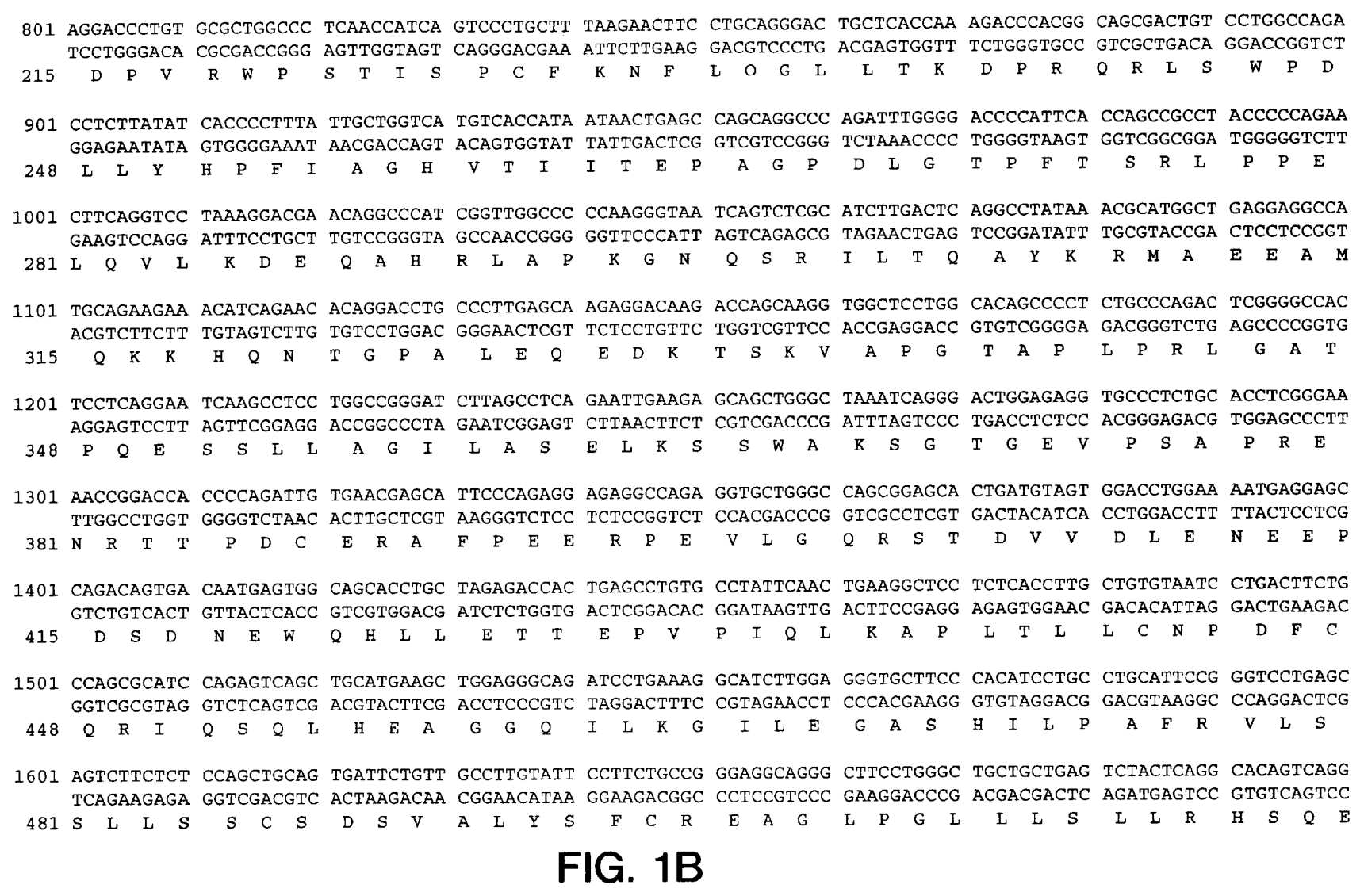
Figure 1E:
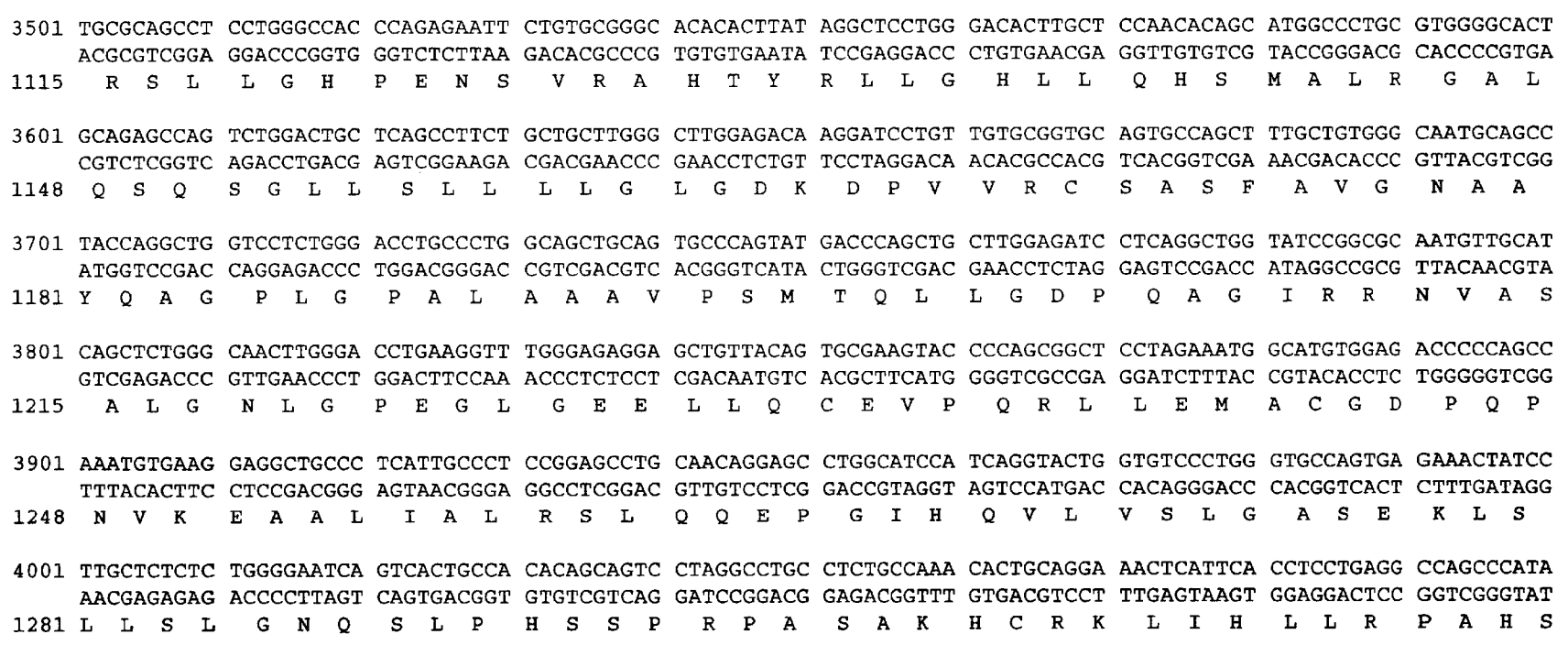

A "native sequence vertebratefitsed" comprises a polypeptide having the same amino acid sequence as a vertebrate fused derived from nature. Such native sequence vertebrate fused can be isolated from nature or can be produced by recombinant and/or synthetic means. The term "native sequence vertebrate fused" specifically encompasses naturally occurring truncated forms of vertebrate fused, naturally occurring variant forms (e.g., alternatively spliced forms) and naturally-occurring allelic variants of vertebrate fused. Native vertebrate fused includes e.g., fused in mammals such as human, murine, bovine, porcine, equine, feline, canine, etc., and preferably refers to human. Thus, one embodiment of the invention, the native sequence human vertebrate fused is a mature or full-length native human vertebrate fused comprising amino acids 1 to 1315 of (SEQ ID NO:2) as shown in FIG. 1 with or without the initiating methionine at position 1.

"Vertebrate fused variant" means an active vertebrate fused as defined below having at least about 80% amino acid sequence identity to (a) a DNA molecule encoding a vertebrate fused polypeptide, or (b) the complement of the DNA molecule of (a). In a particular embodiment, the vertebrate fused variant has at least about 80% amino acid sequence homology with the vertebrate fused having the deduced amino acid sequence (SEQ ID NO:2) shown in FIG. 1 for a full-length native sequence vertebrate fused. Such vertebrate fused variants include, without limitation, vertebrate fused polypeptides wherein one or more amino acid residues are added, or deleted, at the N- or C-terminus of the sequence of FIG. 1 (SEQ ID NO:2). Preferably, the nucleic acid or amino acid sequence identity is at least about 85%, more preferably at least about 90%, and even more preferably at least about 95%.

"Percent (%) amino acid sequence identity" with respect to the vertebrate fused sequences identified herein is defined as the percentage of amino acid residues in a candidate sequence that are identical with the amino acid residues in the vertebrate fused sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for measuring alignment, including any algorithms needed to achieve maximal alignment over the full length of the sequences being compared.

"Percent (%) nucleic acid sequence identity" with respect to the vertebrate fused sequences identified herein is defined as the percentage of nucleotides in a candidate sequence that are identical with the nucleotides in the vertebrate fused sequence, after aligning the sequences and introducing gaps, if necessary, to achieve the maximum percent sequence identity. Alignment for purposes of determining percent nucleic acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for measuring alignment, including any algorithms needed to achieve maximal alignment over the full length of the sequences being compared.

The term "epitope tagged" when used herein refers to a chimeric polypeptide comprising vertebrate fused polypeptide, or a portion thereof, fused to a "tag polypeptide". The tag polypeptide has enough residues to provide an epitope against which an antibody can be made, yet is short enough such that it does not interfere with activity of the vertebrate fused polypeptide. The tag polypeptide preferably also is fairly unique so that the antibody does not substantially cross-react with other epitopes. Suitable tag polypeptides generally have at least six amino acid residues and usually between about 8 to about 50 amino acid residues (preferably, between about 10 to about 20 residues).

As used herein, the term "immunoadhesin" designates antibody-like molecules which combine the binding specificity of a heterologous protein (an "adhesin") with the effector functions of immunoglobulin constant domains. Structurally, the immunoadhesin comprise a fusion of an amino acid sequence with the desired binding specificity which is other than the antigen recognition and binding site of an antibody (i.e., is "heterologous"), and an immunoglobulin constant domain sequence. The adhesin part of an immunoadhesin molecule typically is a contiguous amino acid sequence comprising at least the binding site of a receptor or a ligand. The immunoglobulin constant domain sequence in the immunoadhesins may be obtained from any immunoglobulin, such as IgG-1, IgG-2, IgG-3 or IgG-4 subtypes, IgA (including IgA-1 and IgA-2, IgE, IgD or IgM. Immunoadhesion reported in the literature include fusions of the T cell receptor* [Gascoigne et al., Proc. Natl. Acad. Sci USA 84: 2936–2940 (1987)]; CD4* [Capron et al, Nature 337: 525–531 (1989); Traunecker et al., Nature 339: 68–70 (1989); Zettrneissl et al., DNA Cell Biol. USA 9: 347–353 (1990); Byrn et al., Nature 344, 667–670 (1990)]; L-selectin (homing receptor) [Watson et al., J. Cell. Biol. 110, 2221–2229 (1990); Watson et al., Nature 349, 164–167 (1991)]; CD44* [Aruffo et al., Cell 61, 1303–1313 (1990)] ;CD28* and B7* [Linsley et. al., J Exp. Med. 173, 721–730 (1991)];CTLA-4* [Lisley et al., J. Exp. Med. 174, 561–569 (1991)]; CD22* [Stamenkovic et al., Cell 66. 1133–1144 (1991)]; TNF receptor [Ashkenazi et al., Proc. Natl. Acad Sci. USA 88, 10535–10539 (1991); Lesslauer et al., Eur. J. Iimunol 27, 2883–2886(1991); Peppel et al., J Exp. Med. 174, 1483–1489(1991)]; NP receptors [Bennett et al., J. Biol. Chem. 266, 23060–23067 (1991)]; IgE receptor α-chain* [Ridgway and Gorman, J. Cell. Biol. 115, abstr. 1448 (1991)]; HGF receptor [Mark, M.R. et al., 1992, submitted], where the asterisk (*) indicates that the receptor is member of the immunoglobulin superfamily.

"Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends upon the ability of denatured DNA to reanneal when complementary strands are present in an environment near but below their $T^m$ (melting temperature). The higher the degree of desired homology between the probe and hybridizable sequence, the higher the relative temperature which can be used. As a result, it follows that higher relative temperatures would tend to make the reaction conditions more stringent, while lower temperatures less so. Moreover, stringency is also inversely proportional to salt concentrations. For additional details and explanation of stringency of hybridization reactions, see Ausubel et al., Current Protocols in Molecular Biology (1995).

"Stringent conditions," as defined herein may be identified by those that: (1) employ low ionic strength and high temperature for washing, for example 0.015 M sodium chloride/0.015 M sodium citrate/0.1% sodium dodecyl sulfate at 50° C.; (2) employ during hybridization a denaturing agent, such as formamide, for example, 50% (vol/vol) formamide with 0.1% bovine serum albumin/0.1% Ficoll/ 0.1% polyvinylpurrolidone/50 mM sodium phosphate buffer at pH 6.5 with 750 mM sodium chloride, 75 mM sodium citrate at 42° C.; (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 µg/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C.

"Moderately stringent conditions" may be identified as described by Sambrook et al, *Molecular Cloning: A Laboratory Manual* (New York: Cold Spring Harbor Laboratory Press, 1989), and include the use of a washing solution and hybridization conditions (e.g., temperature, ionic strength and %SDS) less stringent than described above. An example of moderately stringent conditions is a condition such as overnight incubation at 37° C. in a solution comprising: 20% formamide, 5×SSC (150 mM NaCl, 15 mM trisodium citrate), 50 mM sodium phosphate (pH 7.6), 5×Denhardt's solution, 10% dextran sulfate, and 20 mg/mL denatured sheared salmon sperm DNA, followed by washing the filters in 1×SSC at about 37–50° C. The skilled artisan will recognize how to adjust the temperature, ionic strength, etc. as necessary to accommodate factors such as probe length and the like.

"Isolated," when used to describe the various polypeptides disclosed herein, means polypeptide that has been identified and separated and/or recovered from a component of its natural environment. Contaminant components of its natural environment are materials that would typically interfere with diagnostic or therapeutic uses for the polypeptide, and may include enzymes, hormones, and other proteinaceous or non-proteinaceous solutes. In preferred embodiments, the polypeptide will be purified (1) to a degree sufficient to obtain at least 15 residues of N-terminal or internal amino acid sequence by use of a spinning cup sequenator, or (2) to homogeneity by SDS-PAGE under non-reducing or reducing conditions using Coomassie blue or, preferably, silver stain. Isolated polypeptide includes polypeptide in situ within recombinant cells, since at least one component of the vertebrate fused natural environment will not be present. Ordinarily, however, isolated polypeptide will be prepared by at least one purification step.

An "isolated" vertebrate fused nucleic acid molecule is a nucleic acid molecule that is identified and separated from at least one contaminant nucleic acid molecule with which it is ordinarily associated in the natural source of the vertebrate fused nucleic acid. An isolated vertebratefuised nucleic acid molecule is other than in the form or setting in which it is found in nature. Isolated vertebrate fused nucleic acid molecules therefore are distinguished from the corresponding native vertebratefuised nucleic acid molecule as it exists in natural cells.

The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

The term "antibody" is used in the broadest sense and specifically covers single monoclonal antibodies (including agonist and antagonist antibodies), antibody compositions with polyeptopic specificity, as well as antibody fragments (e.g., Fab, F(ab')$_2$ and Fv), so long as they exhibit the desired biological activity.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations that typically include different antibodies directed against different determinants (epitopes), each monoclonal antibody is directed against a single determinant on the antigen. In addition to their specificity, the monoclonal antibodies are advantageous in that they are synthesized by the hybridoma culture, uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler & Milstein, *Nature* 256:495 (1 975), or may be made by recombinant DNA methods [see, e.g. U.S. Pat. No. 4,816,567 (Cabilly et al.)].

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity [U.S. Pat. No. 4,816,567; Cabilly et al.; Morrison et al., *Proc. Natl. Acad. Sci. USA* 81, 6851–6855 (1984)].

"Humanized" forms of non-human (e.g. murine) antibodies are chimeric immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. For the most part, humanized antibodies are human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, corresponding non-human residues replace Fv framework residues of the human immunoglobulin. Furthermore, humanized antibody may comprise residues that are found neither in the recipient antibody nor in the imported CDR or framework sequences. These modifications are made to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin. For further details see: Jones et al., *Nature* 321, 522–525 (1986); Reichmann et al., *Nature* 332, 323–329 (1988); Presta, *Curr. Op. Struct. Biol.* 2 593–596 (1992) and U.S. Pat. No. 5,225,539 (Winter) issued Jul. 6, 1993.

"Active" or "activity" for the purposes herein refers to form(s) of vertebrate fused which retain the biologic and/or immunologic activities of native or naturally occurring vertebrate fused. A preferred activity is the ability to bind to and affect, e.g., block or otherwise modulate, hedgehog signaling. The activity preferably involves the regulation of the pathogenesis of Basal cell carcinoma. Another preferred biological activity is the ability to phosphorylate or modulate the phosphorylation of Gli.

The term "antagonist" is used herein in the broadest sense to include any molecule which blocks, prevents, inhibits, neutralizes the normal functioning offitsed in the Hh signaling pathway. One particular form of antagonist includes a molecule that interferes with the interaction between fused and its binding or complexing proteins. In a similar manner, the term "agonist" is used herein to include any molecule which promotes, enhances or stimulates the normal functioning offiused in the Hh signaling pathway. Suitable molecules that affect the protein-protein interaction of fused and its binding proteins include fragments of the latter or small bioorganic molecules, e.g., peptidomimetics, which will prevent or enhance, as the case may be, the interaction of proper complex formation. Non-limiting examples include proteins, peptides, glycoproteins, glycopeptides, glycolipids, polysaccharides, oligosaccharides, nucleic acids, bioorganic molecules, peptidomimetics, pharmacological agents and their metabolites, transcriptional and translation control sequences, and the like. Another preferred form of antagonist includes antisense nucleotides that inhibit proper transcription of wild type fused. Preferred forms of antagonists and are small molecules, which specifically bind to or block binding of the ATP binding site of fused.

The term "modulation" or "modulating" means upregulation or downregulation of a signaling pathway. Cellular processes under the control of signal transduction may include, but are not limited to, transcription of specific genes; normal cellular functions, such as metabolism, proliferation, differentiation, adhesion, apoptosis and survival, as well as abnormal processes, such as transformation, blocking of differentiation and metastasis.

The techniques of "polymerase chain reaction," or "PCR", as used herein generally refers to a procedure wherein minute amounts of a specific piece of nucleic acid, RNA and/or DNA are amplified as described in U.S. Pat. No. 4,683,195 issued Jul. 28, 1987. Generally, sequence information from the ends of the region of interest or beyond needs to be available, such that oligonucleotide primers can be designed; these primer will be identical or similar in sequence to opposite strands of the template to be amplified. The 5' terminal nucleotides of the two primers may coincide with the ends of the amplified material. PCR sequences form total genomic DNA, and cDNA transcribed from total cellular RNA, bacteriophage, or plasmid sequences, etc. See generally Mullis et al., *Cold Spring Harbor Symp. Qziant. Biol.* 51: 263 (1987); Erlich, Ed., PCR Technology, (Stockton Press, N.Y., 1989). As used herein, PCR is considered to be one, but not the only, example of a nucleic acid test sample comprising the use of a known nucleic acid as a primer and a nucleic acid polymerase to amplify or generate a specific piece of nucleic acid.

II. Compositions and Methods of the Invention

A. Full-length vertebrate fused

The present invention provides newly identified and isolated nucleotide sequences encoding polypeptides referred to in the present application as human and vertebrate jiused. In particular, Applicants have identified and isolated cDNA encoding a vertebrate fused polypeptide, as disclosed in further detail in the Examples below. Using BLAST, BLAST-2 and FastA sequence alignment computer programs, Applicants found that a full-length native sequence human fised (shown in FIG. 3 (SEQ ID NO:2)) has 28% amino acid sequence identity with Drosophila fissed (SEQ ID NO:23). Accordingly, it is presently believed that the human fused disclosed in the present application is a newly identified member of the hedgehog signaling cascade.

The full-length native sequence of human vertebrate Jiused gene, or portions thereof, may be used as hybridization probes for a cDNA library to isolate the full-length gene or to isolate still other vertebrate homolog genes (for instance, those encoding naturally-occurring variants of vertebrate jused or vertebrate fused from other species) which have a desired sequence identity to the vertebrate fused sequence disclosed in FIG. 1 (SEQ ID NO:1). Optionally, the length of the probes will be about 20 to about 50 bases. The hybridization probes may be derived from the nucleotide sequence of FIG. 1 (SEQ ID NO:1) or from genomic sequences including promoters, enhancer elements and introns of native sequence vertebrate fused. By way of example, a screening method will comprise isolating the coding region of the vertebrate fused gene using the known DNA sequence to synthesize a selected probe of about 40 bases. Hybridization probes may be labeled by a variety of labels, including radionucleotides such as $^{32}P$ or $^{35}S$, or enzymatic labels such as alkaline phosphatase coupled to the probe via avidin/biotin coupling systems. Labeled probes having a sequence complementary to that of the vertebrate fused gene of the present invention can be used to screen libraries of human cDNA, genomic DNA or mRNA to determine which members of such libraries the probe hybridizes to.

B. Vertebrate fused Variants

In addition to the full-length native sequence vertebrate fused described herein, it is contemplated that vertebrate fused variants can be prepared. Vertebrate fused variants can be prepared by introducing appropriate nucleotide changes into a known vertebrate fused DNA, or by synthesis of the desired vertebrate fused polypeptides. Those skilled in the art will appreciate that amino acid changes may alter post-translational processes of the vertebrate fused.

Variations in the native full-length sequence vertebrate fused or in various domains of the vertebrate fused described herein, can be made, for example, using any of the techniques and guidelines for conservative and non-conservative mutations set forth, for instance, in U.S. Pat. No. 5,364,934. Variations may be a substitution, deletion or insertion of one or more codons encoding the vertebrate fused that results in a change in the amino acid sequence of the vertebrate fused as compared with the native sequence vertebrate fused. Optionally the variation is by substitution of at least one amino acid with any other amino acid in one or more of the domains of the vertebrate fused. Guidance in determining which amino acid residue may be inserted, substituted or deleted without adversely affecting the desired activity may be found by comparing the sequence of the vertebrate fused with that of homologous known protein molecules and minimizing the number of amino acid sequence changes made in regions of high homology. Amino acid substitutions can be the result of replacing one amino acid with another amino acid having similar structural and/or chemical properties, such as the replacement of a leucine with a serine, i.e., conservative amino acid replacements. Insertions or deletions may optionally be in the range of 1 to 5 amino acids. The variation allowed may be determined by systematically making insertions, deletions or substitutions of amino acids in the sequence and testing the resulting variants for activity in the in vitro assay described in the Examples below.

The variations can be made using methods known in the art such as oligonucleotide-mediated (site-directed) mutagenesis, alanine scanning, and PCR mutagenesis. Site-directed mutagenesis [Carter et al., *Nucl. Acids Res.*, 13:4331 (1986); Zoller et al., *Nucl. Acids Res.*, 10:6487 (1987)], cassette mutagenesis [Wells et al., *Gene*, 34:315 (1985)], restriction selection mutagenesis [Wells et al., *Philos. Trans. R. Soc. London SerA*, 317:415 (1986)] or other known techniques can be performed on the cloned DNA to produce the vertebrate fused variant DNA.

Scanning amino acid analysis can also be employed to identify one or more amino acids along a contiguous sequence. Among the preferred scanning amino acids are relatively small, neutral amino acids. Such amino acids include alanine, glycine, serine, and cysteine. Alanine is typically a preferred scanning amino acid among this group because it eliminates the side-chain beyond the beta-carbon and is less likely to alter the main- chain conformation of the variant. Alanine is also typically preferred because it is the most common amino acid. Further, it is frequently found in both buried and exposed positions [Creighton, *The Proteins*, (W.H. Freeman & Co., N.Y.); Chothia, *J Mol. Biol*, 150:1 (1976)]. If alanine substitution does not yield adequate amounts of variant, an isoteric amino acid can be used.

In the human fused sequence depicted in FIG. 1, the kinase domain is represented by amino acid residues 1–260 (SEQ ID NO:24) of which position lysine 33 appears to be necessary for ATP binding and thus enzymatic activity.

C. Modifications of vertebrate fused

Covalent modifications of vertebrate fused are included within the scope of this invention. One type of covalent modification includes reacting targeted amino acid residues of the vertebrate fised with an organic derivatizing agent that is capable of reacting with selected side chains or the N- or C- terminal residues of the vertebrate fused. Derivatization with bifunctional agents is useful, for instance, for crosslinking vertebrate fused to a water-insoluble support matrix or surface for use in the method for purifying anti-vertebrate fused antibodies, and vice-versa. Commonly used crosslinking agents include, e.g., 1,1 -bis(diazo-acetyl)-2-phenylethane, glutaraldehyde, N-hydroxy-succinimide esters, for example, esters with 4-azido-salicylic acid, homobifunctional imidoesters, including disuccinimidyl esters such as 3,3'-dithiobis-(succinimidyl-propionate), bifunctional maleimides such as bis-N-maleimido-1,8-octane and agents such as methyl-3-[(p-azidophenyl)-dithio]propioimi-date.

Other modifications include deamidation of glutaminyl and asparaginyl residues to the corresponding glutamyl and aspartyl residues, respectively, hydroxylation of proline and lysine, phosphorylation of hydroxyl groups of seryl or threonyl residues, methylation of the α-amino groups of lysine, arginine, and histidine side chains [T.E. Creighton, *Proteins: Structure and Molecular Properties*, W.H. Freeman & Co., San Francisco, pp. 79–86 (1983)], acetylation of the N-terminal amine, and amidation of any C-terminal carboxyl group.

Another type of covalent modification of vertebrate fused comprises linking the vertebrate fused polypeptide to one of a variety of nonproteinaceous polymers, e.g., polyethylene glycol, polypropylene glycol, or polyoxyalkylenes, in the manner set forth in U.S. Pat. Nos. 4,640,835; 4,496,689; 4,301,144; 4,670,417; 4,791,192 or 4,179,337. Such modifications would be expected in increase the half-life of the molecules in circulation in a mammalian system; Extended half-life of fused molecules might be useful under certain circumstances, such as where the fused variant is administered as a therapeutic agent.

The vertebrate fused of the present invention may also be modified in a way to form a chimeric molecule comprising vertebrate fused bonded to another, heterologous polypeptide or amino acid sequence. In one embodiment, such a chimeric molecule comprises a fusion of the vertebrate fused with a tag polypeptide, which provides an epitope to which an anti-tag antibody can selectively bind. The epitope tag is generally placed at the amino- or carboxyl- terminus of the vertebrate fused. The presence of such epitope-tagged forms of the vertebrate fused can be detected using an antibody against the tag polypeptide. Also, provision of the epitope tag enables the vertebrate fused to be readily purified by affinity purification using an anti-tag antibody or another type of affinity matrix that binds to the epitope tag. In an alternative embodiment, the chimeric molecule may comprise a fusion of the vertebrate fused with an immunoglobulin or a particular region of an immunoglobulin. For a bivalent form of the chimeric molecule, such a fusion could be to the Fc region of an IgG molecule. Ordinarily, the C-terminus of a contiguous amino acid sequence of a ligand-(IFN-γ-) binding domain of an IFN-γ receptor is fused to the N-terminus of a contiguous amino acid sequence of an immunoglobulin constant region, in place of the variable region(s), however N-terminal fusions are also possible.

Typically, such fusions retain at least functionally active hinge, CH2 and CH3 domains of the constant region of an immunoglobulin heavy chain. Fusions are also made to the C-terminus of the Fc portion of a constant domain, or immediately N-terminal to the CHl of the heavy chain or the corresponding region of the light chain. This ordinarily is accomplished by constructing the appropriate DNA sequence and expressing it in recombinant cell culture. Alternatively,immunoadhesinsmay be synthesized according to known methods.

The precise site at which the fusion is made is not critical; particularsites are well known and may be selected in order to optimize the biological activity, secretion or binding characteristics of the immunoadhesins.

In a preferred embodiment, the C-terminus of a contiguous amino acid sequence which comprises the binding site(s) for IFN-y is fused , at the N-terminal end, to the C-terminal portion of an antibody (in particularthe Fc domain), containing the effector functions of an immunoglobulin, e.g. immunoglobulin $G_1$ (IgG-1). As hereinabove mentioned, it is possible to fuse the entire heavy chain constant region to the sequence containing the binding site(s). However, more preferably, a sequence beginning in the hinge regionjust upstream of the papain cleavage site (which defines IgG Fc chemically; residue 216, taking the first residue of heavy chain constant region to be 114 [Kobet et al., *supra*], or analogous sites of other immunoglobulins) is used in the fusion. Although it was earlier thought that in immunoadhesins the immunoglobulin light chain would be required for efficient secretion of the heterologous protein-heavy chain fusion proteins, it has been found that even the immunoadhesins containing the whole IgG1 heavy chain are efficiently secreted in the absence of light chain. Since the light chain is unnecessary, the immunoglobulinheavy chain constant domain sequence used in the construction of the immunoadhesins of the present invention may be devoid of a light chain binding site. This can be achieved by removing or sufficiently altering immunoglobulin heavy chain sequence elements to which the light chain is ordinarily linked so that such binding is no longer possible. Thus, the CH1 domain can be entirely removed in certain embodiments of the IFN-γ receptor-immunoglobulinchimeras.

In a particularly preferred embodiment, the amino acid sequence containing the extracellular domain of an IFN-γ receptor is fused to the hinge region and CH2, CH3; or CH1, hinge, CH2 and CH3 domains of an IgG-1, IgG-2, IgG-3, or IgG-4 heavy chain. The construction of a typical structure is disclosed in Example 1.

In some embodiments, the IFN-γ receptor-immunoglobulin molecules (immunoadhesins) are assembled as monomers, dimers or multimers, and particularly as dimers or tetramers. Generally, these assembled immunoadhesins will have known unit structures similar to those of the corresponding immunoglobulins. A basic four chain structural unit (a dimer of two immunoglobulin heavy chain-light chain pairs) is the form in which IgG, IgA and IgE exist. A four chain unit is repeated in the high molecular weight immunoglobulins; IgM generally exists as a pentamer of basic four-chain units held together by disulfide bonds. IgA globulin, and occasionally IgG -globulin, may also exist in a multimeric form in serum. In the case ofmultimers, each four chain unit may be the same or different.

It is not necessary that the entire immunoglobulin portion of the IFN-γ receptor-immunoglobulinchimeras be from the same immunoglobulin. Various portions of different immunoglobulins may be combined, and variants and derivatives of native immunoglobulins can be made as hereinabove described with respect to IFN-γ, in order to optimize the properties of the immunoadhesin molecules. For example, immunoadhesin constructs in which the hinge of Igl-1 was replaced with that of IgG-3 were found to be functional and showed pharmacokinetics comparable to those of immunoadhesinscomprisingthe entire IgG-1 heavy chain.

Various tag polypeptides and their respective antibodies are well known in the art. Examples include poly-histidine (poly-his) or poly-histidine-glycine (poly-his-gly) tags; the flu HA tag polypeptide and its antibody 12CA5 [Field et al., *Mol. Cell. Biol*, 8:2159–2165 (1988)]; the c-myc tag and the 8F9, 3C7, 6E10, G4, B7 and 9E10 antibodies thereto [Evan et al., *Molecular and Cellular Biology*, 5:3610–3616 (1985)]; and the Herpes Simplex virus glycoprotein D (gD) tag and its antibody [Paborsky et al., *Protein Enoineering* 3(6):547–553 (1990)]. Other tag polypeptides include the Flag-peptide [Hopp et al., *Bio Technology*, 6:1204–1210 (1988)]; the KT3 epitope peptide [Martin et al., *Science*, 255:192–194 (1992)]; an α-tubulin epitope peptide [Skinner et al., *J. Biol. Chem.*, 266:15163–15166 (1991)]; and the T7 gene 10 protein peptide tag [Lutz-Freyermuth et al., *Proc. Natl. Acad. Sci. USA*, 87:6393–6397 (1990)]. A preferred tag is the influenza HA tag.

D. Preparation of vertebrate fused

The description below relates primarily to production of a particular vertebrate fused by culturing cells transformed or transfected with a vector containing vertebrate fused nucleic acid. It is, of course, contemplated that alternative methods, which are well known in the art, may be employed to prepare vertebrate fused. For instance, the vertebrate fused sequence, or portions thereof, may be produced by direct peptide synthesis using solid-phase techniques [see, e.g., Stewart et al., *Solid-Phase Peptide Synthesis*, W.H. Freeman Co., San Francisco, CA (1969); Merrifield, *J. Am. Chem. Soc.*, 85:2149–2154 (1963)]. In vitro protein synthesis may be performed using manual techniques or by automation. Automated synthesis may be accomplished, for instance, using an Applied Biosystems Peptide Synthesizer (Foster City, Calif.) using manufacturer's instructions. Various portions of the vertebrate fused may be chemically synthesized separately and combined using chemical or enzymatic methods to produce the full-length vertebrate fused.

1. Isolation of DNA Encoding vertebrate closed

DNA encoding vertebrate fused may be obtained from a cDNA library prepared from tissue believed to possess the vertebrate fused mRNA and to express it at a detectable level. Accordingly, human vertebrate fused DNA can be conveniently obtained from a cDNA library prepared from human tissue, such as described in the Examples. The vertebrate fused-encoding gene may also be obtained from a genomic library or by oligonucleotide synthesis.

Libraries can be screened with probes (such as antibodies to the vertebrate fused or oligonucleotides of at least about 20–80 bases) designed to identify the gene of interest or the protein encoded by it. Screening the cDNA or genomic library with the selected probe may be conducted using standard procedures, such as described in Sambrook et al., *Molecular Cloning: A Laboratory Manual* (New York: Cold Spring Harbor Laboratory Press, 1989). An alternative means to isolate the gene encoding vertebrate fused is to use PCR methodology [Sambrook et al., *supra*; Dieffenbach et al., *PCR Primer: A Laboratory Manual* (Cold Spring Harbor Laboratory Press, 1995)].

The Examples below describe techniques for screening a cDNA library. The oligonucleotide sequences selected as probes should be of sufficient length and sufficiently unambiguous that false positives are minimized. The oligonucleotide is preferably labeled such that it can be detected upon hybridization to DNA in the library being screened. Methods of labeling are well known in the art, and include the use of radiolabels like $^{32}$P-labeled ATP, biotinylation or enzyme labeling. Hybridization conditions, including moderate stringency and high stringency, are provided in Sambrook et al., *supra*.

Sequences identified in such library screening methods can be compared and aligned to other known sequences deposited and available in public databases such as GenBank or other private sequence databases. Sequence identity (at either the amino acid or nucleotide level) within defined regions of the molecule or across the full-length sequence can be determined through sequence alignment using computer softwvare programs such as BLAST, BLAST-2, ALIGN, DNAstar, and INHERIT which employ various algorithms to measure homology.

Nucleic acid having protein coding sequence may be obtained by screening selected cDNA or genomic libraries using the deduced amino acid sequence disclosed herein for the first time, and, if necessary, using conventional primer extension procedures as described in Sambrook et al., *supra*, to detect precursors and processing intermediates of mRNA that may not have been reverse-transcribed into cDNA.

2. Selection and Transformation of Host Cells

Host cells are transfected or transformed with expression or cloning vectors described herein for vertebrate fused production and cultured in conventional nutrient media modified as appropriate for inducing promoters, selecting transformants, or amplifying the genes encoding the desired sequences. The culture conditions, such as media, temperature, pH and the like, can be selected by the skilled artisan without undue experimentation. In general, principles, protocols, and practical techniques for maximizing the productivity of cell cultures can be found in *Mammalian Cell Biotechnology: A Practical Approach*, M. Butler, ed. (IRL Press, 1991) and Sambrook et al., *supra*.

Methods of transfection are known to the ordinarily skilled artisan, for example, $CaPO_4$ and electroporation. Depending on the host cell used, transformation is performed using standard techniques appropriate to such cells. The calcium treatment employing calcium chloride, as described in Sambrook et al., *supra*, or electroporation is generally used for prokaryotes or other cells that contain substantial cell-wall barriers. Infection with *Agrobacterizim tumefaciens* is used for transformation of certain plant cells, as described by Shaw et al., *Gene*, 23:315 (1983) and WO 89/05859 published Jun. 29, 1989. For mammalian cells without such cell walls, the calcium phosphate precipitation method of Graham and van der Eb, *Virology* 52:456–457 (1978) can be employed. General aspects of mammalian cell host system transformations have been described in U.S. Pat. No. 4,399,216. Transformations into yeast are typically carried out according to the method of Van Solingen et al., *J Bact.*, 130:946 (1977) and Hsiao et al., *Proc. Natl. Acad Sci.* (USA), 76:3829 (1979). However, other methods for introducing DNA into cells, such as by nuclear microinjection, electroporation, bacterial protoplast fusion with intact cells, or polycations, e.g., polybrene, polyornithine, may also be used. For various techniques for transforming mammalian cells, see Keown et al., *Methods in Enzymology*, 185:527–537 (1990) and Mansour et al., *Nature*, 336:348–352 (1988).

Suitable host cells for cloning or expressing the DNA in the vectors herein include prokaryote, yeast, or higher eukaryote cells. Suitable prokaryotes include but are not limited to eubacteria, such as Gram-negative or Gram-positive organisms, for example, Enterobacteriae such as *E. coli*. Various *E. coli* strains are publicly available, such as *E. coli* K 12 strain MM294 (ATCC 31,446); *E. coli* X1776 (ATCC 31,537); *E. coli* strain W3110 (ATCC 27,325) and K5 772 (ATCC 53,635).

In addition to prokaryotes, eukaryotic microbes such as filamentous fungi or yeast are suitable cloning or expression hosts for vertebrate fused-encoding vectors. *Saccharomyces cerevisiae* is a commonly used lower eukaryotic host microorganism.

Suitable host cells for the expression of vertebrate fused are derived from multicellular organisms. Examples of invertebrate cells include insect cells such as Drosophila S2 and Spodoptera Sf9, as well as plant cells. Examples of useful mammalian host cell lines include Chinese hamster ovary (CHO) and COS cells. More specific examples include monkey kidney CV1 line transformed by SV40 (COS-7, ATCC CRL 1651); human embryonic kidney line (293 or 293 cells subcloned for growth in suspension culture, Graham et al., *J. Gen Virol,*, 36:59 (1977)); Chinese hamster ovary cells/-DHFR (CHO, Urlaub and Chasin, *Proc. Natl. Acad Sci USA*, 77:4216 (1980)); mouse sertoli cells (TM4, Mather, *Biol. Reprod.* 23:243–251 (1980)); human lung cells (W138, ATCC CCL 75); human liver cells (Hep G2, HB 8065); and mouse mammary tumor (MMT 060562, ATCC CCL51). The selection of the appropriate host cell is deemed to be within the skill in the art.

3. Selection and Use of a Replicable Vector

The nucleic acid (e.g., cDNA or genomic DNA) encoding vertebrate fused may be inserted into a replicable vector for cloning (amplification of the DNA) or for expression. Various vectors are publicly available. The vector may, for example, be in the form of a plasmid, cosmid, viral particle, or phage. The appropriate nucleic acid sequence may be inserted into the vector by a variety of procedures. In general, DNA is inserted into an appropriate restriction endonuclease site(s) using techniques known in the art. Vector components generally include, but are not limited to, one or more of a signal sequence, an origin of replication, one or more marker genes, an enhancer element, a promoter, and a transcription termination sequence. Construction of suitable vectors containing one or more of these components employs standard ligation techniques, which are known to the skilled artisan.

Both expression and cloning vectors contain a nucleic acid sequence that enables the vector to replicate in one or more selected host cells. Such sequences are well known for a variety of bacteria, yeast, and viruses. The origin of replication from the plasmid pBR322 is suitable for most Gram-negative bacteria, the 2: plasmid origin is suitable for yeast, and various viral origins (SV40, polyoma, adenovirus, VSV or BPV) are useful for cloning vectors in mammalian cells. A preferred replicable expression vector is the plasmid is pRK5. Holmes et al., *Science*, 253:1278–1280 (1991).

Expression and cloning vectors will typically contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for *Bacilli*.

An example of suitable selectable markers for mammalian cells are those that enable the identification of cells competent to take up the vertebrate fused nucleic acid, such as DHFR or thymidine kinase. An appropriate host cell when wild-type DHFR is employed is the CHO cell line deficient in DHFR activity, prepared and propagated as described by Urlaub et al., *Proc. Natl. Acad. Sci. USA*, 77:4216 (1980). A suitable selection gene for use in yeast is the trp1 gene present in the yeast plasmid YRp7 [Stinchcomb et al., *Nature*, 282:39 (1979); Kingsman et al., *Gene*, 7:141 (1979); Tschemper et al., *Gene*, 10:157 (1980)]. The trp1 gene provides a selection marker for a mutant strain of yeast lacking the ability to grow in tryptophan, for example, ATCC No. 44076 or PEP4-1 [Jones, *Genetics*, 85:12 (1977)].

Expression and cloning vectors usually contain a promoter operably linked to the vertebrate fused nucleic acid sequence to direct mRNA synthesis. Promoters recognized by a variety of potential host cells are well known. Promoters suitable for use with prokaryotic hosts include the β-lactamase and lactose promoter systems [Chang et al, *Nature*, 275:615 (1978); Goeddel et al., *Nature*, 281:544 (1979)], alkaline phosphatase, a tryptophan (trp) promoter system [Goeddel, *Nucleic Acids Res.* 8:4057 (1980); EP 36,776], and hybrid promoters such as the tac promoter [deBoer et al., *Proc. Natl. Acad Sci. USA*, 80:21–25 (1983)].

Promoters for use in bacterial systems also will contain a Shine-Dalgarno (S.D.) sequence operably linked to the DNA encoding vertebrate fused.

Examples of suitable promoting sequences for use with yeast hosts include the promoters for 3-phosphoglycerate kinase [Hitzeman et al., *J. Biol. Chem*, 255:2073 (1980)] or other glycolytic enzymes [Hess et al., *J Adv. Enzyme Reg.*, 7:149 (1968); Holland, *Biochemistry*, 17:4900 (1978)], such as enolase, glyceraldehyde-3-phosphate dehydrogenase, hexokinase, pyruvate decarboxylase, phospho-fructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657.

Vertebrate fused transcription from vectors in mammalian host cells is controlled, for example, by promoters obtained from the genomes of viruses such as polyoma virus, fowlpox virus (UK 2,211,504 published Jul. 5, 1989), adenovirus (such as Adenovirus 2), bovine papilloma virus, avian sarcoma virus, cytomegalovirus, a retrovirus, hepatitis-B virus and Simian Virus 40 (SV40), from heterologous mammalian promoters, e.g., the actin promoter or an immunoglobulin promoter, and from heat-shock promoters, provided such promoters are compatible with the host cell systems.

Inserting an enhancer sequence into the vector may increase transcription of a DNA encoding the vertebrate fused by higher eukaryotes. Enhancers are cis-acting elements of DNA, usually about from 10 to 300 bp, that act on a promoter to increase its transcription. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100–270), the cytomegalovirus early promoter enhancer, the polyoma enhancer on the late side of the replication origin, and adenovirus enhancers. The enhancer may be spliced into the vector at a position 5' or 3' to the vertebrate fused coding sequence, but is preferably located at a site 5' from the promoter.

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding vertebrate fused.

Still other methods, vectors, and host cells suitable for adaptation to the synthesis of vertebrate fused in recombinant vertebrate cell culture are described in Gething et al., *Nature*, 293:620–625 (1981); Mantei et al., *Nature*, 281:40–46 (1979); EP 117,060; and EP 117,058.

4. Detecting Gene Amplification/Exiression

Gene amplification and/or expression may be measured in a sample directly, for example, by conventional Southern blotting, Northern blotting to quantitate the transcription of mRNA [Thomas, *Proc. Natl. Acad. Sci. USA*, 77:5201–5205 (1980)], dot blotting (DNA analysis), or in situ hybridization, using an appropriately labeled probe, based on the sequences provided herein. Alternatively, antibodies may be employed that can recognize specific duplexes, including DNA duplexes, RNA duplexes, and DNA-RNA hybrid duplexes or DNA-protein duplexes. The antibodies in turn may be labeled and the assay may be carried out where the duplex is bound to a surface, so that upon the formation of duplex on the surface, the presence of antibody bound to the duplex can be detected.

Gene expression, alternatively, may be measured by immunological methods, such as immunohistochemical staining of cells or tissue sections and assay of cell culture or body fluids, to quantitate directly the expression of gene product. Antibodies useful for immunohistochemical staining and/or assay of sample fluids may be either monoclonal or polyclonal, and may be prepared in any mammal. Conveniently, the antibodies may be prepared against a native sequence vertebrate fused polypeptide or against a synthetic peptide based on the DNA sequences provided herein or against exogenous sequence fused to vertebrate fused DNA and encoding a specific antibody epitope.

5. Purification of Polypeptide

Forms of vertebrate fused may be recovered from host cell lysates. If membrane-bound, it can be released from the membrane using a suitable detergent solution (e.g. Triton-X 100) or by enzymatic cleavage. Cells employed in expression of vertebrate fused can be disrupted by various physical or chemical means, such as freeze-thaw cycling, sonication, mechanical disruption, or cell lysing agents.

It may be desired to purify vertebrate fiused from recombinant cell proteins or polypeptides. The following procedures are exemplary of suitable purification procedures: by fractionation on an ion-exchange column; ethanol precipitation; reverse phase HPLC; chromatography on silica or on a cation-exchange resin such as DEAE; chromatofocusing; SDS-PAGE; ammonium sulfate precipitation; gel filtration using, for example, Sephadex G-75; protein A Sepharose columns to remove contaminants such as IgG; and metal chelating columns to bind epitope-tagged forms of the vertebrate fused. Various methods of protein purification may be employed and such methods are known in the art and described for example in Deutscher, *Methods in Enzvmoloey*, 182 (1990); Scopes, *Protein Purification: Principles and Practice*, Springer-Verlag, New York (1982). The purification step(s) selected will depend, for example, on the nature of the production process used and the particular vertebrate fused produced.

E. Uses for vertebrate fused (1) Fuised is universal mediator of Hh signaling

The human fused full length molecule of human (FIG. 1 (SEQ ID NO: 1)) encodes a protein with a predicted molecular weight of 150 kDa, which is significantly larger that Drosophila fused (100 kDa, dfused (SEQ ID NO:23)). Human fused (hfused) shows notable homology to the Drosophila homologue in the kinase domain, but little homology with dfused or any other known protein over the remaining ≈1000 amino acids. The kinase domain extends from residue 1 to about residue 260, as is represented in FIG. 1 (SEQ ID NOS:24 and 2). This divergence at the C-terminus of the molecules is unexpected given that the C-terminus of the Drosophila molecule is required for its activity, Preat et al., *Nature* 347: 87–9 (1990). An ATP binding site is at about amino acid position 33 and is required for kinase activity.

Prior studies in Drosophila indicate that dfused is necessary for Hh signal to occur but have not addressed the issue whether fused is sufficient to activate this signaling system. As depicted in the Examples, applicants have herein used a Gli DNA binding element present in the HNF3β promoter, in front of a luciferase mediator of the Hh cascade, which clearly demonstrates that fused alone is capable of activating Gli mediated transcription in this system. It is further apparent that both an intact kinase domain and an intact C-terminal non-catalytic domain are required for this activation, which supports the notion that fused functions as a kinase and that the C-terminus may play a role in the substrate recognition or in regulating the kinase activity.

Applicants have shown in the present application that hfused is a kinase which is capable of phosphorylating artificial substrates such as MBP. However, the identity of the physiological substrate for hfused remains to be determined. One obvious candidate is Gli-1 itself, as Gli-1 phosphorylation by hfiosed can be detected in vitro.

To determine if human fused is essential for Hh signaling in vertebrates, a mutant was constructed by altering a conserved lysine in the ATP binding site (about amino acid residue 33). Typically, such mutants act as inhibitor of the corresponding wild type kinase by blocking access to substrate and/or regulatory factors, He et al., *Nature* 374, 617–22 (1995). When overexpressed in 2-cell stage Xenopus embryos, the most remarkable phenotype was the presence of fused eyes in about 30% of the injected embryos. Several lines of evidence indicate that this phenotype is likely to result from the inhibition of Hh signaling. First, SHh knockouts display a cyclopia phenotype attributed recently to mutations in the SHh gene, Chiang et al., *Nature* 383: 407–13 (1996). Second, zebrafish embryos (cyclops) with reduced expression of SHh or injected with constitutively active form of PKA, a negative regulator of the Hh pathway are cyclops. Third, SHh, emanating from prechordal plate, has been shown to inhibit expression of Pax-6, a key transcription factor required for eye development, in the center of a continuous eyefield, Ekker et al., *Curr. Biol.* 5: 944–55 (1995); Li et al., *Development.* 124: 603–15 (1997); Macdonald et al., *Development* 121: 3267–78 (1995). Finally, staining for Pax-6 embryos injected with fused -DN revealed a single field of expression suggesting a failure of SHh emanating from the prechordal plate to downregulate the expression of Pax-6 at the center of the eyefield.

To confirm the position of fused in the Hh signaling pathway, expression of SHh in the floor plate of Xenopus embryos injected with hfitsed-DN could be rescued by coinjection of Gli-1. This suggests that fused acts in association with Gli in the SHh signaling pathway.

The tissue distribution of fused shows that it is expressed in all SHh responsive cells. In particular, its expression pattern overlaps well with Ptch, the binding component of the Hh receptor which is itself a target gene of the SHh signaling pathway. These data suggest that fused is involved in mediating a wide variety of effect SHh has on different tissues. Functionally, this was observed again in frog embryos where, fused-DN inhibited eye development as well as SHh expression in the floor plate.

hFused-DN also appears to affect normal development of tissues such as the frog gut which is regulated by Indian Hh. This, combined with the fact that fused is expressed in the gut and testis, sites of IHh and DHh action respectively, suggest that fuised may be a universal mediator of signaling for all members of the Hh protein family.

Very high levels of fused mRNA was found on germ cell, the development of which appears to be regulated by DHh. Homozygous mutant mice for DHh fail to develop germ cells and are viable but sterile (Bitgood et al., *Curr. Biol.* 6: 298–304 (1996). However, Patched, a Hedgehog receptor is expressed on interstitial Leydig cells and not on germ cells where fused is expressed, Bitgood et al, supra. This discrepancy suggests that there may be additional hedgehog receptors.

Applicants have shown in the Examples that wild type h fused is capable of activating Gli in a reporter assay. Furthermore, expression of SHh in the floor plate of frog embryos injected with hfused-DN could be rescued by coinjection of Gli-1. Taken together these observations are consistent with the assertion that fused acts downstream of Smo and upstream of Gli in this signaling pathway, which is consistent with the genetic evidence in Drosophila to date.

(2) General usesfor vertebrate fused

Nucleotide sequences (or their complement) encoding vertebrate fused have various applications in the art of molecular biology, including uses as hybridization probes, in chromosome and gene mapping and in the generation of anti-sense RNA and DNA. Vertebrate fused nucleic acid will also be useful for the preparation of vertebrate fused polypeptides by the recombinant techniques described herein.

The full-length native sequence vertebrate fused gene, or portions thereof, may be used as hybridization probes for a cDNA library to isolate the full-length gene or to isolate still other genes (for instance, those encoding naturally-occurring variants of vertebrate fused or vertebrate fused from other species) which have a desired sequence identity to the vertebrate fused sequence disclosed in FIG. 1 (SEQ ID NO:1). Optionally, the length of the probes will be about 20 to about 50 bases. The hybridization probes may be derived from the nucleotide sequence of FIG. 1 or from genomic sequences including promoters, enhancer elements and introns of native sequence vertebrate fused. By way of example, a screening method will comprise isolating the coding region of the vertebrate fused gene using the known DNA sequence to synthesize a selected probe of about 40 bases. Hybridization probes may be labeled by a variety of labels, including radionucleotides such as $^{32}p$ or $^{35}S$, or enzymatic labels such as alkaline phosphatase coupled to the probe via avidin/biotin coupling systems. Labeled probes having a sequence complementary to that of the vertebrate fused gene of the present invention can be used to screen libraries of human cDNA, genomic DNA or mRNA to determine to which members of such libraries the probe hybridizes. Hybridization techniques are described in further detail in the Examples below.

The probes may also be employed in PCR techniques to generate a pool of sequences for identification of closely related vertebrate fused sequences.

Nucleotide sequences encoding a vertebrate fused can also be used to construct hybridization probes for mapping the gene, which encodes vertebrate fused and for the genetic analysis of individuals with genetic disorders. The nucleotide sequences provided herein may be mapped to a chromosome and specific regions of a chromosome using known techniques, such as in situ hybridization, linkage analysis against known chromosomal markers, and hybridization screening with libraries.

Vertebrate fused polypeptides can be used in assays to identify the other proteins or molecules involved in complexing with fused which ultimately results in the modulation of hedgehog signaling. Alternatively, the these molecules can modulate the fused kinase phosphorylation of its substrate. By such methods, inhibitors of the binding interaction can be identified. Proteins involved in such binding interactions can also be used to screen for peptide or small molecule inhibitors or agonists of the binding interaction. Also, the substrate of vertebrate fused can be used to isolate correlative complexing proteins. Screening assays can be designed to find lead compounds that mimic the biological activity of a native vertebrate fused or to find those that act as a substrate for vertebrate fused. Such screening assays will include assays amenable to high-throughput screening of chemical libraries, making them particularly suitable for identifying small molecule drug candidates. Such small molecule inhibitors could block the enzymatic action of fused, and thereby inhibit hedgehog signaling. Small molecules contemplated include synthetic organic or inorganic compounds. The assays can be performed in a variety of formats, including protein-protein binding assays, biochemical screening assays, immunoassays and cell based assays, which are well characterized in the art.

Nucleic acids which encode vertebrate fused or its modified forms can also be used to generate either transgenic animals or "knock out" animals which, in turn, are useful in the development and screening of therapeutically useful reagents. A transgenic animal (e.g., a mouse or rat) is an animal having cells that contain a transgene, which transgene was introduced into the animal or an ancestor of the animal at a prenatal, e.g., an embryonic stage. A transgene is a DNA that is integrated into the genome of a cell from which a transgenic animal develops. In one embodiment, cDNA encoding vertebrate fused can be used to clone genomic DNA encoding vertebrate fused in accordance with established techniques and the genomic sequences used to generate transgenic animals that contain cells which express DNA encoding vertebrate fused. Methods for generating transgenic animals, particularly animals such as mice or rats, have become conventional in the art and are described, for example, in U.S. Pat. Nos. 4,736,866 and 4,870,009. Typically, particular cells would be targeted for vertebrate fused transgene incorporation with tissue-specific enhancers. Transgenic animals that include a copy of a transgene encoding vertebrate fused introduced into the germ line of the animal at an embryonic stage can be used to examine the effect of increased expression of DNA encoding vertebrate fused. Such animals can be used as tester animals for reagents thought to confer protection from, for example, pathological conditions associated with its overexpression. For example, for basal cell carcinoma, fused can be overexpressed in the basal cell layer of the skin using a Keratin 5 or 14 promoter. In accordance with this facet of the invention, an animal is treated with the reagent and a reduced incidence of the pathological condition, compared to untreated animals bearing the transgene, would indicate a potential therapeutic intervention for the pathological condition.

Non-human homologues of vertebrate fused can be used to construct a vertebrate fised "knock out" animal which has a defective or altered gene encoding vertebrate fused as a result of homologous recombination between the endogenous gene encoding vertebrate fused and altered genomic DNA encoding vertebrate fused introduced into an embryonic cell of the animal. For example, cDNA encoding vertebrate fused can be used to clone genomic DNA encoding vertebrate fused in accordance with established techniques. A portion of the genomic DNA encoding vertebrate fused can be deleted or replaced with another gene, such as a gene encoding a selectable marker that can be used to monitor integration. Typically, several kilobases of unaltered flanking DNA (both at the 5' and 3' ends) are included in the vector [see e.g., Thomas and Capecchi, Cell, 51:503 (1987) for a description of homologous recombination vectors]. The vector is introduced into an embryonic stem cell line (e.g., by electroporation) and cells in which the introduced DNA has homologously recombined with the endogenous DNA are selected [see e.g., Li et al., Cell, 69:915 (1992)]. The selected cells are then injected into a blastocyst of an animal (e.g., a mouse or rat) to form aggregation chimeras [see e.g., Bradley, in Teratocarcinomas and Embryonic Stem Cells: A Practical Approach, E. J. Robertson, ed. (IRL, Oxford, 1987), pp. 113–152]. A chimeric embryo can then be implanted into a suitable pseudopregnant female foster animal and the embryo brought to term to create a "knock out" animal. Progeny harboring the homologously recombined DNA in their germ cells can be identified by standard techniques and used to breed animals in which all cells of the animal contain the homologously recombined DNA. Knockout animals can be characterized for instance, for their ability to defend against certain pathological conditions and for their development of pathological conditions due to absence of the vertebrate fused polypeptide.

As fused has been implicated as a universal mediator for all member of the Hh family (SHh, IHh, DHh), disease states or disorders which are associated with general Hh signaling, would also be treatable with fused and antagonists and agonists thereof. For example, SHh activation (e.g. fused agonists) has recently been promoted as a treatment for various degenerative disorders of the nervous system, e.g., Parkinson's disease, memory deficits, Alzheimer's disease, Lou Gehrig's disease, Huntington's disease, schizophrenia, stroke and drug addiction. Recent studies suggest that Dhh mutant males are infertile due to the failure of spermatocytes to complete their differentiation into mature sperm, Bitgood et al., Curr. Biol. 6: 298–304 (1996); Bitgood et al., Dev. Biol. 172:126–138 (1995). Additionally, fused agonists could be used to great gut diseases, bone diseases, skin diseases, diseases of the testis, ulcers, lung diseases, diseases of the pancreas, diabetes, osteoporosis.

The presence of the protein kinase domain suggests that fused may act similarly as members of the protein kinase family in the modulation of Hh signaling. Protein kinases are essential elements of regulatory circuits in differentiated as well as growing cells; Preat et al., Nature 347: 87–89 (1990). Many of these enzyme are involved in transduction of extracellular signals and operate through a cascade of phosphorylation events that amplify and disseminate the effects of a primary signal. As described earlier, Drosophila fused bears significant homology to other intracellular serine/threonine kinases. Many serine/threonine kinases are implicated in cell-cycle control in yeasts and in mammals, Hunter, Cell 50: 823–829 (1987); Dunphy & Newport, Cell 55: 925–928 (1988); Lee & Nurse, Trend. Genet. 4: 287–290 (1988).

Suppression or inhibition of Hh signaling is also an objective of therapeutic strategies. Since inactive fused has been shown to inhibit Hh signaling, it follows that a fused antagonist would also be expected to be antagonistic to Hh signaling. Limiting Hh signaling would be useful in disease states or disorders characterized by Hh signaling. For example, SHh is known to be active in Basal Cell Carcinoma; DHh is known to be active in spermatogenesis. Inhibitor or antagonist of Hh signaling would be effective therapeutics in the treatment of Basal Cell Carcinoma or male contraception, respectively.

The stimulation of Hh signaling is also an objective of therapeutic strategies. Activating Hh signaling would be useful in disease states or disorders characterized by inactive or insufficient Hh signaling. For example, degenerative disorders of the nervous system, e.g., Parkinson's disease, memory deficits, Alzheimer's disease, Lou Gehrig's disease, Huntington's disease, schizophrenia, stroke and drug addiction. Additionally, fused agonists could be used to great gut diseases, bone diseases, skin diseases, diseases of the testis (including infertility), ulcers, lung diseases, diseases of the pancreas, diabetes, osteoporosis.

F. Anti-vertebrate fitsed Antibodies

The present invention further provides anti- vertebrate fused antibodies. Exemplary antibodies include polyclonal, monoclonal, humanized, bispecific, and heteroconjugate antibodies.

1. Polyclonal Antibodies

The anti-vertebrate fised antibodies may comprise polyclonal antibodies. Methods of preparing polyclonal antibodies are known to the skilled artisan. Polyclonal antibodies can be raised in a mammal, for example, by one or more injections of an immunizing agent and, if desired, an adjuvant. Typically, the immunizing agent and/or adjuvant will be injected in the mammal by multiple subcutaneous or intraperitoneal injections. The immunizing agent may include the vertebrate fused polypeptide or a fusion protein thereof. It may be useful to conjugate the immunizing agent to a protein known to be immunogenic in the mammal being immunized. Examples of such immunogenic proteins include but are not limited to keyhole limpet hemocyanin, serum albumin, bovine thyroglobulin, and soybean trypsin inhibitor. Examples of adjuvants that may be employed include Freund's complete adjuvant and MPL-TDM adjuvant (monophosphoryl Lipid A, synthetic trehalose dicorynomycolate). The immunization protocol may be selected by one skilled in the art without undue experimentation.

2. Monoclonal Antibodies

The anti-vertebrate fused antibodies may, alternatively, be monoclonal antibodies. Monoclonal antibodies may be prepared using hybridoma methods, such as those described by Kohler and Milstein, *Nature*, 256:495 (1975). In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes may be immunized in vitro.

The immunizing agent will typically include the vertebrate fused polypeptide or a fusion protein thereof. Generally, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell [Goding, *Monoclonal Antibodies: Principles and Practice*, Academic Press, (1986) pp. 59–103]. Immortalized cell lines are usually transformed mammalian cells, particularly myeloma cells of rodent, bovine and human origin. Usually, rat or mouse myeloma cell lines are employed. The hybridoma cells may be cultured in a suitable culture medium that preferably contains one or more substances that inhibit the growth or survival of the un fused , immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, California and the American Type Culture Collection, Rockville, Maryland. Human myeloma and mouse-human heteromyeloma cell lines also have been described for the production of human monoclonal antibodies [Kozbor, *J. Immunol.*, 133:3001 (1984); Brodeur et al., *Monoclonal Antibody Production Techniques and Applications*, Marcel Dekker, Inc., New York, (1987) pp. 51–63].

The culture medium in which the hybridoma cells are cultured can then be assayed for the presence of monoclonal antibodies directed against vertebrate fused. Preferably, the binding specificity of monoclonal antibodies produced by the hybridoma cells is determined by immunoprecipitation or by an in vitro binding assay, such as radioimmunoassay (RIA) or enzyme-linked immunoabsorbent assay (ELISA). Such techniques and assays are known in the art. The binding affinity of the monoclonal antibody can, for example, be determined by the Scatchard analysis of Munson and Pollard, *Anal. Biochem.*, 107:220 (1980).

After the desired hybridoma cells are identified, the clones may be subcloned by limiting dilution procedures and grown by standard methods [Goding, *supra*]. Suitable culture media for this purpose include, for example, Dulbecco's Modified Eagle's Medium and RPMI-1640 medium. Alternatively, the hybridoma cells may be grown in vivo as ascites in a mammal.

The monoclonal antibodies secreted by the subclones may be isolated or purified from the culture medium or ascites fluid by conventional immunoglobulin purification procedures such as, for example, protein A-Sepharose, hydroxylapatite chromatography, gel electrophoresis, dialysis, or affinity chromatography.

The monoclonal antibodies may also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA may be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences [U.S. Pat. No. 4,816,567; Morrison et al., *supra*] or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

The antibodies may be monovalent antibodies. Methods for preparing monovalent antibodies are well known in the art. For example, one method involves recombinant expression of immunoglobulin light chain and modified heavy chain. The heavy chain is truncated generally at any point in the Fc region so as to prevent heavy chain crosslinking. Alternatively, the relevant cysteine residues are substituted with another amino acid residue or are deleted so as to prevent crosslinking.

In vitro methods are also suitable for preparing monovalent antibodies. Digestion of antibodies to produce fragments thereof, particularly, Fab fragments, can be accomplished using routine techniques known in the art.

3. Humanized Antibodies

The anti-vertebrate fused antibodies of the invention may further comprise humanized antibodies or human antibodies. Humanized forms of non-human (e.g., murine) antibodies are chimeric immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues that are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin [Jones et al., *Nature*, 321:522–525 (1986); Riechmann et al., *Nature*, 332:323–329 (1988); and Presta, *Curr. Op. Struct. Biol.*, 2:593–596 (1992)].

Methods for humanizing non-human antibodies are well known in the art. Generally, a humanized antibody has one or more amino acid residues introduced into it from a source that is non-human. These non-human amino acid residues are often referred to as "import" residues, which are typically taken from an "import" variable domain. Humanization can be essentially performed following the method of Winter and co-workers [Jones et al., *Nature*, 321:522–525 (1986); Riechmann et al., *Nature*, 332:323–327 (1988); Verhoeyen et al., *Science*, 239:1 534–1536 (1988)], by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries [Hoogenboom and Winter, *J. Mol. Biol.*, 227:381 (1991); Marks et al., *J. Mol. Biol.*, 222:581 (1991)]. The techniques of Cole et al. and Boerner et al. are also available for the preparation of human monoclonal antibodies (Cole et al., *Monoclonal Antibodies and Cancer Therapy*, Alan R. Liss, p. 77 (1985) and Boemer et al., *J. Immunol.*, 147(1):86–95 (1991)].

4. Bispecific Antibodies

Bispecific antibodies are monoclonal, preferably human or humanized, antibodies that have binding specificities for at least two different antigens. In the present case, one of the binding specificities is for the vertebrate fused, the other one is for any other antigen, and preferably for a cell-surface protein or receptor or receptor subunit.

Methods for making bispecific antibodies are known in the art. Traditionally, the recombinant production of bispecific antibodies is based on the co-expression of two immunoglobulin heavy-chain/light-chain pairs, where the two heavy chains have different specificities [Milstein and Cuello, *Nature*, 305:537–539 (1983)]. Because of the random assortment of immunoglobulin heavy and light chains, these hybridomas (quadromas) produce a potential mixture of ten different antibody molecules, of which only one has the correct bispecific structure. The purification of the correct molecule is usually accomplished by affinity chromatography steps. Similar procedures are disclosed in WO 93/08829, published May 13, 1993, and in Traunecker et al., *EMBO J.*, 10:3655–3659 (1991).

Antibody variable domains with the desired binding specificities (antibody-antigen combining sites) can be fused to immunoglobulin constant domain sequences. The fusion preferably is with an immunoglobulin heavy-chain constant domain, comprising at least part of the hinge, CH2, and CH3 regions. It is preferred to have the first heavy-chain constant region (CH1) containing the site necessary for light-chain binding present in at least one of the fusions. DNAs encoding the immunoglobulin heavy-chain fusions and, if desired, the immunoglobulin light chain, are inserted into separate expression vectors, and are co-transfected into a suitable host organism. For further details of generating bispecific antibodies see, for example, Suresh et al., *Methods in Enzymology*, 121:210 (1986).

5. Heteroconjugate Antibodies

Heteroconjugate antibodies are also within the scope of the present invention. Heteroconjugate antibodies are composed of two covalently joined antibodies. Such antibodies have, for example, been proposed to target immune system cells to unwanted cells [U.S. Pat. No. 4,676,980], and for treatment of HIV infection [WO 91/00360; WO 92/200373; EP 03089]. It is contemplated that the antibodies may be prepared in vitro using known methods in synthetic protein chemistry, including those involving crosslinking agents. For example, immunotoxins may be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980.

G. Uses for anti-vertebrate fused Antibodies

The anti-vertebrate fused antibodies of the invention have various utilities. For example, anti-vertebrate fused antibodies may be used in diagnostic assays for vertebrate fused, eg., detecting its expression in specific cells, tissues, or serum. Various diagnostic assay techniques known in the art may be used, such as competitive binding assays, direct or indirect sandwich assays and immunoprecipitation assays conducted in either heterogeneous or homogeneous phases [Zola, *Monoclonal Antibodies: A Manual of Techniques*

CRC Press, Inc. (1987) pp. 147–158]. The antibodies used in the diagnostic assays can be labeled with a detectable moiety. The detectable moiety should be capable of producing, either directly or indirectly, a detectable signal. For example, the detectable moiety may be a radioisotope, such as $^3$H, $^{14}$C, $^{32}$P, $^{35}$S, or $^{125}$I, a fluorescent or chemiluminescent compound, such as fluorescein isothiocyanate, rhodamine, or luciferin, or an enzyme, such as alkaline phosphatase, beta-galactosidase or horseradish peroxidase. Any method known in the art for conjugating the antibody to the detectable moiety may be employed, including those methods described by Hunter et al., *Nature*, 144:945 (1962); David et al., *Biochemistry*, 13:1014 (1974); Pain et al., *J. Immunol. Meth.*, 40:219 (1981); and Nygren, *J. Histochem. and Cytochem.*, 30:407 (1982).

Anti-vertebrate fused antibodies also are useful for the affinity purification of vertebrate fused from recombinant cell culture or natural sources. In this process, the antibodies against vertebrate fused are immobilized on a suitable support, such a Sephadex resin or filter paper, using methods well known in the art. The immobilized antibody then is contacted with a sample containing the vertebrate fused to be purified, and thereafter the support is washed with a suitable solvent that will remove substantially all the material in the sample except the vertebrate fused, which is bound to the immobilized antibody. Finally, the support is washed with another suitable solvent that will release the vertebrate fused from the antibody.

H. Fused Antagonists

Several approaches may be suitably employed to create the fused antagonist and agonist compounds of the present invention. Any approach where the antagonist molecule can be targeted to the interior of the cell, which interferes or prevents wild type fused from normal operation is suitable. For example, competitive inhibitors, including mutant fused such as dominant negative mutant identified in the Examples, which prevent fused from properly binding with other proteins necessary for Hh signaling. Additional properties of such antagonist or agonist molecules are readily determinable by one of ordinary skill, such as size, charge and hydrophobicity suitable for transmembrane transport.

Where mimics or other mammalian homologues of fused are to be identified or evaluated, the cells are exposed to the test compound and compared to positive controls which are exposed only to human fused, and to negative controls which were not exposed to either the compound or the natural ligand. Where antagonists or agonists of fused signal modulation are to be identified or evaluated, the cells are exposed to the compound of the invention in the presence of the natural ligand and compared to controls which are not exposed to the test compound.

Detection assays may by employed as a primary screen to evaluate the phosphatase inhibition/enhancing activity of the antagonist/agonist compounds of the invention. The assays may also be used to assess the relative potency of a compound by testing a range of concentrations, in a range from 100 mM to 1 pM, for example, and computing the concentration at which the amount of phosphorylation or signal transduction is reduced or increased by 50% ($IC_{50}$) compared to controls.

Assays can be performed to identify compounds that affect phosphorylation of fused substrates. Specifically, assays can be performed to identify compounds that increase the phosphorylation activity of fused or assays can be performed to identify compounds that decrease the phosphorylation of fused substrates. These assays can be performed either on whole cells themselves or on cell extracts. The assays can be performed in a variety of formats, including protein-protein binding assays, biochemical screening assays, immunoassays, cell based assays, etc. Such assay formats are well known in the art.

The screening assays of the present invention are amenable to high-throughput screening of chemical libraries, and are particularly suitable for identifying small molecule drug candidates.

(1) Antagonist and agonist molecules

To screen for antagonists and/or agonists of fused signaling, the assay mixture is incubated under conditions whereby, but for the presence of the candidate pharmacological agent, fused induces hedgehog signaling with a reference activity. The mixture components can be added in any order that provides for the requisite hedgehog activity. Incubation may be performed at any temperature that facilitates optimal binding, typically between about 4° and 40° C., more commonly between about 15° and 40° C. Incubation periods are likewise selected for optimal binding but also minimized to facilitate rapid, high-throughput screening, and are typically between about 0.1 and 10 hours, preferably less than 5 hours, more preferably less than 2 hours. After incubation, the effect of the candidate pharmacological agent on the fused signaling is determined in any convenient way. For cell-free binding-type assays, a separation step is often used to separate bound and unbound components. Separation may, for example, be effected by precipitation (e.g. TCA precipitation, immunoprecipitation, etc.), immobilization (e.g. on a solid substrate), followed by washing. The bound protein is conveniently detected by taking advantage of a detectable label attached to it, e.g. by measuring radioactive emission, optical or electron density, or by indirect detection using, eg. antibody conjugates.

For example, a method of screening for suitable fused antagonists and/or agonists could involve the application of agents present in the fused activating Gli reporter assay described in the Examples. Such a screening assay could compare in situ hybridization in the presence and absence of the candidate antagonist and/or agonist in a fused expressing tissue as well as confirmation or absence of fused modulated cellular development. Typically these methods involve exposing an immobilized fused to a molecule suspected of binding thereto and determining binding or phosphorylation of the molecule to the immobilized fused and/or evaluating whether or not the molecule activates (or blocks activation of) fused. In order to identify such fused binding ligands, fused can be expressed on the surface of a cell and used to screen libraries of synthetic candidate compounds or naturally-occurring compounds (e.g., from endogenous sources such as serum or cells).

Suitable molecules that affect the protein-protein interaction of fused and its binding proteins include fragments of the latter or small molecules, e.g., peptidomimetics, which will prevent interaction and proper complex formation. Such small molecules, which are usually less than 10K molecular weight, are preferable as therapeutics since they are more likely to be permeable to cells, are less susceptible to degradation by various cellular mechanisms, and are not as apt to elicit an immune response as proteins. Small molecules include but are not limited to synthetic organic or inorganic compounds. Many pharmaceutical companies have extensive libraries of such molecules, which can be conveniently screened by using the assays of the present invention. Non-limiting examples include proteins, peptides, glycoproteins, glycopeptides, glycolipids, polysaccharides, oligosacchardies, nucleic acids, bioorganic molecules, peptidomimetics, pharmacological agents and their metabolites, transcriptional and translation control sequences, and the like.

A preferred technique for identifying molecules which bind to fused utilizes a chimeric substrate (e.g., epitope-tagged fused or fused immunoadhesin) attached to a solid phase, such as the well of an assay plate. The binding of the candidate molecules, which are optionally labeled (e.g., radiolabeled), to the immobilized receptor can be measured. Alternatively, competition for activation of Gli can be measured. In screening for antagonists and/or agonists, fused can be exposed to a fused substrate followed by the putative antagonist and/or agonist, or the fused binding protein and antagonist and/or agonist can be added simultaneously, and the ability of the antagonist and/or agonist to block fused activation can be evaluated.

(2) Detection assays

The fused polypeptides are useful in assays for identifying lead compounds for therapeutically active agents that modulate fused hedgehog signaling. Specifically, lead compounds that either prevent the formation of fused signaling complexes or prevent or attenuate fused modulated hedgehog signaling (e.g, binding to fused itself or to a substrate) can be conveniently identified.

Various procedures known in the art may be used for identifying, evaluating or assaying the inhibition of activity of the fused proteins of the invention. As fused is believed to operate in a similar manner as other kinases, techniques known for use with identifying kinase/phosphatase modulators may also be employed with the present invention. In general, such assays involve exposing target cells in culture to the compounds and a) biochemically analyzing cell lysates to assess the level and/or identity of phosphorylation; or (b) scoring phenotypic or functional changes in treated cells as compared to control cells that were not exposed to the test substance. Such screening assays are described in U.S. Pat. No. 5,602171, U.S. Pat. No. 5,710,173, WO 96/35124 and WO 96/40276.

(a) Biochemical detection techniques

Biochemical analysis techniques can be evaluated by a variety of techniques. One typical assay mixture which can be used with the present invention contains fused and a protein with which fused is normally associated (e.g. Gli), usually in an isolated, partially pure or pure form. One or both of these components may be fused to another peptide or polypeptide, which may, for example, provide or enhance protein—protein binding, improve stability under assay conditions, etc. In addition, one of the components usually comprises or is coupled to a detectable label. The label may provide for direct detection by measuring radioactivity, luminescence, optical or electron density, etc., or indirect detection such as an epitope tag, an enzyme, etc. The assay mixture can additionally comprise a candidate pharmacological agent, and optionally a variety of other components, such as salts, buffers, carrier proteins, e.g. albumin, detergents, protease inhibitors, nuclease inhibitors, antimicrobial agents, etc., which facilitate binding, increase stability, reduce non-specific or background interactions, or otherwise improve the efficiency or sensitivity of the assay.

The following detection methods may also be used in a cell-free system wherein cell lysate containing the signal transducing substrate molecule and fused is mixed with a compound of the invention. The substrate is phosphorylated by initiating the kinase reaction by the addition of adenosine triphosphate (ATP). To assess the activity of the compound, the reaction mixture may be analyzed by the SDS-PAGE technique or it may be added to substrate-specific anchoring antibody bound to a solid support, and a detection procedure as described above is performed on the separated or captured substrate to assess the presence or absence of pSer/Thr. The results are compared to those obtained with reaction mixtures to which the compound is not added. The cell-free system does not required the natural ligand or knowledge of its identity. The cell-free system does not require mixtures to which the compound is not added. The cell-free system does not require the natural ligand or knowledge of its identity. For example, Posner et al. (U.S. Pat. No. 5,155,031 describes the use of insulin receptor as a substrate and rat adipocytes as target cells to demonstrate the ability of pervanadate to inhibit PTP activity. Another example, Burke et al., $Biochem.\ Biophys.\ Res.\ Comm.$ 204:129–134 (1994) describes the use of autophosphorylated insulin receptor and recombinant PTP1B in assessing the inhibitory activity of a phophotyrosyl mimetic.

(i) Whole cell detection

A common technique involves incubating cells with vertebrate fused and radiolabeled phosphate, lysing the cells, separating cellular protein components of the lysate using an SDS-polyacrylamide gel (SDS-PAGE) technique, in either one or two dimensions, and detecting the presence of phosphorylated proteins by exposing X-ray film. Detection can also be effected without using radioactive labeling. In such a technique, the protein components (e.g., separated by SDS-PAGE) are transferred to a nitrocellulose membrane where the presence of phosphorylated serine/threonines is detected using an antiphosphoserine/threonine antibody (anti-pS/T).

Alternatively, the anti-pS/T can be conjugated with an enzyme, such as horseradish peroxidase, and detected by subsequent addition of a colorimetric substrate for the enzyme. A further alternative involves detecting the anti-PS/T by reacting with a second antibody that recognizes the anti-PS/T, this second antibody being labeled with either a radioactive moiety or an enzyme as previously described. Examples of these and similar techniques are described in Hansen et al., $Electrophoresis$ 14: 112–126 (1993); Campbell et al., $J.\ Biol.\ Chem.$ 268: 7427–7434 (1993); Donato et al., $Cell\ Growth\ Diff.$ 3: 258–268 (1992); Katagiri et al., $J.\ Immunol.$ 150: 585–593 (1993). Additionally, the anti-pS/T can be detected by labeling it with a radioactive substance, followed by scanning the labeled nitrocellulose to detect radioactivity or exposure of X-ray film.

(ii) Kinase assays

When the screening methods of the present invention for fused antagonists/agonists are carried out as an ex vivo assay, the target kinase (e.g. fused) can be a substantially purified polypeptide. The kinase substrate (e.g., MBP, Gli) is a substantially purified substrate, which in the assay is phosphorylated in a reaction with a substantially purified phosphate source that is catalyzed by the kinase. The extent of phosphorylation is determined by measuring the amount of substrate phosphorylated in the reaction. A variety of possible substrates may be used, including the kinase itself in which instance the phosphorylation reaction measured in the assay is autophosphorylation. Exogenous substrates may also be used, including standard protein substrates such as myelin basic protein (MBP); yeast protein substrates; synthetic peptide substrates, and polymer substrates. Of these, MBP and other standard protein substrates may be regarded as preferred (see Example 10). Other substrates may be identified, however, which are superior by way of affinity for the kinase, minimal perturbation of reaction kinetics, possession of single or homogenous reaction sites, ease of handling and post-reaction recover, potential for strong signal generation, and resistance or inertness to test compounds.

Measurement of the amount of substrate phosphorylated in the ex vivo assay of the invention may be carried out by means of immunoassay, radioassay or other well-known methods. In an immunoassay measurement, an antibody (such as a goat or mouse anti-phosphoserine/threonine antibody) may be used which is specific for phosphorylated moieties formed during the reaction. Using well-known ELISA techniques, the phosphoserine/threonine antibody complex would itself be detected by a further antibody linked to a label capable of developing a measurable signal (as for example a fluorescent or radioactive label). Additionally, ELISA-type assays in microtitre plates may be used to test purified substrates. Peraldi et al, *J. Biochem.* 285: 71–78 (1992); Schraag et al., *Anal. Biochem.* 211: 233–239 (1993); Cleavland, *Anal. Biochem.* 190: 249–253 (1990); Farley, *Anal. Biochem.* 203: 151–157 (1992) and Lozaro, *Anal. Biochem.* 192: 257–261 (1991).

For example, detection schemes can measure substrate depletion during the kinase reaction. Initially, the phosphate source may be radiolabeled with an isotope such as $^{32}$P or $^{33}$P, and the amount of substrate phosphorylation may be measured by determining the amount of radiolabel incorporated into the substrate during the reaction. Detection may be accomplished by: (a) commercially available scintillant-containing plates and beads using a beta-counter, after adsorption to a filter or a microtitre well surface, or (b) photometric means after binding to a scintillation proximity assay bead or scintillant plate. Weernink and Kiijken, *J. Biochem. Biophs. Methods* 31: 49, 1996; Braunwalder et al., *Anal. Biochem.* 234: 23 (1996); Kentrup et al., *J. Biol. Chem.* 271: 3488 (1996) and Rusken et al., *Meth. Enzymol.* 200: 98 (1991).

Preferably, the substrate is attached to a solid support surface by means of non-specific or, preferably, specific binding. Such attachment permits separation of the phosphorylated substrate from unincorporated, labeled phosphate source (such as adenosine triphosphate prior to signal detection. In one embodiment, the substrate may be physically immobilized prior to reaction, as through the use of Nunc™ high protein binding plate (Hanke et al., *J. Biol. Chem.* 271: 695 (1996)) or Wallac ScintiStrip™ plates (Braunwalder et al., *Anal. Biochem.* 234: 23 (1996). Substrate may also be immobilized after reaction by capture on, for example, P81 phophocellulose (for basic peptides), PEI/ acidic molybdate resin or DEAE, or TCA precipitation onto Whatman™ 3MM paper, Tiganis et al., *Arch. Biochem. Biophys.* 325: 289 (1996), Morawetz et al., *Mol. Gen. Genet.* 250; 17 (1996); Budde et al, *Int J. Pharmacognosy* 33: 27 (1995) and Casnellie, *Meth. Enz.* 200: 115 (1991). Yet another possibility is the attachment of the substrate to the support surface, as by conjugation with binding partners such as glutathione and streptavidin (in the case of GST and biotin), respectively) which have been attached to the support, or via antibodies specific for the tags which are likewise attached to the support.

Further detection methods may be developed which are preferred to those described above. Especially for use in connection with high-throughput screening, it is expected that such methods would exhibit good sensitivity and specificity, extended linear range, low background signal, minimal fluctuation, compatibility with other reagents, and compatibility with automated handling systems.

The in vivo efficacy of the treatment of the present invention can be studied against chemically induced tumors in various rodent models. Tumor cell lines propagated in in vitro cell cultures can be introduced in experimental rodents, e.g. mice by injection, for example by the subcutaneous route. Techniques for chemical inducement of tumors in experimental animals are well known in the art.

(b) Biological detection techniques:

The ability of the antagonist/agonist compounds of the invention to modulate the activity fused, which itself modulates hedgehog signaling, may also be measured by scoring for morphological or functional changes associated with ligand binding. Any qualitative or quantitative technique known in the art may be applied for observing and measuring cellular processes which comes under the control of fused. The activity of the compounds of the invention can also be assessed in animals using experimental models of disorders caused by or related to dysfunctional hedgehog signaling. For example, ineffective DHh hedgehog signaling in mice leads to viable but sterile mice. The effects of mutant fused (hfused-DN) also affects gut development, which is regulated by IHh expression. Additionally, proper SHh signaling is critical to murine embryonic development at the notochord and floor plate, neural tube, distal limb structures, spinal column and ribs. Improper SHh signaling, is also correlative with cyclopia. Any of these phenotypic properties could be evaluated and quantified in a screening assay for fused antagonists and/or agonist. Disease states associated with overexpression of hedgehog is associated with basal cell carcinoma while inactive sonic hedgehog signaling leads to improper neural development.

The data obtained from these cell culture assays and animal studies can be used in formulating a range of dosages for use in humans. The dosage of the compounds of the invention should lie within a range of circulating concentrations with little or no toxicity. The dosage may vary within this range depending on the dosage form employed and the route of administration.

(2) Antisense nucleotides

Another preferred class of antagonists involves the use of gene therapy techniques, include the administration of antisense nucleotides. Applicable gene therapy techniques include single or multiple administrations of therapeutically effective DNA or mRNA. Antisense RNAs and DNAs can be used as therapeutic agents for blocking the expression of certain genes in vivo. Short antisense oligonucleotides can be imported into cells where they act as inhibitors, despite their low intracellular concentrations caused by restricted uptake by the cell membrane, Zamecnik et al., *Proc. Natl. Acad. Sci. USA* 83: 4143–4146 (1986). The oligonucleotides can be modified to enhance their uptake, e.g., by substituting their negatively charged phosphodiester groups by uncharged groups.

There are a variety of techniques known for introducing nucleic acids into viable cells. The techniques vary depending upon whether the nucleic acid is transferred into cultured cells in vitro, ex vivo, or in vivo in the cells of the intended host. Techniques suitable for the transfer of nucleic acid into mammalian cells in vitro include the use of liposomes, electroporation, microinjection, cell fusion, DEAE-dextran, the calcium phosphate precipitation method, etc. The currently preferred in vivo gene transfer techniques include transfection with viral (typically retroviral) vectors and viral coat protein-liposome mediated transfection, Dzau et al., *Trends Biotech.* 11: 205–210 (1993). In some situations it is desirable to provide the nucleic acid source with an agent that targets the target cells, such as an antibody specific for a cell surface membrane protein associated with endocytosis may be used for targeting and/or to facilitate uptake, e.g., capsid proteins or fragments thereof tropic for a particular cell type, antibodies for proteins which undergo internalization in cycling, and proteins that target intracellular localization and enhance intracellular half-life. The technique of receptor-mediated endocytosis is described, for example, by Wu et al., *J. Biol. Chem.* 262: 4429–4432 (1987); Wagner et al., *Proc. Natl. Acad. Sci. USA* 87: 3410–3414 (1990). For a review of known gene marking and gene therapy protocols, see Anderson et al., *Science* 256: 808–813 (1992).

In one embodiment, fused antagonist and/or agonist molecules may be used to bind endogenous ligand in the cell, thereby causing the cell to be unresponsive to fused wild type, especially when the levels of fused in the cell exceed normal physiological levels. Also, it may be beneficial to bind endogenous fused substrates or complexing agents that are activating undesired cellular responses (such as proliferation of tumor cells).

In a further embodiment of the invention, fused expression may be reduced by providing fused-expressing cells with an amount of fused antisense RNA or DNA effective to reduce expression of the fused protein.

I. Diagnostic Uses

Another use of the compounds of the invention (e.g., human and vertebrate fused, vertebrate fused variant and anti-vertebrate fused antibodies) described herein is to help diagnose whether a disorder is driven, to some extent, fused or hedgehog signaling. For example, basal cell carcinoma cells are associated with active hedgehog signaling.

A diagnostic assay to determine whether a particular disorder is driven by hedgehog signaling, can be carried out using the following steps: (1) culturing test cells or tissues; (2) administering a compound which can inhibit fused modulated hedgehog signaling; and (3) measuring the degree of kinase attenuation on the fused substrate in cell lysates or hedgehog mediated phenotypic effects in the test cells. The steps can be carried out using standard techniques in light of the present disclosure. For example, standard techniques can be used to isolate cells or tissues and culturing or in vivo.

Compounds of varying degree of selectivity are useful for diagnosing the role of fused. For example, compounds which inhibit fused in addition to another form of kinase can be used as an initial test compound to determine if one of several serine/threonine kinases drive the disorder. The selective compounds can then be used to further eliminate the possible role of the other serine/threonine kinases in driving the disorder. Test compounds should be more potent in inhibiting serine/threonine kinase activity than in exerting a cytotoxic effect (e.g., an $IC_{50}/LD_{50}$ of greater than one). The $IC_{50}$ and $LD_{50}$ can be measured by standard techniques, such as an MTT assay, or by measuring the amount of LDH released. The degree of $IC_{50}/LD_{50}$ of a compound should be taken into account in evaluating the diagnostic assay. Generally, the larger the ratio the more relative the information. Appropriate controls take into account the possible cytotoxic effect of a compound, such as treating cells not associated with a cell proliferative disorder (e.g., control cells) with a test compound, can also be used as part of the diagnostic assay. The diagnostic methods of the invention involve the screening for agents that modulate the effects of fused upon hedgehog signaling. Exemplary detection techniques include radioactive labeling and immunoprecipitating (U.S. Pat. No. 5,385,915).

The following examples are offered for illustrative purposes only, and are not intended to limit the scope of the present invention in any way.

All patent and literature references cited in the present specification are hereby incorporated by reference in their entirety.

EXAMPLES

Commercially available reagents referred to in the examples were used according to manufacturer's instructions unless otherwise indicated. The source of those cells identified in the following examples, and throughout the specification, by ATCC accession numbers is the American Type Culture Collection, Rockville, Md.

EXAMPLE 1

Isolation of human fused cDNA clones

An expressed sequence tag (EST) DNA database (LIFESEQ™, Incyte Pharmaceuticals, Palo Alto, Calif.) was searched for a human homologue of the Drosophila segment polarity gene fused (SEQ ID NO:26) (Preat et al., Nature 347: 87–9 (1990)). The EST Incyte #2515662 (FIG. 2 (SEQ ID NO:3)) was identified as a potential candidate. In order to identify human cDNA libraries containing human fused clones, human cDNA libraries in pRK5 were first screened by PCR using the following primers:

h-FUSED.f (SEQ ID NO:8) 5'-CAATACAATGGTGCTGACATCCATCAAAGGCA-3' h-FUSED.r (SEQ ID NO:9) 5'-'GAAGGGAGGGGTGCCTACTGCCA-3'

A fetal lung library was selected and enriched for fused cDNA clones by extension of single stranded DNA from plasmid libraries grown in dug⁻/bung⁻ host using the h-FUSED.f primer in a reaction containing 10 μl of 10× PCR Buffer (Perkin Elmer), 1 μl dNTP (20 mM), 1 μl library DNA (200 ng), 0.5 ml primer, 86.5 μl H₂O and 1 μl of Amplitaq® (Perkin Elmer) added after a hot start. The reaction was denatured for 1 min. at 95° C., annealed for 1 min. at 60° C. then extended for 20 min. at 72° C. DNA was extracted with phenol/CHCl₃, ethanol precipitated, then transformed by electroporation into DH10B host bacteria. Colonies from each transformation were plated and lifted on nylon membranes and screened with an oligo probe derived from the EST sequence of the following sequence:

h-FUSED.p (SEQ ID NO:10) 5'-CTCCAGCTCTGGAGACATATAGAGTGGTGTG CCTTTGA-3'

Figure 5C:
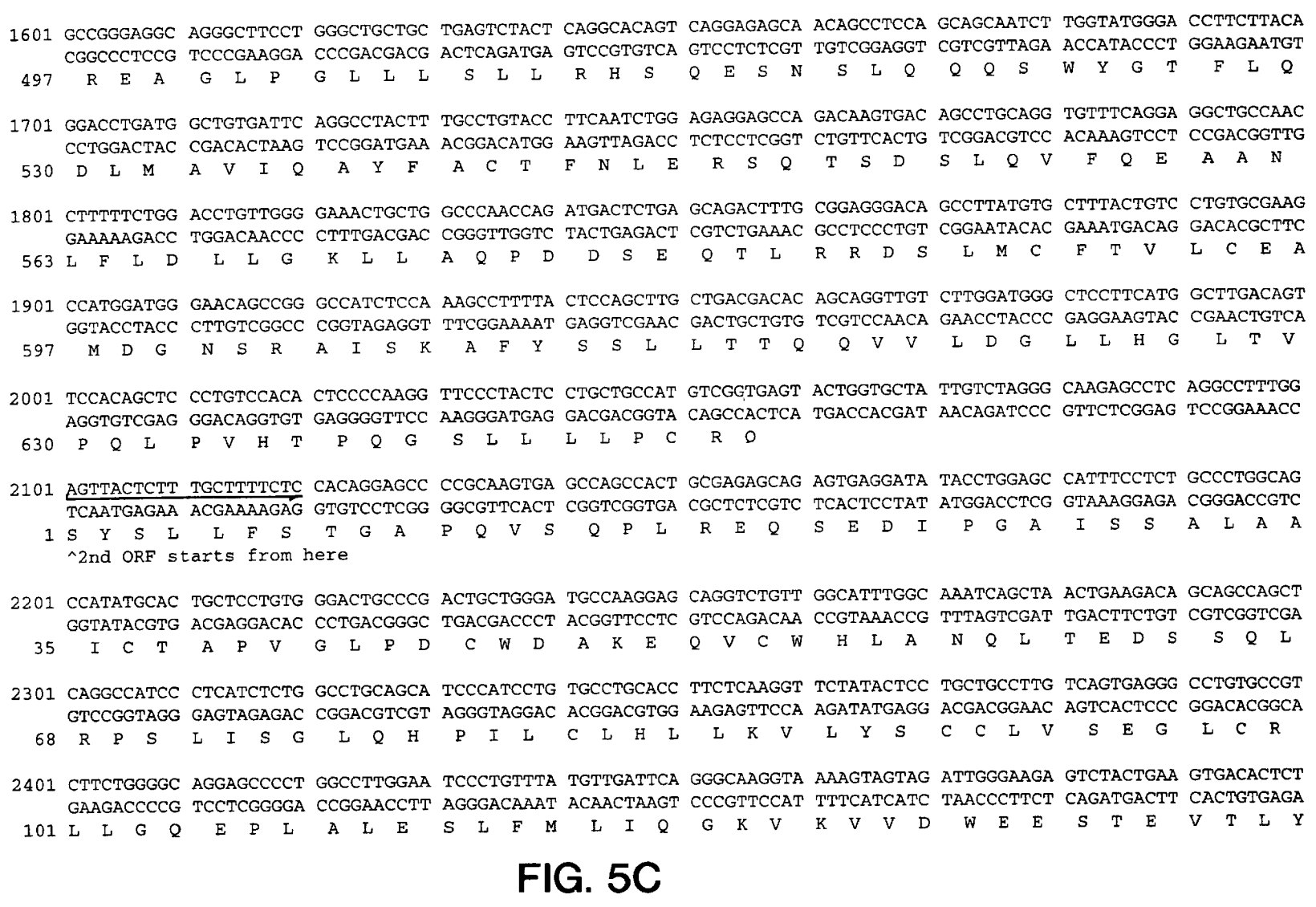

The oligo probe was labeled with [γ-³²P]-ATP and T4 polynucleotide kinase. Filters were hybridized overnight at 42° C. in 50% formamide, 5× SSC, 10× Denhardt's, 0.05M sodium phosphate (pH 6.5), 0.1% sodium pyrophosphate, 50 μg/ml of sonicated salmon sperm DNA. The filters were then rinsed in 2× SSC and washed in 0.1× SSC, 0.1% SDS then exposed to Kodak® X Ray films. Two positive clones (DNA28494 and DNA28495–FIGS. 4 & 5 (SEQ ID NOS:6 and 4), respectively) containing an insert of approximately 5 kb were isolated and sequenced. The sequence of clone DNA28495 (SEQ ID NO:4) contains a potential initiation methionine at position 116 followed by an open reading frame of 1944 bp (FIG. 4). However, this open reading frame (ORF) encodes a protein that is only 648 amino acids long, somewhat shorter than the 795 amino acid sequence of the Drosophila fused. Interestingly, a second open reading frame is present in the 3' region of the cDNA, from nucleotide 2295 to 4349 (FIG. 4), which suggests that the cDNA may have been improperly spliced and that an intron remains between the 2 ORFs, or correspond to an alternatively spliced variant of fused. The sequence of clone DNA28494 (SEQ ID NO:6) is very similar. There is one nucleotide difference between clone DNA28495 (SEQ ID NO:4) and clone DNA28494 (SEQ ID NO:6) located in the first ORF at position 1863 of clone 28495 (A vs. G) which changes the coding sequence from an Gln to a Arg at position 583. (FIG. 4). This change is likely due to an allelic variation. The first open reading frame of DNA28494 (SEQ ID NO:6) starts at residue 115 and is followed by a 647 amino acid long open reading frame. The sequences are identical except for the one change described above at position 583 and for the last 9 residues in the first open reading frame.

EXAMPLE 2

Expression of fused clones

In order to determine the size of the protein expressed from the cDNA corresponding to DNA28495 and DNA28494 (SEQ ID NOS:4 and 6), respectively, an HA epitope tag was inserted at the N-terminus of the protein by PCR using the following primers:

Hfus.Cla-HA.F: (SEQ ID NO: 11) 5'-CCATCGATGTACCCATACGACGTCCCAGACT ACGCTGAAAAGTACCACGTGTTGGAGATG-3' and hFus.Xba.R: (SEQ ID NO: 12) 5'-GCTCTAGACTAAGGGGCAGGTCCTGTGTTCTG-3'.

The PCR product was purified, digested with ClaI-SmaI and subcloned into the pRK5 plasmids containing DNA28494 and DNA28495 (SEQ ID NO:6 and 4), respectively . DNA from each of the constructs was transfected overnight into 293 cells using the CaPO4 method (Sambrook et al, supra; Ausuble et al., supra). After about 24 h. to 48 h. after transfection, the cells were harvested and the cell pellet was lysed in 1 ml of lysine buffer (50 mM Tris pH 8.0, 150 mM NaCl, 1 mM EDTA, 1% NP40, Aprotinin, Leupeptin, -PMSF, 1 mM NaF and 1 mM Sodium Vanadate) for 20 min at 4° C. The extract was spun for 10 min at 10K then the supernatant was transferred to a new tube and precleared with 20 μl Protein A sepharose for 1 h. The protein A sepharose was spun down and 1 μl of anti-HA antibody (5 μg, Boehringer) was added to each tube. After overnight incubation at 4° C., 30 μl of Protein G sepharose was added and the tubes incubated at 4° C. for 1 hour. The protein G beads were then sun down for 1 min., washed 3 times with lysis buffer, resuspended in 20 μl of laemli buffer in the presence of β-mercapto ethanol. Samples were denatured for 5 min. at 100° C. then loaded on a 6% polyacrylamide gel. Proteins were then transferred to nitrocellulose and analyzed by Western blot using the same anti-HA antibody overnight at 1 μg/ml in blocking buffer (PBS, 0.5% Tween®, 5% non fat dry milk, 3% goat serum followed by an anti-mouse HRP. ECL was used for the detection and the membrane was exposed for 90 seconds to X-Ray films. A specific band of 150 kDa was detected in the cell pellet of cells transfected with the construct corresponding to clone DNA28494 (SEQ ID NO:6) and a specific band of approximately 100 kDa could be detected for clone DNA28495 (SEQ ID NO:4) (FIG. 6). These bands were not present in the mock transfected control. The presence of the 150 kDa band suggests the two open reading frames of DNA28494 (SEQ ID NO:6) can be spliced together to direct the synthesis of a large protein of 150 kDa. The absence of this band for DNA28495 (SEQ ID NO:4) suggested that this clone apparently cannot be correctly spliced. Alternative splicing of the fused gene seems to lead to the production of several different products and may be a mechanism or regulation of fused activity. Specific regions at the C-terminus of the Drosophila fused protein is known to be required for the activity of the molecule, Therond et al., *Genetics* 142: 1181–1198 (1996); Robbins et al., *Cell* 90: 225–234 (1997). Shorter fused molecules truncated at the C-terminus may therefore correspond to inactive or to dominant negative forms of the molecule.

EXAMPLE 3

Northern Blots

Figure 7:
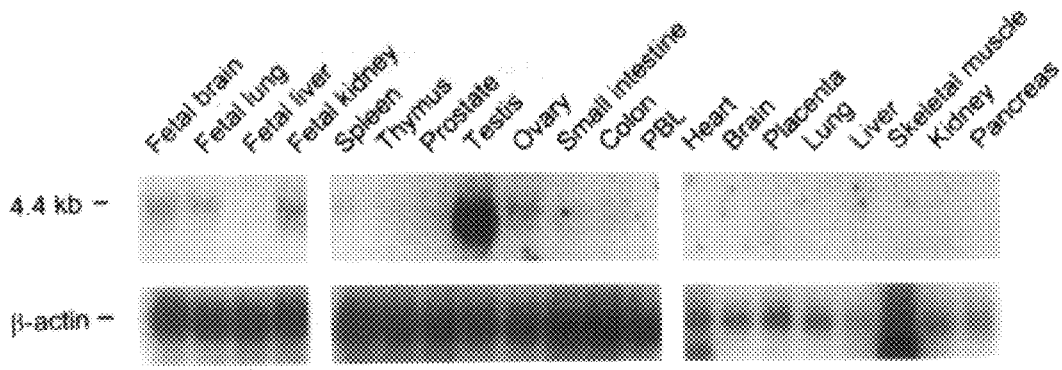
FIG. 7 is a northern blot analysis of human fused (SEQ ID NO: 1). Multiple human fetal and adult tissue northern blots were probes with a human fused (SEQ ID NO:1) cDNA probe.
Figure 8A:
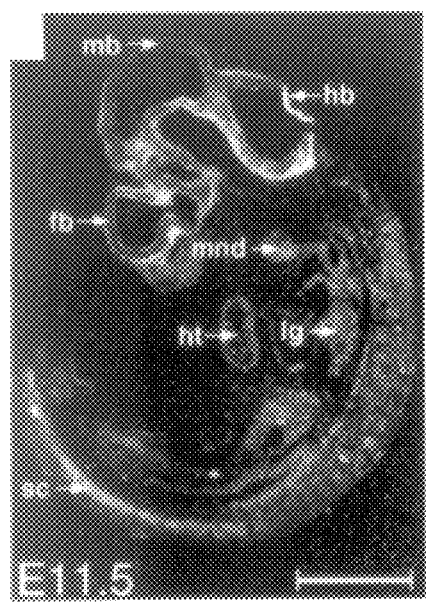
FIGS. 8A–8F are photographs showing in situ hybridization of embryonic and adult tissues with fused (SEQ ID NO:1). Sagittal sections of E11.5 (FIG. 8A) and E13.5 (FIG. 8B) mouse embryos. Coronal section through the spinal chord of E11.5 (FIG. 8C) and E13.5 (FIG. 8D) mouse embryo. Sagittal section through P1 (FIG. 8E) and adult (FIG. 8F) mouse. Cp, choroid plexus; hb, hindbrain; hip, hippocampal formation; ht, heart; hy, hypothalamus; kd, kidney; lg, lung; mb, midbrain; md, midgut; mnd, mandibular component of first branchial arch; sc, spinal cord; st, stomach; tec, midbrain tectum; vh, ventral horn of spinal cord; vm, ventral midbrain. Scale bars.
Figure 8B:
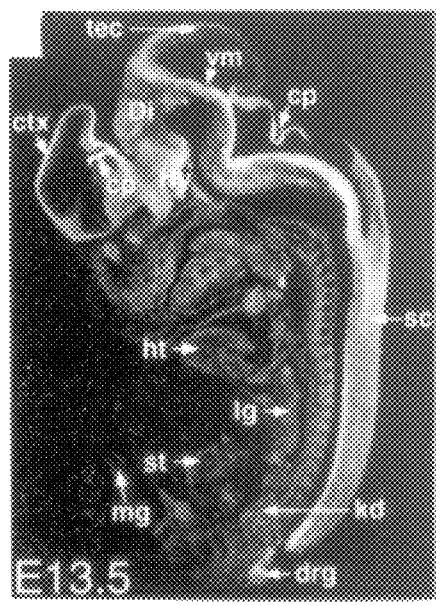
Figure 8C:
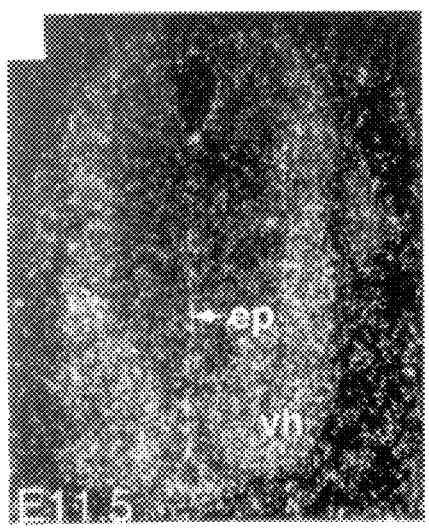
Figure 8D:
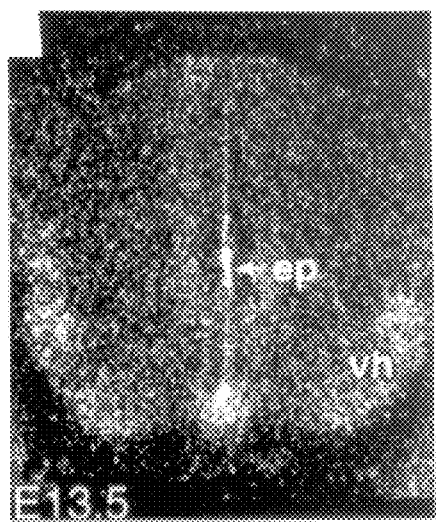
Figure 8E:
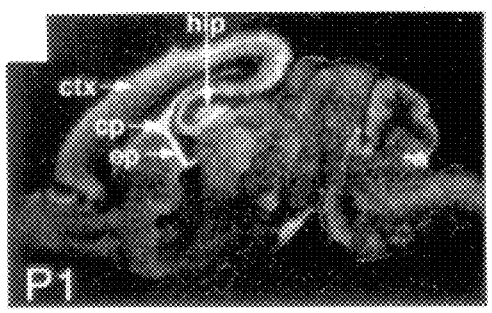
Figure 8F:
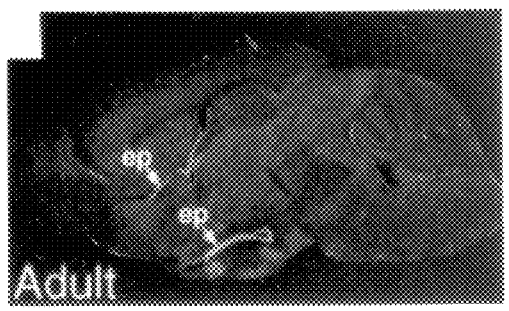

In order to determine the best tissue source to isolate more fused cDNAs and to identify a transcript encoding a full length 150 kDa fused molecule, human multiple tissue northern blots I, II and fetal blot from Clontech were probed with a 1.6 kb, ClaI-AccI fragment derived from clone DNA28494 (SEQ ID NO:6) labeled by random priming. The blots were hybridized in 50% formamide, 5× SSC, 10× Denhardt's, 0.05M Sodium phosphate (pH 6.5), 0.1% Sodium pyrophosphate, 50 mg/ml sonicated salmon sperm DNA, all in the presence of 1×10$^6$ cpm/ml $^{32}$P-labeled probe at 42° C. overnight. The blots were washed in 2× SSC at RT for 10 minutes and washed in 0.2× SSC/0.1% SDS at 42° C. for 30 minutes then exposed to x-ray film overnight. FIG. 7 shows that the fused message is expressed at high levels in testis and at low levels in most other tissues, including fetal tissues. (FIG. 7).

EXAMPLE 4

PCR on different tissues to identify the correct splice form

In order to isolate a cDNA where the 2 potential ORFs were spliced together correctly, we designed the following primers flanking the potential intron and amplified various tissues including human fetal brain, brain, keratinocyte, testis, ovary, fetal liver, and lung templates.

F 1 (SEQ ID NO:13) 5'-CTGACGACACAGCAGGTTGTC-3'

R 4 (SEQ ID NO:14) 5'-CAGATGCTTCAGGATGGACAT-3'

Two microliters of each cDNA library was used as the template and PCR was done with Klentaq® polymerase. PCR was performed for 45 cycles of amplification with 94° C. denaturation for 1 min., 55° C. annealing for 1 min., and 68° C. extensions for 2 min. One fifth of the reaction was loaded on 1% agarose gel and was Southern blotted. The blot was hybridized overnight with full-length fused probe labeled by random priming as described for the Northern blot.

A 1 kb PCR fragment was identified in fetal brain, testis and ovary. This fragment was gel-purified and subjected to direct PCR sequencing using both the F1 and R4 primer identified above as well a the following primers:

hf16 (SEQ ID NO:15) 5'-AGAGTAGCAACGTCACTGC-3' hf8 (SEQ ID NO:16) 5'-CCTCACTGACAAGGCAGCAGG-3' hf19 (SEQ ID NO: 17) 5'-CCCGAGGAGGCATCTGCACAG-3'

The sequence of this 1 kb fragment revealed that intron sequences were absent and that the 2 ORFs were connected together in the same reading frame. The sequence of the correctly spliced sequence is shown in FIG. 1 (SEQ ID NO:1). The initiator ATG is present at position 161 and is followed by an ORF of 3945 nucleotides which encodes a 1315 amino acid long protein with a predicted molecular weight of 144 kDa.

The overall similarity with Drosophila fused (SEQ ID NO:23) is 28% (FIG. 2). The N-terminal 263 amino acid domain of the protein containing the kinase domain is 55% homologous to the Drosophila fused kinase domain. The remaining 1052 amino acids portion of the protein is not appreciably homologous to other known proteins and, interestingly, is not homologous to the corresponding region in Drosophila fused. Interestingly, this region of non-homology includes the very C-terminus of the fly protein which appears to be required for activity, Robbins et al., *Cell* 90: 225–34 (1997); Therond et al., *Genetics* 142: 1181–98 (1996). The improperly spliced cDNAs described above may reflect alternative splicing of the fused gene which leads to the production of a molecule with a truncated C-terminus and may be a mechanism to regulate fused activity.

EXAMPLE 5

Reconstitution of the correctly spliced full length human fused

The fused clone DNA28495 was subcloned from the pRK5B plasmid into pRK5.tkneo using ClaI-HindIII. PCR was performed using human testis cDNA as a template and the primers hf3 (SEQ ID NO:18) (CAGAACTTCAGGTCCTAAAGG) and R4 (sequence see above, Example 4). PCR conditions were 45 cycles of (94° C., 1 min, 46° C. to 68° C. temperature gradient annealing for 1 min, and 68° C., 4 min). The PCR fragment was digested with AccI and ligated in the pRK5.tkneo.fused plasmid cut with AccI in order to replace the region containing the intron with the correct spliced form. Two subclones were sequenced between the two AccI site and had the same correct sequence.

EXAMPLE 6

In situ hybridization

E11.3 and E13.5 mouse embryos were immersion-fixed overnight at 4° C. in 4% paraformaldehyde, cryoprotected overnight in 15% sucrose, embedded in O.T.C. and frozen on liquid nitrogen. Adult mouse brains were fresh frozen with powdered dry ice. P1 mouse brains, adult mouse testis and adult rat spinal cords were embedded in O.T.C. and frozen on liquid nitrogen. Sections were cut at 16 mm, and processed for in situ hybridization for fused by the method of Phillips et al.. *Science* 250: 290–294 (1990). RNA probes were labeled with $^{33}$P-UTP as described by Melton et al., *Nucleic Acids Res.* 12: 7035–7052 (1984). Sense and antisense probes were synthesized from a mouse fused DNA fragment using T3 and T7, respectively, corresponding to the region encoding amino acid residues 317–486 of the human sequence.

FIG. 8 reveals that the mouse fused mRNA is widely distributed in SHh responsive tissues, including the neural tube, pre-somitic mesoderm, somites, developing limb buds and skin. Transcripts for fused were also found in the embryonic gut, testis, cartilage and muscle—Tissues that are exposed to the other members of the Hh protein family; Desert and Indian. In the E11-5 mouse nervous system, high levels of fused transcripts were detected throughout the forebrain, midbrain, hindbrain and spinal cord. These high levels of expression were retained in embryonic day 13.5. In both embryonic days 11.5 and 13.5, fused mRNA was detected mainly in the ventral aspect of the neural tube, in regions that are likely to be exposed to the ventral midline-derived SHh. By post natal day −1, widespread expression of fused is still maintained throughout the brain with high levels of transcripts detected in the cortex, hypocampus, ependima and choroid plexus. In the adult, low levels of fused expression are detected all through the brain with higher levels confined to the ependima.

The tissue distribution of fused and the Hh receptor components, Smo and Ptch show considerable overlap. All of them are initially expressed through the neural tube as well as in other Hh responsive tissues. However, whereas Smo mRNA was evenly distributed along the dorso-ventral axis, Ptch and fused mRNAs are found at higher levels ventrally, suggesting that they may be upregulated by Hh. In addition while by day E12, expression of both Smo and Ptch is found mainly in cells which are in close proximity to the ventricular zone, fused mRNA is still widely expressed and its levels decline only later. In the adult expression of both Smo and fused is confined to the ependima where neurogenesis continues.

Figure 9A:
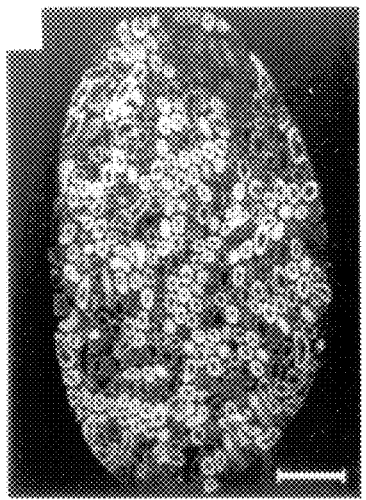
FIGS. 9A–9C are photographs showing in situ hybridization showing the presence of fused mRNA in high levels in the adult mouse testes.
Figure 9B:
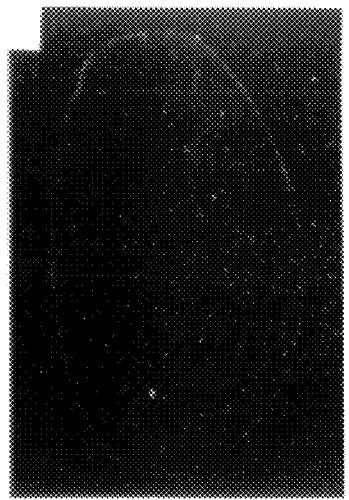
Figure 9C:
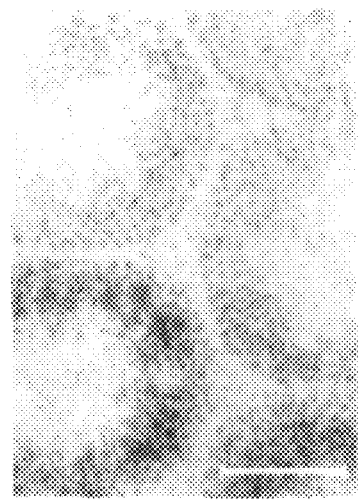
Figure 10A:
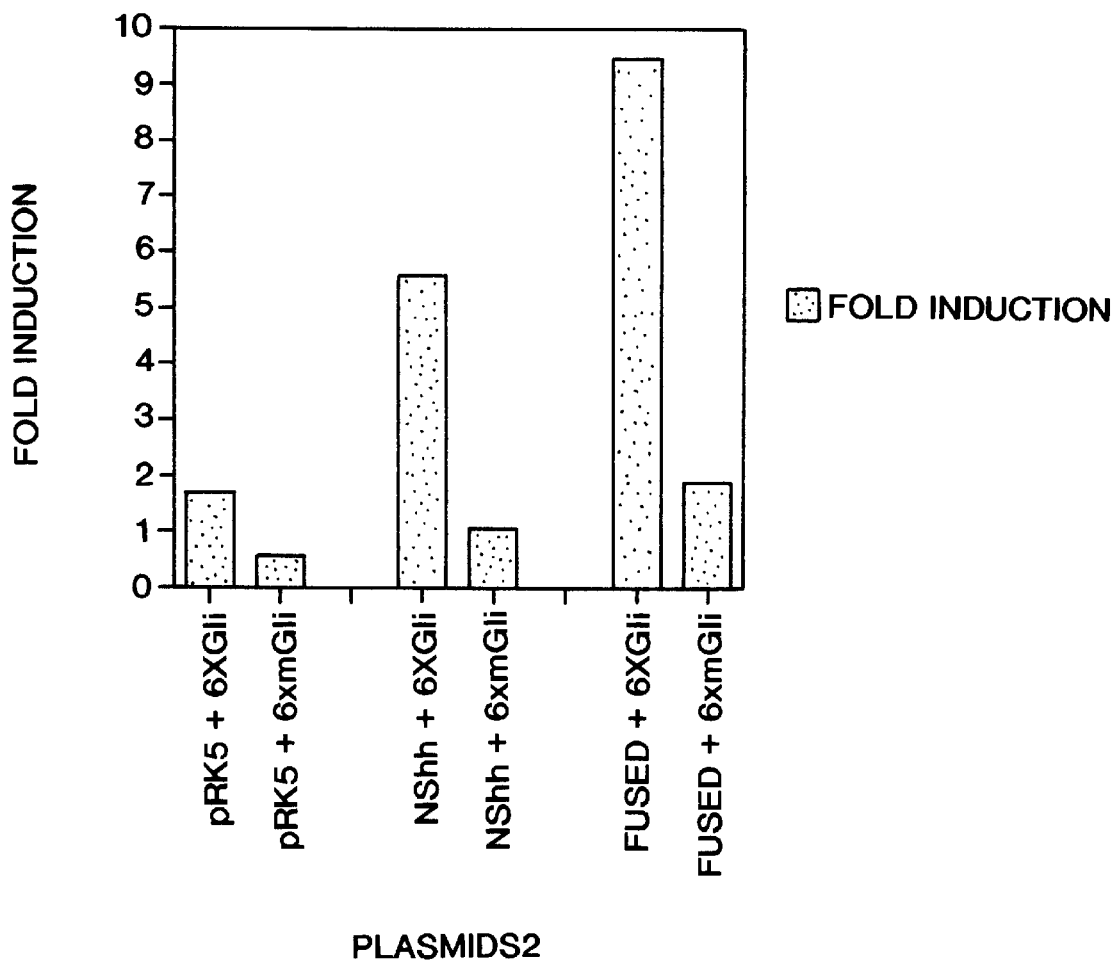
Figures 10A–10B are bar graphs representing the activation of Gli by fused.
Figure 10B:
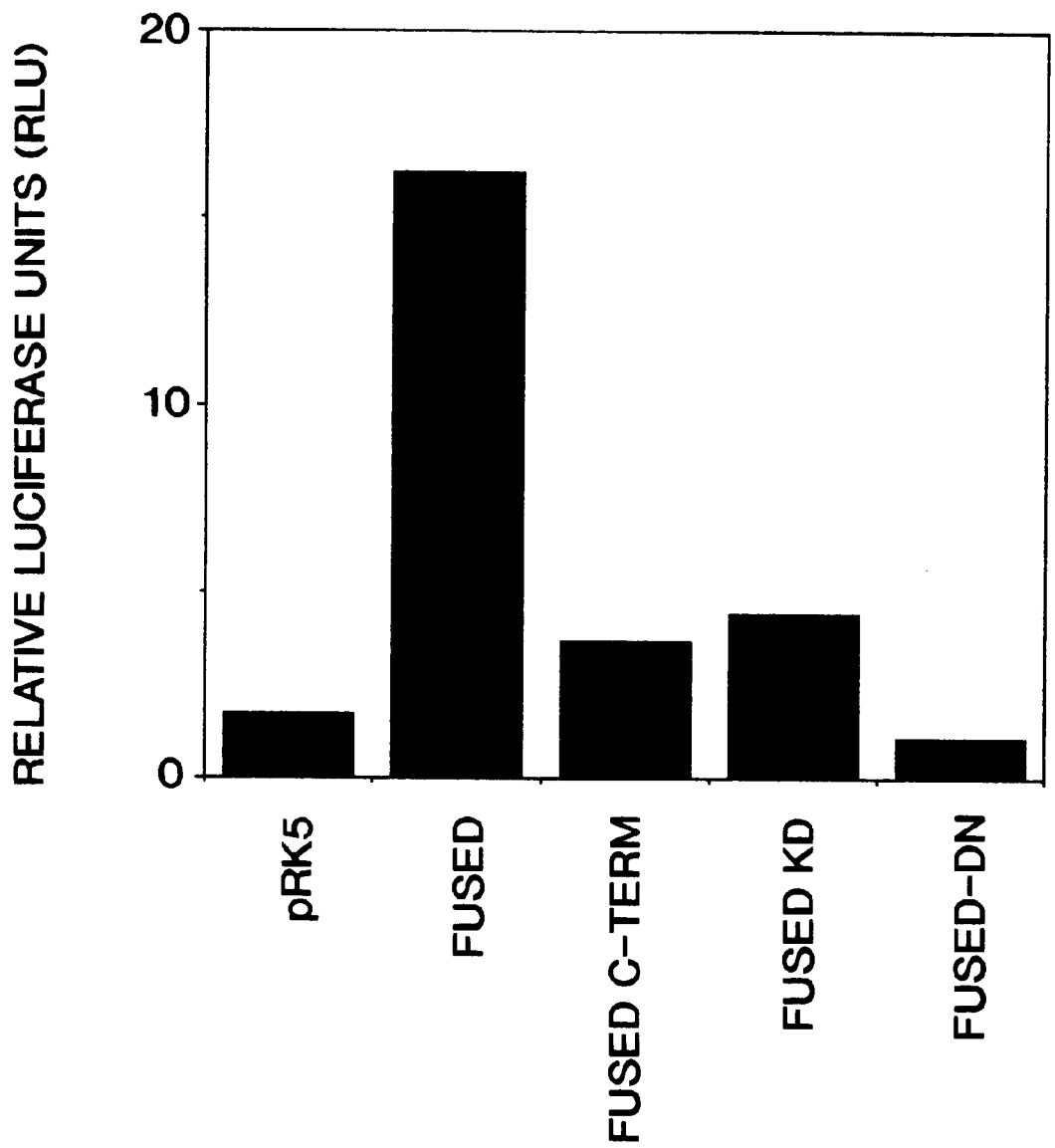

Detailed analysis of fused expression in adult testis was also performed by in situ hybridization (FIG. 9). Fused was found to be expressed at very high levels on stages I and II germ cells in the seminiferous tubules. Levels of fused vary in different seminiferous tubules, suggesting that its expression is regulated according to the germinal cell state of differentiation.

EXAMPLE 7

Gli Luciferase Assay

Given the low homology between dfused and hfused, it was prudent to determine whether in fact the isolated hfused is indeed a mediator of Hh signaling. The following assay was developed to measure the activation of the transcription factor GLI, the mammalian homologue of the Drosophila cubitus interruptus (Ci). It has been shown that GLI is a transcription factor activated upon SHh stimulation of cells.

Nine (9) copies of a GLI binding site present in the HNF3β enhancer, (Sasaki et al., *Development* 124: 1313–1322 (1997)), were introduced in front of a thymidine kinase minimal promoter driving the luciferase reporter gene in the pGL3 plasmid (Promega). The sequence of the GLI binding sequence was: TCGACAAGCAGG GAACACCCAAGTAGAAGCTC (p9XGliLuc) (SEQ ID NO:19), while the negative control sequence was: TCGA-CAAGCAGGGAAGTGGGAAGTAGAAGCTC (p9XmGliLuc) (SEQ ID NO:20). These constructs were cotransfected with the full length fused construct or with a plasmid encoding sonic hedgehog in C3H10T½ cells grown in F12, DMEM (50:50), 10% FCS heat inactivated. The day before transfection 1×10⁵ cells per well was inoculated in 6 well plates, in 2 ml of media. The following day, 1 μg of each construct was cotransfected in duplicate with 0.025 mg ptkRenilla luciferase plasmid using lipofectamine (Gibco-BRL) in 100 μl OptiMem (with GlutaMAX) as per manufacturer's instructions for 3 hours at 37° C. Serum (20%, 1 ml) was then added to each well and the cells were incubated for 3 more hours at 37° C. Cells were then washed twice with PBS, then incubated for 48 hours at 37° C. in 2 ml of media. Each well was then washed with PBS, and the cells lysed in 0.5 ml Passive Lysis Buffer (Promega) for 15 min. at room temperature on a shaker. The lysate was transferred in eppendorf tubes on ice, spun in a refrigerated centrifuge for 30 seconds and the supernatant saved on ice. For each measure, 20 μl of cell lysate was added to 100 μl of LARII (luciferase assay reagent, Promega) in a polypropylene tube and the luciferase light activity measured. The reaction was stopped by the addition of Stop and Glow buffer (Promega), mixed by pipetting up and down 3 to 5 times and Renilla luciferase lights activity was measured on the luminometer.

As shown in FIG. 6, fused can induce GLI activity (9.5 fold) in a similar manner as SHh (5.5 fold) This result suggests that the fused gene isolated is a mediator of SHh signaling. An irrelevant serine-threonine kinase, Akt, was not active in this assay (data not shown). The fused activity is dependent on an intact kinase domain as molecules with deletion of this region (fused C-term (SEQ ID NO:27)) or mutation of a conserved lysine residue at about amino acid position 33 in the ATP binding site (fused-DN (SEQ ID NO:25)) were not able to activate GLI. Similarly, the C-terminal tail of the protein is necessary for this activity since the kinase domain alone was not active in this assay (fused KD (SEQ ID NO:24)). Expression of each protein was verified by Western blot using an HA tag inserted at the N-terminus of the molecule (data not shown). These results substantiate the conclusion that the homologue of the dfused isolated by Applicants is indeed hfused. Furthermore, these results indicate that fused is capable of and sufficient for the activation of Gli, the major target of SHh signaling and is thus likely to be a direct mediator of the SHh signal in vertebrates.

EXAMPLE 8

Induced cyclopia in frog embryos

Introduction:

In order to demonstrate that the human fused gene is not only capable of but also required to transduce the SHh signal in vertebrates, a mutant version of fused known as fused-DN (dominant negative) having a mutation of the lysine at position 33 in the ATP binding site was created (SEQ ID NO:25). This residue is conserved among all kinases and is necessary for kinase activity (Hanks et al., *Methods Enzymol.* 200: 38–62 (1991) and its conversion to any other residue in most cases results in the creation of dominant negative mutants.

Methods:

Plasmid Construction:

Wild type fused cDNA with an HA tag inserted at the carboxy terminus was subcloned into pRK5 and a dominant negative form was generated by conversion of lysine at positive 33 to an arginine. Supercoiled plasmid DNA was prepared by Qiagen and used for injection into *Xenopus laevis* embryo.

Manipulation of Xenopus embryos:

Adult female frogs were boosted with 200 I.U. pregnant mare serum 3 days before use and with 800 I.U. of human chorionic gonadotropin the night before injection. Fresh oocytes were squeezed out from female frogs the next morning and in vitro fertilization of oocytes was performed by mixing oocytes with minced testis from sacrificed male frogs. Developing embryos were maintained and staged according to Nieuwkoop and Faber, Normal Table of *Xenopus laevis,* N.-H. P. Co., ed. (Amsterdam, 1967).

Fertilized eggs were dejellied with 2% cysteine (pH 7.8) for 10 minutes, washed once with distilled water and transferred to 0.1× MBS with 5% Ficoll. Fertilized eggs were lined on injection trays in 0.1× MBS with 5% Ficoll. Two-cell stage developing Xenopus embryos were injected with 200 pg of either pRK5 containing wild type fused (WT) (SEQ ID NO:1) or dominant negative fused (DN) (SEQ ID NO:25). Injected embryos were kept on trays for another 6 hours, after which they were transferred to 0.1× MBS with 50 mg/ml gentamycin for 3 days until reaching Nieukwkoop stage 35 when eye development is complete.

Figure 11A:
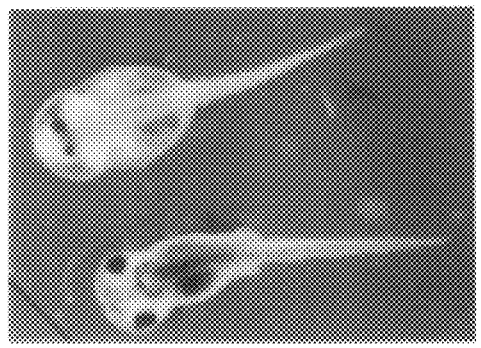
FIGS. 11A–11E are photographs showing that fused-DN (SEQ ID NO:25) inhibits SHh signaling in early Xenopus development. Depicted are.

Results:

To test whether human fused gene acts as a signal transducer of Hedgehog signaling, we injected wild type (SEQ ID NO:2) or dominant negative form (SEQ ID NO:25) of human fused in developing frog embryos. Embryos injected with 120 pg of DNA divided normally in blastula stage and gastrulate normally. While eye development was normal in wild type, fused (SEQ ID NO:2) injected and mock injected embryos, about 30% (Table 1) of the embryos that were injected with fused-DN showed fused eye structure or two eyes connected by some pigmented retina tissue (FIG. 11A). In Table 1, 200 pg of plasmid DNA was delivered to the animal pole of 2-cell stage embryos. Each sample represents the results of at least 3 independent experiments. Embryos were scored visually for cyclopia defects.

TABLE 1

Fusion-DN Induced Cyclopia in Xenopus Embryos

| Injected DNA | Normal | Cyclop | n |
|---|---|---|---|
| Hu-fused (SEQ ID NO:2) | 45 | 0 | 45 |
| Kinase domain (SEQ ID NO:24) | 43 | 0 | 43 |
| C-terminus (SEQ ID NO:27) | 53 | 1 | 54 |
| fused DN (SEQ ID NO:25) | 32 | 15 | 47 |
| Uninjected | 61 | 0 | 61 |

Figure 11B:
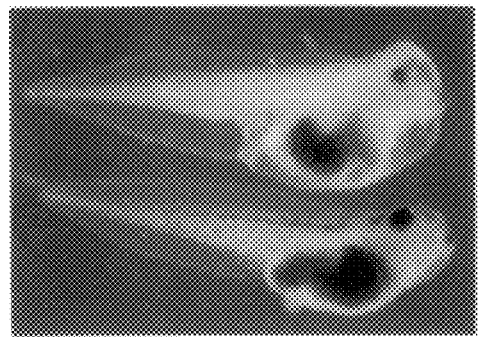

The observed cyclopia phenotype is strikingly similar to the one of mouse embryos deficient in SHh (Chiang et al., *Nature* 383: 407–13 (1996) and of zebrafish embryos where SHh signaling has been blocked by overexpression of a constitutive active PKA, Hammerschmidt et al., *Genes Dev.* 10: 647–58 (1996); Ungar and Moon, *Dev. Biol.* 178: 186–91 (1996). In addition, both brain (forebrain) and gut development appeared normal at later stages of tadpole development in the fused-DN (SEQ ID NO:25) injected embryos (FIG. 11B). In contrast, embryos overexpressing either wild type fused (SEQ ID NO:2) or N or C-terminal terminal truncation mutants (SEQ ID NOS:27 and 24), respectively, did not present any abnormalities.

During normal development of the Xenopus eye, the eye primordium starts as a single field expressing transcription factor Pax-6, which is a vertebrate homologue of Drosophila eyeless, Li et al., *Development.* 124: 603–15 (1997). At the neurula stage, this eye field is separated into two eye primordia due to an inhibiting signal from prechordal mesoderm. It has been further demonstrated that SHh is the prechordal mesoderm derived signal that is responsible for the inhibition of Pax-6 expression in the midline of the eyefield.

Figure 11C:
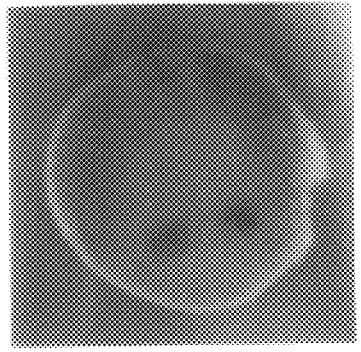
Figure 11D:
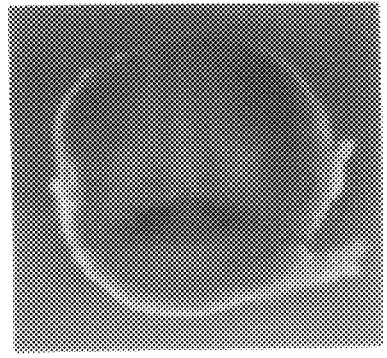
Figure 11E:
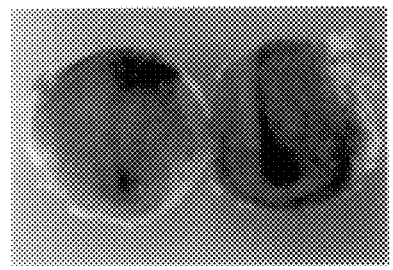

To further understand how overexpression of fused-DN (SEQ ID NO:25) induced a fused eye in Xenopus embryos, whole mount in situ hybridization was performed in order to determine the expression pattern of Pax-6 in injected embryos. As shown in FIG. 11C, Pax-6 expression in embryos injected with fused-DN (SEQ ID NO:25) remains as a single field (FIG. 11D). Thus fused-DN (SEQ ID NO:25) induces a cyclopia phenotype by most likely preventing SHh from inhibiting Pax-6 expression in the midline of the eyefield.

EXAMPLE 9

Rescue of fused-DN Injected Xenopus Embryos by Gli

SHh expression in early floor plate cells is induced by SHh produced by the notochord. To test whether SHh expression in the floor plate will also be inhibited when SHh signaling is blocked, early neurula stage embryos injected with fused-DN or wild-type constructs were stained for SHh expression (See Example 8 for procedure). SHh expression in floor plate cells or early neurula stage embryos was completely suppressed in 26 out of 28 embryos injected when the mutated fused is overexpressed (Table 2, FIG. 11C, left embryo), while the expression of SHh was unaffected in control embryos (FIG. 6E, right embryo). Table 2 represents scored data from three independent experiments. 100 pg of fused-DN, 100 pg of fused-wt or 50 pg of Gli-1 plasmid were injected in 2-cell stage embryos. Embryos were harvested at early neurula stage for SHh staining.

TABLE 2

Wild type fused and Gli rescue SHh expression in floor plate when coexpressed with fused-DN

|  | SHh staining | Percentage |
| --- | --- | --- |
| fused-DN (SEQ ID NO:25) | 2/28 | 7% |
| fused-DN + fused WT | 20/24 | 83% |
| fused-DN + Gli | 36/36 | 100 |

To confirm that this phenotype was due to specific inhibition of the SHh signaling pathway in the floor plate, we attempted to rescue the phenotype by coinjection of wt fused RNA with fused-DN RNA in a 1:1 ratio. Table 2 shows that more than 80% of the embryos coinjected with wt fused and fused-DN RNAs show normal SHh staining in the floor plate. This demonstrates that SHh expression in fused-DN injected embryos is specifically blocked by inhibition of endogenous fused activity.

To further demonstrate that the observed phenotype of fused-DN are due to disruption of the SHh signal cascade and to confirm that hfused works upstream of Gli in this pathway, we asked whether the overexpression of Gli can also rescue the phenotype of Xenopus embryos injected with fused-DN. As shown in Table 2, the rescue of SHh expression in the floor plate of fused-DN injected embryos is complete when Gli is overexpressed. Taken together, these findings are consistent with Applicants hypothesis that vertebrate fused functions in the SHh pathway and that is a necessary mediator in the SHh signal transduction pathway, which acts upstream of Gli.

EXAMPLE 10

Immunoprecipitations and In Vitro Kinase Assay

Figure 12:
FIG. 12 is a photograph which confirms the kinase activity of fused (SEQ ID NO:2) and its activation of Gli. Depicted are 293 cells transfected with HA tagged fiised constructs as indicated in Example 10 and immunoprecipitated with anti-HA antibodies and protein A sepharose. Protein A beads were subjected to in vitro kinase assay as described in Example 10 in the presence of MBP.

To directly determine whether hfused has kinase activity, fused, fused-DN and fused-kd cDNAs were tagged with the influenza HA epitope tag and transiently transfected into 293 cells. Immunoprecipitates were tested for kinase activity in the presence of myelin basic protein (MBP) and [γ-$^{32}$P]-ATP. The amount of 32P incorporated into MBP was determined after SDS-PAGE and found to be was about 3 times higher than in fused-KD (SEQ ID NO:25) and 2 times higher in wt fused (SEQ ID NO:2) containing extracts compared to controls, while mutation of Lys33 to Arg (fused-DN) (SEQ ID NO:25) neutralizes the activity (FIG. 12).

For immunoprecipitation experiments human embryonic kidney 293 cells were transiently transfected with the various expression plasmids. After 24 hours, the transfected cells were collected and lysed for 20 min. at 4° C. in 1 ml of lysis buffer (50 mM Tris, pH 8.0), 150 mM NaCl, 1 mM EDTA, 1 mM sodium fluoride, 1 mM sodium orthovanadate, 1 mM PMSF and protease inhibitors (Complete, Boehringer Mannheim) containing 1% NP-40, 0.5% deoxycholic acid. Cell debris was removed by centrifugation for 10 min. at 10,000 rpm and the sodium chloride concentration of the cell lysates was increased to 250 mM. The supernatant was precleared for 1 hour with 20 μl Protein A Sepharose (Pharmacia). Lysates were immunoprecipitated using anti-HA antibodies followed by Protein A Sepharose. The beads were washed twice with lysis buffer containing 250 mM sodium chloride, twice with lysis buffer containing 1M sodium chloride, and then twice with kinase assay buffer (20 mM HEPES, pH 7.6), 1 mM DTT, 1 mM NaF and 1 mM sodium orthovanadate). After the last wash, the beads were resuspended in 20 μl kinase assay buffer supplemented with 10 mCi [γ-$^{32}$P]-ATP, 20 mM β-glycerophosphate, 20 mM PNPP, 20 mM MgCl$_2$, 1 mM EGTA, 100 μM cold ATP and 0.5 mg/ml Myelin Basic Protein (Sigma), and incubated for 20 min. at 37° C. Reactions were stopped with 20 μl SDS-sample buffer, run on a denaturing 4–20% SDS polyacrylamide gel, and analyzed by phosphoimager.

EXAMPLE 11

Expression of fused in E. coli

The DNA sequence encoding human fused is initially amplified using selected PCR primers. The primers should contain restriction enzyme sites that correspond to the restriction enzyme sites on the selected expression vector. A variety of expression vectors may be employed. An example of a suitable vector is pBR322 (derived from E. coli; see Bolivar et al., Gene, 2:95 (1977)) which contains genes for ampicillin and tetracycline resistance. The vector is digested with restriction enzyme and dephosphorylated. The PCR amplified sequences are then ligated into the vector. The vector will preferably include sequences that encode for an antibiotic resistance gene, a trp promoter, a polyhis leader (including the first six STII codons, polyhis sequence, and enterokinase cleavage site), the vertebrate fused coding region, lambda transcriptional terminator, and an argU gene.

The ligation mixture is then used to transform a selected E. coli strain using the methods described in Sambrook et al., supra. Transformants are identified by their ability to grow on LB plates and antibiotic resistant colonies are then selected. Plasmid DNA can be isolated and confirmed by restriction analysis and DNA sequencing.

Selected clones can be grown overnight in liquid culture medium such as LB broth supplemented with antibiotics. The overnight culture may subsequently be used to inoculate a larger scale culture. The cells are then grown to a desired optical density, during which the expression promoter is turned on.

After culturing the cells for several more hours, the cells can be harvested by centrifugation. The cell pellet obtained by the centrifugation can be solubilized using various agents known in the art, and the solubilized vertebrate fused protein can then be purified using a metal chelating column under conditions that allow tight binding of the protein.

EXAMPLE 12

Expression of fused in mammalian cells

The vector, pRK5 (see EP 307,247, published Mar. 15, 1989), is employed as the expression vector. Optionally, the vertebrate fused DNA is ligated into pRK5 with selected restriction enzymes to allow insertion of the vertebrate fused DNA using ligation methods such as described in Sambrook et al., supra. The resulting vector is called pRK5-fused.

In one embodiment, the selected host cells may be 293 cells. Human 293 cells (ATCC CCL 1573) are grown to confluence in tissue culture plates in medium such as DMEM supplemented with fetal calf serum and optionally, nutrient components and/or antibiotics. About 10 μg pRK5-fused DNA is mixed with about 1 μg DNA encoding the VA RNA gene [Thimmappaya et al., *Cell,* 31:543 (1982)] and dissolved in 500 μl of 1 mM Tris-HCl, 0.1 mM EDTA, 0.227M CaCl$_2$. To this mixture is added, dropwise, 500 μl of 50 mM HEPES (pH 7.35), 280 mM NaCl, 1.5 mM NaPO$_4$, and a precipitate is allowed to form for 10 minutes at 25° C. The precipitate is suspended and added to the 293 cells and allowed to settle for about four hours at 37° C. The culture medium is aspirated off and 2 ml of 20% glycerol in PBS is added for 30 seconds. The 293 cells are then washed with serum free medium, fresh medium is added and the cells are incubated for about 5 days.

Approximately 24 hours after the transfections, the culture medium is removed and replaced with culture medium (alone) or culture medium containing 200 μCi/ml $^{35}$S-cysteine and 200 μCi/ml $^{35}$S-methionine. After a 12 hour incubation, the conditioned medium is collected, concentrated on a spin filter, and loaded onto a 15% SDS gel. The processed gel may be dried and exposed to film for a selected period of time to reveal the presence of vertebrate fused polypeptide. The cultures containing transfected cells may undergo further incubation (in serum free medium) and the medium is tested in selected bioassays.

In an alternative technique, vertebrate fused may be introduced into 293 cells transiently using the dextran sulfate method described by Somparyrac et al., *Proc. Natl. Acad. Sci.,* 12:7575 (1981). 293 cells are grown to maximal density in a spinner flask and 700 μg pRK5-fused DNA is added. The cells are first concentrated from the spinner flask by centrifugation and washed with PBS. The DNA-dextran precipitate is incubated on the cell pellet for four hours. The cells are treated with 20% glycerol for 90 seconds, washed with tissue culture medium, and re-introduced into the spinner flask containing tissue culture medium, 5 μg/ml bovine insulin and 0.1 μg/ml bovine transferrin. After about four days, the conditioned media is centrifuged and filtered to remove cells and debris. The sample containing expressed vertebrate fused can then be concentrated and purified by any selected method, such as dialysis and/or column chromatography.

In another embodiment, vertebrate fused can be expressed in CHO cells. The pSUi-fused can be transfected into CHO cells using known reagents such as CaPO$_4$ or DEAE-dextran. As described above, the cell cultures can be incubated, and the medium replaced with culture medium (alone) or medium containing a radiolabel such as $^{35}$S-methionine. After determining the presence of vertebrate fused polypeptide, the culture medium may be replaced with serum free medium. Preferably, the cultures are incubated for about 6 days, and then the conditioned medium is harvested. The medium containing the expressed vertebrate fused can then be concentrated and purified by any selected method.

Epitope-tagged vertebrate fused may also be expressed in host CHO cells. The vertebrate fused may be subcloned out of the pRK5 vector. The subclone insert can undergo PCR to fuse in frame with a selected epitope tag such as a poly-his tag into an expression vector. The poly-his tagged vertebrate fused insert can then be subcloned into a SV40 driven vector containing a selection marker such as DHFR for selection of stable clones. Finally, the CHO cells can be transfected (as described above) with the SV40 driven vector. Labeling may be performed, as described above, to verify expression. The culture medium containing the expressed poly-His tagged vertebrate fused can then be concentrated and purified by any selected method, such as by Ni$^{2+}$-chelate affinity chromatography.

EXAMPLE 13

Expression of vertebrate fused in Yeast

The following method describes recombinant expression of vertebrate fused in yeast.

First, yeast expression vectors are constructed for intracellular production or secretion of vertebrate fused from the ADH2/GAPDH promoter. DNA encoding vertebrate fused, a selected signal peptide and the promoter is inserted into suitable restriction enzyme sites in the selected plasmid to direct intracellular expression of vertebrate fused. For secretion, DNA encoding vertebrate fused can be cloned into the selected plasmid, together with DNA encoding the ADH2/GAPDH promoter, the yeast alpha-factor secretory signal/leader sequence, and linker sequences (if needed) for expression of vertebrate fused.

Yeast cells, such as yeast strain AB110, can then be transformed with the expression plasmids described above and cultured in selected fermentation media. The transformed yeast supernatants can be analyzed by precipitation with 10% trichloroacetic acid and separation by SDS-PAGE, followed by staining of the gels with Coomassie Blue stain.

Recombinant vertebrate fused can subsequently be isolated and purified by removing the yeast cells from the fermentation medium by centrifugation and then concentrating the medium using selected cartridge filters. The concentrate containing vertebrate fused may further be purified using selected column chromatography resins.

EXAMPLE 14

Expression of vertebrate fused in Baculovirus-Infected Insect Cells

The following method describes recombinant expression of vertebrate fused in Baculovirus-infected insect cells.

The vertebrate fused is fused upstream of an epitope tag contained within a baculovirus expression vector. Such epitope tags include poly-his tags and immunoglobulin tags (like Fc regions of IgG). A variety of plasmids may be employed, including plasmids derived from commercially available plasmids such as pVL1393 (Novagen). Briefly, the vertebrate fused or the desired portion of the vertebrate fused (such as the sequence encoding the extracellular domain of a transmembrane protein) is amplified by PCR with primers complementary to the 5' and 3' regions. The 5' primer may incorporate flanking (selected) restriction enzyme sites. The product is then digested with those selected restriction enzymes and subcloned into the expression vector.

Recombinant baculovirus is generated by co-transfecting the above plasmid and BaculoGold™ virus DNA (Pharmingen) into *Spodoptera frugiperda* ("Sf9") cells (ATCC CRL 1711) using lipofectin (commercially available from GIBCO-BRL). After 4–5 days of incubation at 28° C., the released viruses are harvested and used for further amplifications. Viral infection and protein expression is performed as described by O'Reilley et al., Baculovirus expression vectors: A laboratory Manual, Oxford: Oxford University Press (1994).

Expressed poly-his tagged vertebrate fused can then be purified, for example, by Ni$^{2+}$-chelate affinity chromatography as follows. Extracts are prepared from recombinant virus-infected Sf9 cells as described by Rupert et al., *Nature,* 362:175–179 (1993). Briefly, Sf9 cells are washed, resuspended in sonication buffer (25 mL Hepes, pH 7.9; 12.5 mM MgCl$_2$; 0.1 mM EDTA; 10% Glycerol; 0.1% NP-40; 0.4M KCl), and sonicated twice for 20 seconds on ice. The sonicates are cleared by centrifugation, and the supernatant is diluted 50-fold in loading buffer (50 mM phosphate, 300 mM NaCl, 10% Glycerol, pH 7.8) and filtered through a 0.45 μm filter. A Ni$^{2+}$-NTA agarose column (commercially available from Qiagen) is prepared with a bed volume of 5 mL, washed with 25 mL of water and equilibrated with 25 mL of loading buffer. The filtered cell extract is loaded onto the column at 0.5 mL per minute. The column is washed to baseline A$_{280}$ with loading buffer, at which point fraction collection is started. Next, the column is washed with a secondary wash buffer (50 mM phosphate; 300 mM NaCl, 10% Glycerol, pH 6.0), which elutes nonspecifically bound protein. After reaching A$_{280}$ baseline again, the column is developed with a 0 to 500 mM Imidazole gradient in the secondary wash buffer. One mL fractions are collected and analyzed by SDS-PAGE and silver staining or western blot with Ni$^{2+}$-NTA-conjugated to alkaline phosphatase (Qiagen). Fractions containing the eluted His$_{10}$-tagged vertebrate fused are pooled and dialyzed against loading buffer. Alternatively, purification of the IgG tagged (or Fc tagged) vertebrate fused can be performed using known chromatography techniques, including for instance, Protein A or protein G column chromatography.

EXAMPLE 15

Preparation of Antibodies that Bind Vertebrate fused

This example illustrates preparation of monoclonal antibodies, which can specifically bind vertebrate fused.

Techniques for producing the monoclonal antibodies are known in the art and are described, for instance, in Goding, supra. Immunogens that may be employed include purified vertebrate fused, fusion proteins containing vertebrate fused, and cells expressing recombinant vertebrate fused on the cell surface. Selection of the immunogen can be made by the skilled artisan without undue experimentation.

Mice, such as Balb/c, are immunized with the vertebrate fused immunogen emulsified in complete Freund's adjuvant and injected subcutaneously or intraperitoneally in an amount from 1–100 micrograms. Alternatively, the immunogen is emulsified in MPL-TDM adjuvant (Ribi Immunochemical Research, Hamilton, Mont.) and injected into the animal's hind foot pads. The immunized mice are then boosted 10 to 12 days later with additional immunogen emulsified in the selected adjuvant. Thereafter, for several weeks, the mice may also be boosted with additional immunization injections. Serum samples may be periodically obtained from the mice by retro-orbital bleeding for testing in ELISA assays to detect vertebrate fused antibodies.

After a suitable antibody titer has been detected, the animals "positive" for antibodies can be injected with a final intravenous injection of vertebrate fused. Three to four days later, the mice are sacrificed and the spleen cells are harvested. The spleen cells are then fused (using 35% polyethylene glycol) to a selected murine myeloma cell line such as P3X63AgU.1, available from ATCC, No. CRL 1597. The fusions generate hybridoma cells which can then be plated in 96 well tissue culture plates containing HAT (hypoxanthine, aminopterin, and thymidine) medium to inhibit proliferation of non-fused cells, myeloma hybrids, and spleen cell hybrids.

The hybridoma cells will be screened in an ELISA for reactivity against vertebrate fused. Determination of "positive" hybridoma cells secreting the desired monoclonal antibodies against vertebrate fused is within the skill in the art.

The positive hybridoma cells can be injected intraperitoneally into syngeneic Balb/c mice to produce ascites containing the anti- vertebrate fused monoclonal antibodies. Alternatively, the hybridoma cells can be grown in tissue culture flasks or roller bottles. Purification of the monoclonal antibodies produced in the ascites can be accomplished using ammonium sulfate precipitation, followed by gel exclusion chromatography. Alternatively, affinity chromatography based upon binding of antibody to protein A or protein G can be employed.

Deposit of Material

The following materials have been deposited with the American Type Culture Collection, 10801 University Boulevard, Manassas, Va., USA (ATCC):

| Designation | ATCC Dep. No. | Deposit Date |
| --- | --- | --- |
| pRK5tkneo.hFused-1272 | 209637 | 2/19/98 |

This deposit was made under the provisions of the Budapest Treaty on the International Recognition of the Deposit of Microorganisms for the Purpose of Patent Procedure and the Regulations thereunder (Budapest Treaty). This assures maintenance of a viable culture of the deposit for 30 years from the date of deposit. The deposit will be made available by ATCC under the terms of the Budapest Treaty, and subject to an agreement between Genentech, Inc. and ATCC, which assures permanent and unrestricted availability of the progeny of the culture of the deposit to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 USC ☐ 122 and the Commissioner's rules pursuant thereto (including 37 CFR ☐ 1.14 with particular reference to 886 OG 638).

The assignee of the present application has agreed that if a culture of the materials on deposit should die or be lost or destroyed when cultivated under suitable conditions, the materials will be promptly replaced on notification with another of the same. Availability of the deposited material is not to be construed as a license to practice the invention in contravention of the rights granted under the authority of any government in accordance with its patent laws.

The foregoing written specification is considered to be sufficient to enable one skilled in the art to practice the invention. The present invention is not to be limited in scope by the construct deposited, since the deposited embodiment is intended as a single illustration of certain aspects of the invention and any constructs that are functionally equivalent are within the scope of this invention. The deposit of material herein does not constitute an admission that the written description herein contained is inadequate to enable the practice of any aspect of the invention, including the best mode thereof, nor is it to be construed as limiting the scope of the claims to the specific illustrations that it represents. Indeed, various modifications of the invention in addition to those shown and described herein will become apparent to those skilled in the art from the foregoing description and fall within the scope of the appended claims.

What is claimed is:

1. Isolated nucleic acid comprising DNA selected from the group consisting of:
   (a) a nucleotide sequence encoding the sequence of amino acids 1 to about 260 of FIG. 1 (SEQ ID NO:24);
   (b) a nucleotide sequence comprising at least 780 residues which hybridizes under stringent conditions to the complement of the nucleotide sequence encoding SEQ ID NO:24;
   (c) a nucleotide sequence which encodes SEQ ID NO:24 with at least one conservatively substituted amino acid residue; and
   (d) a nucleotide sequence which encodes SEQ ID NO:24 with an addition or deletion of one to five amino acid residues.

2. The isolated nucleic acid of claim 1 comprising DNA encoding the sequence of amino acids 1 to 1315 (SEQ ID NO:2) of FIG. 1.

3. The isolated nucleic acid of claim 1 comprising DNA encoding a polypeptide having a lysine at amino acid position 33 of SEQ ID NO:24.

4. The isolated nucleic acid of claim 1 comprising a nucleotide sequence encoding the sequence of amino acids 1 to about 260 of FIG. 1 (SEQ ID NO:24).

5. The isolated nucleic acid of claim 1 comprising a nucleotide sequence comprising at least 780 residues which hybridizes under stringent conditions to the complement of the nucleotide sequence encoding SEQ ID NO:24.

6. The isolated nucleic acid of claim 1 comprising a nucleotide sequence which encodes SEQ ID NO:24 with at least one conservatively substituted amino acid residue.

7. The isolated nucleic acid of claim 1 comprising a nucleotide sequence which encodes SEQ ID NO:24 with an addition or deletion of one to five amino acid residues.

8. A vector comprising the nucleic acid of claim 1.

9. The vector of claim 8 operably linked to control sequences recognized by a host cell transformed with the vector.

10. A host cell transformed with the vector of claim 9.

11. The host cell of claim 10 which is mammalian.

12. The host cell of claim 10 which is prokaryotic.

13. The host cell of claim 10 wherein said cell is a yeast cell.

14. A process for producing a polypeptide comprising culturing the host cell of claim 10 under conditions suitable for expression of a polypeptide encoded by the nucleic acid of claim 1 and recovering the polypeptide from the cell culture.

15. The host cell of claim 11 wherein said cell is a CHO cell.

16. The host cell of claim 12 wherein said cell is an E. coli.

17. The host cell of claim 13 which is Saccharomyces cerevisiae.

18. An isolated nucleic acid comprising DNA of at least 780 residues which (a) hybridizes under stringent conditions to the complement of the nucleotide sequence encoding the cDNA in ATCC Deposit No. 209637, or (b) the complement of the DNA of (a).

19. An isolated nucleic acid comprising DNA encoding (a) the same mature polypeptide encoded by the cDNA in ATCC Deposit No. 209637 with at least one conservative substitution, or (b) the complement of the DNA or (a).

20. An isolated nucleic acid comprising DNA encoding (a) the same mature polypeptide encoded by the cDNA in ATCC Deposit No. 209637 with an addition or deletion of one to five amino acid residues, or (b) the complement of the DNA of (a).

21. An isolated nucleic acid comprising DNA selected from the group consisting of:
   (a) a nucleotide sequence which encodes a human fused polypeptide comprising the sequence of amino acids 1 to 1315 of FIG. 1 (SEQ ID NO:2);
   (b) a nucleotide sequence comprising at least 780 residues which hybridizes under stringent conditions to the complement of the nucleotide sequence encoding SEQ ID NO:2;
   (c) a nucleotide sequence which encodes SEQ ID NO:2 with at least one conservatively substituted amino acid residue; and
   (d) a nucleotide sequence which encodes SEQ ID NO:2 with an addition or deletion of one to five amino acid residues.

22. The isolated nucleic acid of claim 21 comprising a nucleotide sequence which encodes a human fused polypeptide comprising the sequence of amino acids 1 to 1315 of FIG. 1 (SEQ ID NO:2).

23. The isolated nucleic acid of claim 21 comprising a nucleotide sequence of at least 780 residues which hybridizes under stringent conditions to the complement of the nucleotide sequence encoding SEQ ID NO:2.

24. The isolated nucleic acid of claim 21 comprising a nucleotide sequence which encodes SEQ ID NO:2 with at least one conservatively substituted amino acid residue.

25. The isolated nucleic acid of claim 21 comprising a nucleotide sequence which encodes SEQ ID NO:2 with an addition or deletion of one to five amino acid residues.

\* \* \* \* \*

SEQUENCE LISTING

<160> NUMBER OF SEQ ID NOS: 27

<210> SEQ ID NO 1
<211> LENGTH: 4880
<212> TYPE: DNA
<213> ORGANISM: Homo sapiens
<220> FEATURE:
<221> NAME/KEY: unknown N
<222> LOCATION: 4160, 4243, 4361
<223> OTHER INFORMATION: unknown

<400> SEQUENCE: 1

```
       cccggggatc ctctagagat ccctcgacct cgacccacgc gtccgcccac  50
       gcgtccgccc acgcgtccgg ggcgtcccag atgttgtgga actgtccctg  100
       gatctatagc tcttcaccgt ctctactttc ttccttctaa gagatcctga  150
       aacctctgtc atg gaa aag tac cac gtg ttg gag atg att       190
                   Met Glu Lys Tyr His Val Leu Glu Met Ile
                    1               5                   10
gga gaa ggc tct ttt ggg agg gtg tac aag ggt cga aga                229
Gly Glu Gly Ser Phe Gly Arg Val Tyr Lys Gly Arg Arg
                15                  20
aaa tac agt gct cag gtc gtg gcc ctg aag ttc atc cca                268
Lys Tyr Ser Ala Gln Val Val Ala Leu Lys Phe Ile Pro
            25                  30                  35
aaa ttg ggg cgc tca gag aag gag ctg agg aat ttg caa                307
Lys Leu Gly Arg Ser Glu Lys Glu Leu Arg Asn Leu Gln
                    40                  45
cga gag att gaa ata atg cgg ggt ctg cgg cat ccc aac                346
Arg Glu Ile Glu Ile Met Arg Gly Leu Arg His Pro Asn
50                  55                  60
att gtg cat atg ctt gac agc ttt gaa act gat aaa gag                385
Ile Val His Met Leu Asp Ser Phe Glu Thr Asp Lys Glu
                65                  70                  75
gtg gtg gtg gtg aca gac tat gct gag gga gag ctc ttt                424
Val Val Val Val Thr Asp Tyr Ala Glu Gly Glu Leu Phe
                    80                  85
cag atc cta gaa gat gac gga aaa ctt cct gaa gac cag                463
Gln Ile Leu Glu Asp Asp Gly Lys Leu Pro Glu Asp Gln
        90                  95                  100
gtt cag gcc att gct gcc cag ttg gtg tca gcc ctg tac                502
Val Gln Ala Ile Ala Ala Gln Leu Val Ser Ala Leu Tyr
                105                 110
tat ctg cat tcc cac cgc atc cta cac cga gat atg aag                541
Tyr Leu His Ser His Arg Ile Leu His Arg Asp Met Lys
115                 120                 125
cct cag aac atc ctc ctc gcc aag ggt ggt ggc atc aag                580
Pro Gln Asn Ile Leu Leu Ala Lys Gly Gly Gly Ile Lys
                130                 135                 140
ctc tgt gac ttt gga ttt gcc cgg gct atg agc acc aat                619
Leu Cys Asp Phe Gly Phe Ala Arg Ala Met Ser Thr Asn
                    145                 150
aca atg gtg ctg aca tcc atc aaa ggc aca cca ctc tat                658
Thr Met Val Leu Thr Ser Ile Lys Gly Thr Pro Leu Tyr
        155                 160                 165
atg tct cca gag ctg gtg gag gag cga cca tac gac cac                697
Met Ser Pro Glu Leu Val Glu Glu Arg Pro Tyr Asp His
                170                 175
aca gcg gac ctc tgg tct gtt ggc tgc ata cta tat gaa                736
Thr Ala Asp Leu Trp Ser Val Gly Cys Ile Leu Tyr Glu
180                 185                 190
ctg gca gta ggc acc cct ccc ttc tat gct aca agc atc                775
Leu Ala Val Gly Thr Pro Pro Phe Tyr Ala Thr Ser Ile
                195                 200                 205
ttt cag ctg gtc agc ctc att ctc aag gac cct gtg cgc                814
Phe Gln Leu Val Ser Leu Ile Leu Lys Asp Pro Val Arg
                    210                 215
tgg ccc tca acc atc agt ccc tgc ttt aag aac ttc ctg                853
Trp Pro Ser Thr Ile Ser Pro Cys Phe Lys Asn Phe Leu
        220                 225                 230
cag gga ctg ctc acc aaa gac cca cgg cag cga ctg tcc                892
Gln Gly Leu Leu Thr Lys Asp Pro Arg Gln Arg Leu Ser
                235                 240
tgg cca gac ctc tta tat cac ccc ttt att gct ggt cat                931
Trp Pro Asp Leu Leu Tyr His Pro Phe Ile Ala Gly His
245                 250                 255
```

```
gtc acc ata ata act gag cca gca ggc cca gat ttg ggg  970
Val Thr Ile Ile Thr Glu Pro Ala Gly Pro Asp Leu Gly
        260                 265                 270
acc cca ttc acc agc cgc cta ccc cca gaa ctt cag gtc 1009
Thr Pro Phe Thr Ser Arg Leu Pro Pro Glu Leu Gln Val
                275                 280
cta aag gac gaa cag gcc cat cgg ttg gcc ccc aag ggt 1048
Leu Lys Asp Glu Gln Ala His Arg Leu Ala Pro Lys Gly
        285                 290                 295
aat cag tct cgc atc ttg act cag gcc tat aaa cgc atg 1087
Asn Gln Ser Arg Ile Leu Thr Gln Ala Tyr Lys Arg Met
                300                 305
gct gag gag gcc atg cag aag aaa cat cag aac aca gga 1126
Ala Glu Glu Ala Met Gln Lys Lys His Gln Asn Thr Gly
310                 315                 320
cct gcc ctt gag caa gag gac aag acc agc aag gtg gct 1165
Pro Ala Leu Glu Gln Glu Asp Lys Thr Ser Lys Val Ala
        325                 330                 335
cct ggc aca gcc cct ctg ccc aga ctc ggg gcc act cct 1204
Pro Gly Thr Ala Pro Leu Pro Arg Leu Gly Ala Thr Pro
                340                 345
cag gaa tca agc ctc ctg gcc ggg atc tta gcc tca gaa 1243
Gln Glu Ser Ser Leu Leu Ala Gly Ile Leu Ala Ser Glu
        350                 355                 360
ttg aag agc agc tgg gct aaa tca ggg act gga gag gtg 1282
Leu Lys Ser Ser Trp Ala Lys Ser Gly Thr Gly Glu Val
                365                 370
ccc tct gca cct cgg gaa aac cgg acc acc cca gat tgt 1321
Pro Ser Ala Pro Arg Glu Asn Arg Thr Thr Pro Asp Cys
375                 380                 385
gaa cga gca ttc cca gag gag agg cca gag gtg ctg ggc 1360
Glu Arg Ala Phe Pro Glu Glu Arg Pro Glu Val Leu Gly
        390                 395                 400
cag cgg agc act gat gta gtg gac ctg gaa aat gag gag 1399
Gln Arg Ser Thr Asp Val Val Asp Leu Glu Asn Glu Glu
                405                 410
cca gac agt gac aat gag tgg cag cac ctg cta gag acc 1438
Pro Asp Ser Asp Asn Glu Trp Gln His Leu Leu Glu Thr
        415                 420                 425
act gag cct gtg cct att caa ctg aag gct cct ctc acc 1477
Thr Glu Pro Val Pro Ile Gln Leu Lys Ala Pro Leu Thr
                430                 435
ttg ctg tgt aat cct gac ttc tgc cag cgc atc cag agt 1516
Leu Leu Cys Asn Pro Asp Phe Cys Gln Arg Ile Gln Ser
440                 445                 450
cag ctg cat gaa gct gga ggg cag atc ctg aaa ggc atc 1555
Gln Leu His Glu Ala Gly Gly Gln Ile Leu Lys Gly Ile
        455                 460                 465
ttg gag ggt gct tcc cac atc ctg cct gca ttc cgg gtc 1594
Leu Glu Gly Ala Ser His Ile Leu Pro Ala Phe Arg Val
                470                 475
ctg agc agt ctt ctc tcc agc tgc agt gat tct gtt gcc 1633
Leu Ser Ser Leu Leu Ser Ser Cys Ser Asp Ser Val Ala
        480                 485                 490
ttg tat tcc ttc tgc cgg gag gca ggg ctt cct ggg ctg 1672
Leu Tyr Ser Phe Cys Arg Glu Ala Gly Leu Pro Gly Leu
                495                 500
ctg ctg agt cta ctc agg cac agt cag gag agc aac agc 1711
Leu Leu Ser Leu Leu Arg His Ser Gln Glu Ser Asn Ser
505                 510                 515
ctc cag cag caa tct tgg tat ggg acc ttc tta cag gac 1750
Leu Gln Gln Gln Ser Trp Tyr Gly Thr Phe Leu Gln Asp
        520                 525                 530
ctg atg gct gtg att cag gcc tac ttt gcc tgt acc ttc 1789
Leu Met Ala Val Ile Gln Ala Tyr Phe Ala Cys Thr Phe
                535                 540
aat ctg gag agg agc cag aca agt gac agc ctg cag gtg 1828
Asn Leu Glu Arg Ser Gln Thr Ser Asp Ser Leu Gln Val
        545                 550                 555
ttt cag gag gct gcc aac ctt ttt ctg gac ctg ttg ggg 1867
Phe Gln Glu Ala Ala Asn Leu Phe Leu Asp Leu Leu Gly
                560                 565
aaa ctg ctg gcc caa cca gat gac tct gag cag act ttg 1906
Lys Leu Leu Ala Gln Pro Asp Asp Ser Glu Gln Thr Leu
570                 575                 580
cgg agg gac agc ctt atg tgc ttt act gtc ctg tgc gaa 1945
Arg Arg Asp Ser Leu Met Cys Phe Thr Val Leu Cys Glu
        585                 590                 595
gcc atg gat ggg aac agc cgg gcc atc tcc aaa gcc ttt 1984
```

```
                Ala Met Asp Gly Asn Ser Arg Ala Ile Ser Lys Ala Phe
                                600                 605
tac tcc agc ttg ctg acg aca cag cag gtt gtc ttg gat    2023
Tyr Ser Ser Leu Leu Thr Thr Gln Gln Val Val Leu Asp
        610                 615                 620
ggg ctc ctt cat ggc ttg aca gtt cca cag ctc cct gtc    2062
Gly Leu Leu His Gly Leu Thr Val Pro Gln Leu Pro Val
                625                 630
cac act ccc caa gga gcc ccg caa gtg agc cag cca ctg    2101
His Thr Pro Gln Gly Ala Pro Gln Val Ser Gln Pro Leu
635                 640                 645
cga gag cag agt gag gat ata cct gga gcc att tcc tct    2140
Arg Glu Gln Ser Glu Asp Ile Pro Gly Ala Ile Ser Ser
            650                 655                 660
gcc ctg gca gcc ata tgc act gct cct gtg gga ctg ccc    2179
Ala Leu Ala Ala Ile Cys Thr Ala Pro Val Gly Leu Pro
                665                 670
gac tgc tgg gat gcc aag gag cag gtc tgt tgg cat ttg    2218
Asp Cys Trp Asp Ala Lys Glu Gln Val Cys Trp His Leu
675                 680                 685
gca aat cag cta act gaa gac agc agc cag ctc agg cca    2257
Ala Asn Gln Leu Thr Glu Asp Ser Ser Gln Leu Arg Pro
            690                 695
tcc ctc atc tct ggc ctg cag cat ccc atc ctg tgc ctg    2296
Ser Leu Ile Ser Gly Leu Gln His Pro Ile Leu Cys Leu
700                 705                 710
cac ctt ctc aag gtt cta tac tcc tgc tgc ctt gtc agt    2335
His Leu Leu Lys Val Leu Tyr Ser Cys Cys Leu Val Ser
            715                 720                 725
gag ggc ctg tgc cgt ctt ctg ggg cag gag ccc ctg gcc    2374
Glu Gly Leu Cys Arg Leu Leu Gly Gln Glu Pro Leu Ala
                730                 735
ttg gaa tcc ctg ttt atg ttg att cag ggc aag gta aaa    2413
Leu Glu Ser Leu Phe Met Leu Ile Gln Gly Lys Val Lys
            740                 745                 750
gta gta gat tgg gaa gag tct act gaa gtg aca ctc tac    2452
Val Val Asp Trp Glu Glu Ser Thr Glu Val Thr Leu Tyr
                755                 760
ttc ctc tcc ctt ctt gtc ttt cgg ctc caa aac ctg cct    2491
Phe Leu Ser Leu Leu Val Phe Arg Leu Gln Asn Leu Pro
765                 770                 775
tgt gga atg gag aag cta ggc agt gac gtt gct act ctc    2530
Cys Gly Met Glu Lys Leu Gly Ser Asp Val Ala Thr Leu
            780                 785                 790
ttt acc cat tcg cat gtc gtc tct ctt gtg agt gca gca    2569
Phe Thr His Ser His Val Val Ser Leu Val Ser Ala Ala
                795                 800
gcc tgt cta ttg gga cag ctt ggt cag caa ggg gtg acc    2608
Ala Cys Leu Leu Gly Gln Leu Gly Gln Gln Gly Val Thr
805                 810                 815
ttt gac ctc cag ccc atg gaa tgg atg gct gca gcc aca    2647
Phe Asp Leu Gln Pro Met Glu Trp Met Ala Ala Ala Thr
            820                 825
cat gcc ttg tct gcc cct gca gag gtt cgg ttg act cca    2686
His Ala Leu Ser Ala Pro Ala Glu Val Arg Leu Thr Pro
830                 835                 840
cca ggt agt tgt gga ttc tat gat ggc ctc ctt atc ctt    2725
Pro Gly Ser Cys Gly Phe Tyr Asp Gly Leu Leu Ile Leu
            845                 850                 855
ctg ttg cag ctc ctc act gag cag ggg aag gct agc cta    2764
Leu Leu Gln Leu Leu Thr Glu Gln Gly Lys Ala Ser Leu
                860                 865
atc agg gat atg tcc agt tca gaa atg tgg acc gtt ttg    2803
Ile Arg Asp Met Ser Ser Ser Glu Met Trp Thr Val Leu
870                 875                 880
tgg cac cgc ttc tcc atg gtc ctg agg ctc ccc gag gag    2842
Trp His Arg Phe Ser Met Val Leu Arg Leu Pro Glu Glu
            885                 890
gca tct gca cag gaa ggg gag ctt tcg cta tcc agt cca    2881
Ala Ser Ala Gln Glu Gly Glu Leu Ser Leu Ser Ser Pro
895                 900                 905
cca agc cct gag cca gac tgg aca ctg att tct ccc cag    2920
Pro Ser Pro Glu Pro Asp Trp Thr Leu Ile Ser Pro Gln
            910                 915                 920
ggc atg gca gcc ctg ctg agc ctg gcc atg gcc acc ttt    2959
Gly Met Ala Ala Leu Leu Ser Leu Ala Met Ala Thr Phe
                925                 930
acc cag gag ccc cag tta tgc ctg agc tgc ctg tcc cag    2998
Thr Gln Glu Pro Gln Leu Cys Leu Ser Cys Leu Ser Gln
```

```
            935                 940                 945
cat gga agt atc ctc atg tcc atc ctg aag cat ctg ctt  3037
His Gly Ser Ile Leu Met Ser Ile Leu Lys His Leu Leu
                950                 955
tgc ccc agc ttc ctg aat caa ctg cgc cag gcg cct cat  3076
Cys Pro Ser Phe Leu Asn Gln Leu Arg Gln Ala Pro His
960                 965                 970
ggg tct gag ttt ctc cct gtc gtg gtg ctc tct gtc tgc  3115
Gly Ser Glu Phe Leu Pro Val Val Val Leu Ser Val Cys
            975                 980                 985
cag ctc ctt tgc ttc ccc ttt gcg ctg gac atg gat gct  3154
Gln Leu Leu Cys Phe Pro Phe Ala Leu Asp Met Asp Ala
                990                 995
gac ctc ctt ata gtt gtc ttg gcc gac ctc agg gac tca  3193
Asp Leu Leu Ile Val Val Leu Ala Asp Leu Arg Asp Ser
    1000                1005                1010
gaa gtt gca gcc cat ctg ctg cag gtc tgc tgc tac cat  3232
Glu Val Ala Ala His Leu Leu Gln Val Cys Cys Tyr His
            1015                1020
ctt ccg ttg atg caa gtg gag ctg ccc atc agc ctt ctc  3271
Leu Pro Leu Met Gln Val Glu Leu Pro Ile Ser Leu Leu
1025                1030                1035
aca cgc ctg gcc ctc atg gat ccc acc tct ctc aac cag  3310
Thr Arg Leu Ala Leu Met Asp Pro Thr Ser Leu Asn Gln
        1040                1045                1050
ttt gtg aac aca gtg tct gcc tcc cct aga acc atc gtc  3349
Phe Val Asn Thr Val Ser Ala Ser Pro Arg Thr Ile Val
            1055                1060
tcg ttt ctc tca gtt gcc ctc ctg agt gac cag cca ctg  3388
Ser Phe Leu Ser Val Ala Leu Leu Ser Asp Gln Pro Leu
    1065                1070                1075
ttg acc tcc gac ctt ctc tct ctg ctg gcc cat act gcc  3427
Leu Thr Ser Asp Leu Leu Ser Leu Leu Ala His Thr Ala
                1080                1085
agg gtc ctg tct ccc agc cac ttg tcc ttt atc caa gag  3466
Arg Val Leu Ser Pro Ser His Leu Ser Phe Ile Gln Glu
1090                1095                1100
ctt ctg gct ggc tct gat gaa tcc tat cgg ccc ctg cgc  3505
Leu Leu Ala Gly Ser Asp Glu Ser Tyr Arg Pro Leu Arg
            1105                1110                1115
agc ctc ctg ggc cac cca gag aat tct gtg cgg gca cac  3544
Ser Leu Leu Gly His Pro Glu Asn Ser Val Arg Ala His
                1120                1125
act tat agg ctc ctg gga cac ttg ctc caa cac agc atg  3583
Thr Tyr Arg Leu Leu Gly His Leu Leu Gln His Ser Met
            1130                1135                1140
gcc ctg cgt ggg gca ctg cag agc cag tct gga ctg ctc  3622
Ala Leu Arg Gly Ala Leu Gln Ser Gln Ser Gly Leu Leu
                1145                1150
agc ctt ctg ctg ctt ggg ctt gga gac aag gat cct gtt  3661
Ser Leu Leu Leu Leu Gly Leu Gly Asp Lys Asp Pro Val
1155                1160                1165
gtg cgg tgc agt gcc agc ttt gct gtg ggc aat gca gcc  3700
Val Arg Cys Ser Ala Ser Phe Ala Val Gly Asn Ala Ala
            1170                1175                1180
tac cag gct ggt cct ctg gga cct gcc ctg gca gct gca  3739
Tyr Gln Ala Gly Pro Leu Gly Pro Ala Leu Ala Ala Ala
                1185                1190
gtg ccc agt atg acc cag ctg ctt gga gat cct cag gct  3778
Val Pro Ser Met Thr Gln Leu Leu Gly Asp Pro Gln Ala
    1195                1200                1205
ggc atc cgg cgc aat gtt gca tca gct ctg ggc aac ttg  3817
Gly Ile Arg Arg Asn Val Ala Ser Ala Leu Gly Asn Leu
                1210                1215
gga cct gaa ggt ttg gga gag gag ctg tta cag tgc gaa  3856
Gly Pro Glu Gly Leu Gly Glu Glu Leu Leu Gln Cys Glu
1220                1225                1230
gta ccc cag cgg ctc cta gaa atg gca tgt gga gac ccc  3895
Val Pro Gln Arg Leu Leu Glu Met Ala Cys Gly Asp Pro
        1235                1240                1245
cag cca aat gtg aag gag gct gcc ctc att gcc ctc cgg  3934
Gln Pro Asn Val Lys Glu Ala Ala Leu Ile Ala Leu Arg
                1250                1255
agc ctg caa cag gag cct ggc atc cat cag gta ctg gtg  3973
Ser Leu Gln Gln Glu Pro Gly Ile His Gln Val Leu Val
    1260                1265                1270
tcc ctg ggt gcc agt gag aaa cta tcc ttg ctc tct ctg  4012
Ser Leu Gly Ala Ser Glu Lys Leu Ser Leu Leu Ser Leu
                1275                1280
```

-continued

```
ggg aat cag tca ctg cca cac agc agt cct agg cct gcc     4051
Gly Asn Gln Ser Leu Pro His Ser Ser Pro Arg Pro Ala
1285                1290                1295
tct gcc aaa cac tgc agg aaa ctc att cac ctc ctg agg     4090
Ser Ala Lys His Cys Arg Lys Leu Ile His Leu Leu Arg
        1300                1305                1310
cca gcc cat agc atg tgatt ccagattcct gcggtccagc         4130
Pro Ala His Ser Met
                1315
ctccaacttt ggtgccagct ctttcttatn taatacacaa gcgccaaytc  4180
aactgagagc taaagagact agaaaagaga taagctgcca actcaactga  4230
gaacaggaaa ctngaagaga tttatatata aagcttcttc cttctcccag  4280
atgcaggatg ttttcaacca gtaaatttta ttgctgttgg tgccagagaa  4330
gagtcccttt cttctctaca tccaggggcc nttttctcca ataatgtgcc  4380
tttaactcta gggacctgcc tcacggacct tagggaaaaa cctcaacctg  4430
aaagatctct tcctttctgg agctccttta atcttcccag caggttttg   4480
ccttagacgt gctggcccca ggacagtgat gaagacagag cctgtctcag  4530
ctctaggctg tggggatcaa tgccatcagt ccctgttatt gagggattat  4580
cccttagcca acattcctat ctgtgggtgg gcgtggagag tgtatctttt  4630
tttggggtgt gtgtgtatat gtgtgtgtgt atgtgtgtgt gtgtttaata  4680
gttctgtttg taaactctt taataaaagt tgtgcctcac catacttgaa   4730
gctcccagga caggggttga gaggctcaac ccctctttca gcttctatgt  4780
ggtgttggag gtgctggtat cgtgttcaca caaaaaaaaa aaaaaaaaaa  4830
aaaaaaaaaa aaaaaaaaaa aaaaaaaaaa aaaaaaaaaa aaaaaaaaaa  4880
```

<210> SEQ ID NO 2
<211> LENGTH: 1315
<212> TYPE: PRT
<213> ORGANISM: Homo sapiens

<400> SEQUENCE: 2

```
Met Glu Lys Tyr His Val Leu Glu Met Ile Gly Glu Gly Ser Phe
1               5                   10                  15
Gly Arg Val Tyr Lys Gly Arg Arg Lys Tyr Ser Ala Gln Val Val
                20                  25                  30
Ala Leu Lys Phe Ile Pro Lys Leu Gly Arg Ser Glu Lys Glu Leu
                35                  40                  45
Arg Asn Leu Gln Arg Glu Ile Glu Ile Met Arg Gly Leu Arg His
                50                  55                  60
Pro Asn Ile Val His Met Leu Asp Ser Phe Glu Thr Asp Lys Glu
                65                  70                  75
Val Val Val Val Thr Asp Tyr Ala Glu Gly Glu Leu Phe Gln Ile
                80                  85                  90
Leu Glu Asp Asp Gly Lys Leu Pro Glu Asp Gln Val Gln Ala Ile
                95                  100                 105
Ala Ala Gln Leu Val Ser Ala Leu Tyr Tyr Leu His Ser His Arg
                110                 115                 120
Ile Leu His Arg Asp Met Lys Pro Gln Asn Ile Leu Leu Ala Lys
                125                 130                 135
Gly Gly Gly Ile Lys Leu Cys Asp Phe Gly Phe Ala Arg Ala Met
                140                 145                 150
Ser Thr Asn Thr Met Val Leu Thr Ser Ile Lys Gly Thr Pro Leu
                155                 160                 165
Tyr Met Ser Pro Glu Leu Val Glu Glu Arg Pro Tyr Asp His Thr
                170                 175                 180
Ala Asp Leu Trp Ser Val Gly Cys Ile Leu Tyr Glu Leu Ala Val
                185                 190                 195
Gly Thr Pro Pro Phe Tyr Ala Thr Ser Ile Phe Gln Leu Val Ser
                200                 205                 210
Leu Ile Leu Lys Asp Pro Val Arg Trp Pro Ser Thr Ile Ser Pro
                215                 220                 225
Cys Phe Lys Asn Phe Leu Gln Gly Leu Leu Thr Lys Asp Pro Arg
                230                 235                 240
Gln Arg Leu Ser Trp Pro Asp Leu Leu Tyr His Pro Phe Ile Ala
                245                 250                 255
Gly His Val Thr Ile Ile Thr Glu Pro Ala Gly Pro Asp Leu Gly
                260                 265                 270
Thr Pro Phe Thr Ser Arg Leu Pro Pro Glu Leu Gln Val Leu Lys
                275                 280                 285
Asp Glu Gln Ala His Arg Leu Ala Pro Lys Gly Asn Gln Ser Arg
                290                 295                 300
Ile Leu Thr Gln Ala Tyr Lys Arg Met Ala Glu Glu Ala Met Gln
                305                 310                 315
Lys Lys His Gln Asn Thr Gly Pro Ala Leu Glu Gln Glu Asp Lys
                320                 325                 330
Thr Ser Lys Val Ala Pro Gly Thr Ala Pro Leu Pro Arg Leu Gly
                335                 340                 345
```

-continued

```
Ala Thr Pro Gln Glu Ser Ser Leu Leu Ala Gly Ile Leu Ala Ser
                350                 355                 360
Glu Leu Lys Ser Ser Trp Ala Lys Ser Gly Thr Gly Glu Val Pro
            365                 370                 375
Ser Ala Pro Arg Glu Asn Arg Thr Thr Pro Asp Cys Glu Arg Ala
        380                 385                 390
Phe Pro Glu Glu Arg Pro Glu Val Leu Gly Gln Arg Ser Thr Asp
            395                 400                 405
Val Val Asp Leu Glu Asn Glu Glu Pro Asp Ser Asp Asn Glu Trp
        410                 415                 420
Gln His Leu Leu Glu Thr Thr Glu Pro Val Pro Ile Gln Leu Lys
            425                 430                 435
Ala Pro Leu Thr Leu Leu Cys Asn Pro Asp Phe Cys Gln Arg Ile
        440                 445                 450
Gln Ser Gln Leu His Glu Ala Gly Gly Gln Ile Leu Lys Gly Ile
            455                 460                 465
Leu Glu Gly Ala Ser His Ile Leu Pro Ala Phe Arg Val Leu Ser
        470                 475                 480
Ser Leu Leu Ser Cys Ser Asp Ser Val Ala Leu Tyr Ser Phe
            485                 490                 495
Cys Arg Glu Ala Gly Leu Pro Gly Leu Leu Ser Leu Leu Arg
        500                 505                 510
His Ser Gln Glu Ser Asn Ser Leu Gln Gln Ser Trp Tyr Gly
            515                 520                 525
Thr Phe Leu Gln Asp Leu Met Ala Val Ile Gln Ala Tyr Phe Ala
        530                 535                 540
Cys Thr Phe Asn Leu Glu Arg Ser Gln Thr Ser Asp Ser Leu Gln
            545                 550                 555
Val Phe Gln Glu Ala Ala Asn Leu Phe Leu Asp Leu Leu Gly Lys
        560                 565                 570
Leu Leu Ala Gln Pro Asp Asp Ser Glu Gln Thr Leu Arg Arg Asp
            575                 580                 585
Ser Leu Met Cys Phe Thr Val Leu Cys Glu Ala Met Asp Gly Asn
            590                 595                 600
Ser Arg Ala Ile Ser Lys Ala Phe Tyr Ser Ser Leu Leu Thr Thr
        605                 610                 615
Gln Gln Val Val Leu Asp Gly Leu Leu His Gly Leu Thr Val Pro
            620                 625                 630
Gln Leu Pro Val His Thr Pro Gln Gly Ala Pro Gln Val Ser Gln
        635                 640                 645
Pro Leu Arg Glu Gln Ser Glu Asp Ile Pro Gly Ala Ile Ser Ser
            650                 655                 660
Ala Leu Ala Ala Ile Cys Thr Ala Pro Val Gly Leu Pro Asp Cys
        665                 670                 675
Trp Asp Ala Lys Glu Gln Val Cys Trp His Leu Ala Asn Gln Leu
            680                 685                 690
Thr Glu Asp Ser Ser Gln Leu Arg Pro Ser Leu Ile Ser Gly Leu
        695                 700                 705
Gln His Pro Ile Leu Cys Leu His Leu Leu Lys Val Leu Tyr Ser
            710                 715                 720
Cys Cys Leu Val Ser Glu Gly Leu Cys Arg Leu Leu Gly Gln Glu
        725                 730                 735
Pro Leu Ala Leu Glu Ser Leu Phe Met Leu Ile Gln Gly Lys Val
            740                 745                 750
Lys Val Val Asp Trp Glu Glu Ser Thr Glu Val Thr Leu Tyr Phe
        755                 760                 765
Leu Ser Leu Leu Val Phe Arg Leu Gln Asn Leu Pro Cys Gly Met
            770                 775                 780
Glu Lys Leu Gly Ser Asp Val Ala Thr Leu Phe Thr His Ser His
            785                 790                 795
Val Val Ser Leu Val Ser Ala Ala Ala Cys Leu Leu Gly Gln Leu
        800                 805                 810
Gly Gln Gln Gly Val Thr Phe Asp Leu Gln Pro Met Glu Trp Met
            815                 820                 825
Ala Ala Ala Thr His Ala Leu Ser Ala Pro Ala Glu Val Arg Leu
        830                 835                 840
Thr Pro Pro Gly Ser Cys Gly Phe Tyr Asp Gly Leu Leu Ile Leu
            845                 850                 855
Leu Leu Gln Leu Leu Thr Glu Gln Gly Lys Ala Ser Leu Ile Arg
        860                 865                 870
Asp Met Ser Ser Ser Glu Met Trp Thr Val Leu Trp His Arg Phe
            875                 880                 885
Ser Met Val Leu Arg Leu Pro Glu Glu Ala Ser Ala Gln Glu Gly
        890                 895                 900
Glu Leu Ser Leu Ser Ser Pro Pro Ser Pro Glu Pro Asp Trp Thr
            905                 910                 915
Leu Ile Ser Pro Gln Gly Met Ala Ala Leu Leu Ser Leu Ala Met
        920                 925                 930
Ala Thr Phe Thr Gln Glu Pro Gln Leu Cys Leu Ser Cys Leu Ser
```

```
                    935                 940                   945
        Gln His Gly Ser Ile Leu Met Ser Ile Leu Lys His Leu Leu Cys
                        950                 955                 960
        Pro Ser Phe Leu Asn Gln Leu Arg Gln Ala Pro His Gly Ser Glu
                    965                 970                   975
        Phe Leu Pro Val Val Val Leu Ser Val Cys Gln Leu Leu Cys Phe
                        980                 985                 990
        Pro Phe Ala Leu Asp Met Asp Ala Asp Leu Leu Ile Val Val Leu
                    995                 1000                  1005
        Ala Asp Leu Arg Asp Ser Glu Val Ala Ala His Leu Leu Gln Val
                        1010                1015                1020
        Cys Cys Tyr His Leu Pro Leu Met Gln Val Glu Leu Pro Ile Ser
                    1025                1030                  1035
        Leu Leu Thr Arg Leu Ala Leu Met Asp Pro Thr Ser Leu Asn Gln
                        1040                1045                1050
        Phe Val Asn Thr Val Ser Ala Ser Pro Arg Thr Ile Val Ser Phe
                    1055                1060                  1065
        Leu Ser Val Ala Leu Leu Ser Asp Gln Pro Leu Leu Thr Ser Asp
                        1070                1075                1080
        Leu Leu Ser Leu Leu Ala His Thr Ala Arg Val Leu Ser Pro Ser
                    1085                1090                  1095
        His Leu Ser Phe Ile Gln Glu Leu Leu Ala Gly Ser Asp Glu Ser
                        1100                1105                1110
        Tyr Arg Pro Leu Arg Ser Leu Leu Gly His Pro Glu Asn Ser Val
                    1115                1120                  1125
        Arg Ala His Thr Tyr Arg Leu Leu Gly His Leu Leu Gln His Ser
                        1130                1135                1140
        Met Ala Leu Arg Gly Ala Leu Gln Ser Gln Ser Gly Leu Leu Ser
                    1145                1150                  1155
        Leu Leu Leu Gly Leu Gly Asp Lys Asp Pro Val Val Arg Cys
                        1160                1165                1170
        Ser Ala Ser Phe Ala Val Gly Asn Ala Ala Tyr Gln Ala Gly Pro
                    1175                1180                  1185
        Leu Gly Pro Ala Leu Ala Ala Val Pro Ser Met Thr Gln Leu
                        1190                1195                1200
        Leu Gly Asp Pro Gln Ala Gly Ile Arg Arg Asn Val Ala Ser Ala
                    1205                1210                  1215
        Leu Gly Asn Leu Gly Pro Glu Gly Leu Gly Glu Glu Leu Leu Gln
                        1220                1225                1230
        Cys Glu Val Pro Gln Arg Leu Leu Glu Met Ala Cys Gly Asp Pro
                    1235                1240                  1245
        Gln Pro Asn Val Lys Glu Ala Ala Leu Ile Ala Leu Arg Ser Leu
                        1250                1255                1260
        Gln Gln Glu Pro Gly Ile His Gln Val Leu Val Ser Leu Gly Ala
                    1265                1270                  1275
        Ser Glu Lys Leu Ser Leu Leu Ser Leu Gly Asn Gln Ser Leu Pro
                        1280                1285                1290
        His Ser Ser Pro Arg Pro Ala Ser Ala Lys His Cys Arg Lys Leu
                    1295                1300                  1305
        Ile His Leu Leu Arg Pro Ala His Ser Met
                        1310                1315

<210> SEQ ID NO 3
<211> LENGTH: 193
<212> TYPE: DNA
<213> ORGANISM: Homo sapiens

<400> SEQUENCE: 3
cccgggctat gagcaccaat acaatggtgc tgacatccat caaaggcaca      50
    ccactctata tgtctccaga gctggtggag gagcgaccat acgaccacac     100
    agcggacctc tggtctgttg gctgcatact atatgaactg gcagtaggca     150
    cccctccctt ctaatgctac aagcatcttt cagctggtca gcc            193

<210> SEQ ID NO 4
<211> LENGTH: 5125
<212> TYPE: DNA
<213> ORGANISM: Homo sapiens

<400> SEQUENCE: 4
cccacgcgtc cgcccacgcg tccggggcgt cccagatgtt gtggaactgt      50
    ccctggatct atagctcttc accgtctcta ctttcttcct tctaagagat     100
    cctgaaacct ctgtc    atg gaa aag tac cac gtg ttg gag         139
                        Met Glu Lys Tyr His Val Leu Glu
                          1               5
    atg att gga gaa ggc tct ttt ggg agg gtg tac aag ggt         178
```

```
                Met Ile Gly Glu Gly Ser Phe Gly Arg Val Tyr Lys Gly
                     10                  15                  20
cga aga aaa tac agt gct cag gtc gtg gcc ctg aag ttc           217
Arg Arg Lys Tyr Ser Ala Gln Val Val Ala Leu Lys Phe
                 25                  30
atc cca aaa ttg ggg cgc tca gag aag gag ctg agg aat           256
Ile Pro Lys Leu Gly Arg Ser Glu Lys Glu Leu Arg Asn
 35                  40                  45
ttg caa cga gag att gaa ata atg cgg ggt ctg cgg cat           295
Leu Gln Arg Glu Ile Glu Ile Met Arg Gly Leu Arg His
         50                  55                  60
ccc aac att gtg cat atg ctt gac agc ttt gaa act gat           334
Pro Asn Ile Val His Met Leu Asp Ser Phe Glu Thr Asp
                 65                  70
aaa gag gtg gtg gtg aca gac tat gct gag gga gag           373
Lys Glu Val Val Val Thr Asp Tyr Ala Glu Gly Glu
 75                  80                  85
ctc ttt cag atc cta gaa gat gac gga aaa ctt cct gaa           412
Leu Phe Gln Ile Leu Glu Asp Asp Gly Lys Leu Pro Glu
         90                  95
gac cag gtt cag gcc att gct gcc cag ttg gtg tca gcc           451
Asp Gln Val Gln Ala Ile Ala Ala Gln Leu Val Ser Ala
100                 105                 110
ctg tac tat ctg cat tcc cac cgc atc cta cac cga gat           490
Leu Tyr Tyr Leu His Ser His Arg Ile Leu His Arg Asp
        115                 120                 125
atg aag cct cag aac atc ctc ctc gcc aag ggt ggt ggc           529
Met Lys Pro Gln Asn Ile Leu Leu Ala Lys Gly Gly Gly
                130                 135
atc aag ctc tgt gac ttt gga ttt gcc cgg gct atg agc           568
Ile Lys Leu Cys Asp Phe Gly Phe Ala Arg Ala Met Ser
140                 145                 150
acc aat aca atg gtg ctg aca tcc atc aaa ggc aca cca           607
Thr Asn Thr Met Val Leu Thr Ser Ile Lys Gly Thr Pro
                155                 160
ctc tat atg tct cca gag ctg gtg gag gag cga cca tac           646
Leu Tyr Met Ser Pro Glu Leu Val Glu Glu Arg Pro Tyr
165                 170                 175
gac cac aca gcg gac ctc tgg tct gtt ggc tgc ata cta           685
Asp His Thr Ala Asp Leu Trp Ser Val Gly Cys Ile Leu
        180                 185                 190
tat gaa ctg gca gta ggc acc cct ccc ttc tat gct aca           724
Tyr Glu Leu Ala Val Gly Thr Pro Pro Phe Tyr Ala Thr
                195                 200
agc atc ttt cag ctg gtc agc ctc att ctc aag gac cct           763
Ser Ile Phe Gln Leu Val Ser Leu Ile Leu Lys Asp Pro
        205                 210                 215
gtg cgc tgg ccc tca acc atc agt ccc tgc ttt aag aac           802
Val Arg Trp Pro Ser Thr Ile Ser Pro Cys Phe Lys Asn
                220                 225
ttc ctg cag gga ctg ctc acc aaa gac cca cgg cag cga           841
Phe Leu Gln Gly Leu Leu Thr Lys Asp Pro Arg Gln Arg
230                 235                 240
ctg tcc tgg cca gac ctc tta tat cac ccc ttt att gct           880
Leu Ser Trp Pro Asp Leu Leu Tyr His Pro Phe Ile Ala
        245                 250                 255
ggt cat gtc acc ata ata act gag cca gca ggc cca gat           919
Gly His Val Thr Ile Ile Thr Glu Pro Ala Gly Pro Asp
                260                 265
ttg ggg acc cca ttc acc agc cgc cta ccc cca gaa ctt           958
Leu Gly Thr Pro Phe Thr Ser Arg Leu Pro Pro Glu Leu
270                 275                 280
cag gtc cta aag gac gaa cag gcc cat cgg ttg gcc ccc           997
Gln Val Leu Lys Asp Glu Gln Ala His Arg Leu Ala Pro
        285                 290
aag ggt aat cag tct cgc atc ttg act cag gcc tat aaa           1036
Lys Gly Asn Gln Ser Arg Ile Leu Thr Gln Ala Tyr Lys
295                 300                 305
cgc atg gct gag gag gcc atg cag aag aaa cat cag aac           1075
Arg Met Ala Glu Glu Ala Met Gln Lys Lys His Gln Asn
        310                 315                 320
aca gga cct gcc ctt gag caa gag gac aag acc agc aag           1114
Thr Gly Pro Ala Leu Glu Gln Glu Asp Lys Thr Ser Lys
                325                 330
gtg gct cct ggc aca gcc cct ctg ccc aga ctc ggg gcc           1153
Val Ala Pro Gly Thr Ala Pro Leu Pro Arg Leu Gly Ala
335                 340                 345
act cct cag gaa tca agc ctc ctg gcc ggg atc tta gcc           1192
Thr Pro Gln Glu Ser Ser Leu Leu Ala Gly Ile Leu Ala
```

```
                    350                 355
tca gaa ttg aag agc agc tgg gct aaa tca ggg act gga  1231
Ser Glu Leu Lys Ser Ser Trp Ala Lys Ser Gly Thr Gly
360                 365                 370
gag gtg ccc tct gca cct cgg gaa aac cgg acc acc cca  1270
Glu Val Pro Ser Ala Pro Arg Glu Asn Arg Thr Thr Pro
        375                 380                 385
gat tgt gaa cga gca ttc cca gag gag agg cca gag gtg  1309
Asp Cys Glu Arg Ala Phe Pro Glu Glu Arg Pro Glu Val
                390                 395
ctg ggc cag cgg agc act gat gta gtg gac ctg gaa aat  1348
Leu Gly Gln Arg Ser Thr Asp Val Val Asp Leu Glu Asn
            400                 405                 410
gag gag cca gac agt gac aat gag tgg cag cac ctg cta  1387
Glu Glu Pro Asp Ser Asp Asn Glu Trp Gln His Leu Leu
                415                 420
gag acc act gag cct gtg cct att caa ctg aag gct cct  1426
Glu Thr Thr Glu Pro Val Pro Ile Gln Leu Lys Ala Pro
425                 430                 435
ctc acc ttg ctg tgt aat cct gac ttc tgc cag cgc atc  1465
Leu Thr Leu Leu Cys Asn Pro Asp Phe Cys Gln Arg Ile
            440                 445                 450
cag agt cag ctg cat gaa gct gga ggg cag atc ctg aaa  1504
Gln Ser Gln Leu His Glu Ala Gly Gly Gln Ile Leu Lys
                455                 460
ggc atc ttg gag ggt gct tcc cac atc ctg cct gca ttc  1543
Gly Ile Leu Glu Gly Ala Ser His Ile Leu Pro Ala Phe
465                 470                 475
cgg gtc ctg agc agt ctt ctc tcc agc tgc agt gat tct  1582
Arg Val Leu Ser Ser Leu Leu Ser Ser Cys Ser Asp Ser
            480                 485
gtt gcc ttg tat tcc ttc tgc cgg gag gca ggg ctt cct  1621
Val Ala Leu Tyr Ser Phe Cys Arg Glu Ala Gly Leu Pro
490                 495                 500
ggg ctg ctg ctg agt cta ctc agg cac agt cag gag agc  1660
Gly Leu Leu Leu Ser Leu Leu Arg His Ser Gln Glu Ser
        505                 510                 515
aac agc ctc cag cag caa tct tgg tat ggg acc ttc tta  1699
Asn Ser Leu Gln Gln Gln Ser Trp Tyr Gly Thr Phe Leu
                520                 525
cag gac ctg atg gct gtg att cag gcc tac ttt gcc tgt  1738
Gln Asp Leu Met Ala Val Ile Gln Ala Tyr Phe Ala Cys
            530                 535                 540
acc ttc aat ctg gag agg agc cag aca agt gac agc ctg  1777
Thr Phe Asn Leu Glu Arg Ser Gln Thr Ser Asp Ser Leu
                545                 550
cag gtg ttt cag gag gct gcc aac ctt ttt ctg gac ctg  1816
Gln Val Phe Gln Glu Ala Ala Asn Leu Phe Leu Asp Leu
555                 560                 565
ttg ggg aaa ctg ctg gcc caa cca gat gac tct gag cag  1855
Leu Gly Lys Leu Leu Ala Gln Pro Asp Asp Ser Glu Gln
        570                 575                 580
act ttg cag agg gac agc ctt atg tgc ttt act gtc ctg  1894
Thr Leu Gln Arg Asp Ser Leu Met Cys Phe Thr Val Leu
                585                 590
tgc gaa gcc atg gat ggg aac agc cgg gcc atc tcc aaa  1933
Cys Glu Ala Met Asp Gly Asn Ser Arg Ala Ile Ser Lys
            595                 600                 605
gcc ttt tac tcc agc ttg ctg acg aca cag cag gtt gtc  1972
Ala Phe Tyr Ser Ser Leu Leu Thr Thr Gln Gln Val Val
                610                 615
ttg gat ggg ctc ctt cat ggc ttg aca gtt cca cag ctc  2011
Leu Asp Gly Leu Leu His Gly Leu Thr Val Pro Gln Leu
620                 625                 630
cct gtc cac act ccc caa ggt aac cag agt gga gaa ggg  2050
Pro Val His Thr Pro Gln Gly Asn Gln Ser Gly Glu Gly
        635                 640                 645
agg ttc tct t gacttacttg ttgcataggt caggctccgc       2090
Arg Phe Ser
        648
tctttctatt gccatcacct agatcgcacc tggcatttag taggtgctca 2140
ataaataact gtgaactgag agaatgaatg gggatctgag ggaaacaaac 2190
agacctcatc ctgcattctt cccactccct taggttccct actcctgctg 2240
ccatgtcggt gagtactggt gctattgtct agggcaagag cctcaggcct 2290
ttgg    agt tac tct ttg ctt ttc tcc aca gga gcc ccg  2327
        Ser Tyr Ser Leu Leu Phe Ser Thr Gly Ala Pro
                1               5                   10
caa gtg agc cag cca ctg cga gag cag agt gag gat ata  2366
Gln Val Ser Gln Pro Leu Arg Glu Gln Ser Glu Asp Ile
```

```
                  15                  20
cct gga gcc att tcc tct gcc ctg gca gcc ata tgc act       2405
Pro Gly Ala Ile Ser Ser Ala Leu Ala Ala Ile Cys Thr
 25                  30                  35
gct cct gtg gga ctg ccc gac tgc tgg gat gcc aag gag       2444
Ala Pro Val Gly Leu Pro Asp Cys Trp Asp Ala Lys Glu
                 40                  45                  50
cag gtc tgt tgg cat ttg gca aat cag cta act gaa gac       2483
Gln Val Cys Trp His Leu Ala Asn Gln Leu Thr Glu Asp
                     55                  60
agc agc cag ctc agg cca tcc ctc atc tct ggc ctg cag       2522
Ser Ser Gln Leu Arg Pro Ser Leu Ile Ser Gly Leu Gln
 65                  70                  75
cat ccc atc ctg tgc ctg cac ctt ctc aag gtt cta tac       2561
His Pro Ile Leu Cys Leu His Leu Leu Lys Val Leu Tyr
                 80                  85
tcc tgc tgc ctt gtc agt gag ggc ctg tgc cgt ctt ctg       2600
Ser Cys Cys Leu Val Ser Glu Gly Leu Cys Arg Leu Leu
 90                  95                 100
ggg cag gag ccc ctg gcc ttg gaa tcc ctg ttt atg ttg       2639
Gly Gln Glu Pro Leu Ala Leu Glu Ser Leu Phe Met Leu
                105                 110                 115
att cag ggc aag gta aaa gta gta gat tgg gaa gag tct       2678
Ile Gln Gly Lys Val Lys Val Val Asp Trp Glu Glu Ser
                    120                 125
act gaa gtg aca ctc tac ttc ctc tcc ctt ctt gtc ttt       2717
Thr Glu Val Thr Leu Tyr Phe Leu Ser Leu Leu Val Phe
130                 135                 140
cgg ctc caa aac ctg cct tgt gga atg gag aag cta ggc       2756
Arg Leu Gln Asn Leu Pro Cys Gly Met Glu Lys Leu Gly
                145                 150
agt gac gtt gct act ctc ttt acc cat tcg cat gtc gtc       2795
Ser Asp Val Ala Thr Leu Phe Thr His Ser His Val Val
155                 160                 165
tct ctt gtg agt gca gca gcc tgt cta ttg gga cag ctt       2834
Ser Leu Val Ser Ala Ala Ala Cys Leu Leu Gly Gln Leu
                170                 175                 180
ggt cag caa ggg gtg acc ttt gac ctc cag ccc atg gaa       2873
Gly Gln Gln Gly Val Thr Phe Asp Leu Gln Pro Met Glu
                    185                 190
tgg atg gct gca gcc aca cat gcc ttg tct gcc cct gca       2912
Trp Met Ala Ala Ala Thr His Ala Leu Ser Ala Pro Ala
        195                 200                 205
gag gtt cgg ttg act cca cca ggt agt tgt gga ttc tat       2951
Glu Val Arg Leu Thr Pro Pro Gly Ser Cys Gly Phe Tyr
                210                 215
gat ggc ctc ctt atc ctt ctg ttg cag ctc ctc act gag       2990
Asp Gly Leu Leu Ile Leu Leu Leu Gln Leu Leu Thr Glu
220                 225                 230
cag ggg aag gct agc cta atc agg gat atg tcc agt tca       3029
Gln Gly Lys Ala Ser Leu Ile Arg Asp Met Ser Ser Ser
            235                 240                 245
gaa atg tgg acc gtt ttg tgg cac cgc ttc tcc atg gtc       3068
Glu Met Trp Thr Val Leu Trp His Arg Phe Ser Met Val
                250                 255
ctg agg ctc ccc gag gag gca tct gca cag gaa ggg gag       3107
Leu Arg Leu Pro Glu Glu Ala Ser Ala Gln Glu Gly Glu
        260                 265                 270
ctt tcg cta tcc agt cca cca agc cct gag cca gac tgg       3146
Leu Ser Leu Ser Ser Pro Pro Ser Pro Glu Pro Asp Trp
                275                 280
aca ctg att tct ccc cag ggc atg gca gcc ctg ctg agc       3185
Thr Leu Ile Ser Pro Gln Gly Met Ala Ala Leu Leu Ser
285                 290                 295
ctg gcc atg gcc acc ttt acc cag gag ccc cag tta tgc       3224
Leu Ala Met Ala Thr Phe Thr Gln Glu Pro Gln Leu Cys
            300                 305                 310
ctg agc tgc ctg tcc cag cat gga agt atc ctc atg tcc       3263
Leu Ser Cys Leu Ser Gln His Gly Ser Ile Leu Met Ser
                315                 320
atc ctg aag cat ctg ctt tgc ccc agc ttc ctg aat caa       3302
Ile Leu Lys His Leu Leu Cys Pro Ser Phe Leu Asn Gln
325                 330                 335
ctg cgc cag gcg cct cat ggg tct gag ttt ctc cct gtc       3341
Leu Arg Gln Ala Pro His Gly Ser Glu Phe Leu Pro Val
            340                 345
gtg gtg ctc tct gtc tgc cag ctc ctt tgc ttc ccc ttt       3380
Val Val Leu Ser Val Cys Gln Leu Leu Cys Phe Pro Phe
350                 355                 360
```

```
gcg ctg gac atg gat gct gac ctc ctt ata gtt gtc ttg   3419
Ala Leu Asp Met Asp Ala Asp Leu Leu Ile Val Val Leu
        365                 370                 375
gcc gac ctc agg gac tca gaa gtt gca gcc cat ctg ctg   3458
Ala Asp Leu Arg Asp Ser Glu Val Ala Ala His Leu Leu
                380                 385
cag gtc tgc tgc tac cat ctt ccg ttg atg caa gtg gag   3497
Gln Val Cys Cys Tyr His Leu Pro Leu Met Gln Val Glu
        390                 395                 400
ctg ccc atc agc ctt ctc aca cgc ctg gcc ctc atg gat   3536
Leu Pro Ile Ser Leu Leu Thr Arg Leu Ala Leu Met Asp
                405                 410
ccc acc tct ctc aac cag ttt gtg aac aca gtg tct gcc   3575
Pro Thr Ser Leu Asn Gln Phe Val Asn Thr Val Ser Ala
415                 420                 425
tcc cct aga acc atc gtc tcg ttt ctc tca gtt gcc ctc   3614
Ser Pro Arg Thr Ile Val Ser Phe Leu Ser Val Ala Leu
        430                 435                 440
ctg agt gac cag cca ctg ttg acc tcc gac ctt ctc tct   3653
Leu Ser Asp Gln Pro Leu Leu Thr Ser Asp Leu Leu Ser
                445                 450
ctg ctg gcc cat act gcc agg gtc ctg tct ccc agc cac   3692
Leu Leu Ala His Thr Ala Arg Val Leu Ser Pro Ser His
        455                 460                 465
ttg tcc ttt atc caa gag ctt ctg gct ggc tct gat gaa   3731
Leu Ser Phe Ile Gln Glu Leu Leu Ala Gly Ser Asp Glu
                470                 475
tcc tat cgg ccc ctg cgc agc ctc ctg ggc cac cca gag   3770
Ser Tyr Arg Pro Leu Arg Ser Leu Leu Gly His Pro Glu
480                 485                 490
aat tct gtg cgg gca cac act tat agg ctc ctg gga cac   3809
Asn Ser Val Arg Ala His Thr Tyr Arg Leu Leu Gly His
        495                 500                 505
ttg ctc caa cac agc atg gcc ctg cgt ggg gca ctg cag   3848
Leu Leu Gln His Ser Met Ala Leu Arg Gly Ala Leu Gln
                510                 515
agc cag tct gga ctg ctc agc ctt ctg ctg ctt ggg ctt   3887
Ser Gln Ser Gly Leu Leu Ser Leu Leu Leu Leu Gly Leu
        520                 525                 530
gga gac aag gat cct gtt gtg cgg tgc agt gcc agc ttt   3926
Gly Asp Lys Asp Pro Val Val Arg Cys Ser Ala Ser Phe
                535                 540
gct gtg ggc aat gca gcc tac cag gct ggt cct ctg gga   3965
Ala Val Gly Asn Ala Ala Tyr Gln Ala Gly Pro Leu Gly
545                 550                 555
cct gcc ctg gca gct gca gtg ccc agt atg acc cag ctg   4004
Pro Ala Leu Ala Ala Ala Val Pro Ser Met Thr Gln Leu
        560                 565                 570
ctt gga gat cct cag gct ggt atc cgg cgc aat gtt gca   4043
Leu Gly Asp Pro Gln Ala Gly Ile Arg Arg Asn Val Ala
                575                 580
tca gct ctg ggc aac ttg gga cct gaa ggt ttg gga gag   4082
Ser Ala Leu Gly Asn Leu Gly Pro Glu Gly Leu Gly Glu
        585                 590                 595
gag ctg tta cag tgc gaa gta ccc cag cgg ctc cta gaa   4121
Glu Leu Leu Gln Cys Glu Val Pro Gln Arg Leu Leu Glu
                600                 605
atg gca tgt gga gac ccc cag cca aat gtg aag gag gct   4160
Met Ala Cys Gly Asp Pro Gln Pro Asn Val Lys Glu Ala
610                 615                 620
gcc ctc att gcc ctc cgg agc ctg caa cag gag cct ggc   4199
Ala Leu Ile Ala Leu Arg Ser Leu Gln Gln Glu Pro Gly
        625                 630                 635
atc cat cag gta ctg gtg tcc ctg ggt gcc agt gag aaa   4238
Ile His Gln Val Leu Val Ser Leu Gly Ala Ser Glu Lys
                640                 645
cta tcc ttg ctc tct ctg ggg aat cag tca ctg cca cac   4277
Leu Ser Leu Leu Ser Leu Gly Asn Gln Ser Leu Pro His
650                 655                 660
agc agt cct agg cct gcc tct gcc aaa cac tgc agg aaa   4316
Ser Ser Pro Arg Pro Ala Ser Ala Lys His Cys Arg Lys
        665                 670
ctc att cac ctc ctg agg cca gcc cat agc atg t         4350
Leu Ile His Leu Leu Arg Pro Ala His Ser Met
675                 680                 685
gattccagat tcctgcggtc cagcctccaa ctttggttgc cagctctttc   4400
ttattctact acacaagccg ccaactcaac tgagagctaa agagactaga   4450
aaagagataa gctgccaact caactgagaa caagaaacta gaagagattt   4500
atatataaag cttcttccct ctcccagatg caggatgttt tcaaccagta   4550
```

-continued

```
          aattttattg ctgttggtgc cagagaagag tcctttcttc tctacatcca   4600
          ggggccttt  ctccaataat gtgcctttaa ctctagggac ctgcctcacg   4650
          gaccttaggg aaaaacctca acctgaaaga tctcttcctt tctggagctc   4700
          ctttaatctt cccagcaggt ttttgcctta gacgtgctgg ccccaggaca   4750
          gtgatgaaga cagagccgtg ctcagctcta ggctgtgggg atcaatgcca   4800
          tcagtccctg ttattgaggg attatccctt agccaacatt cctatctgtg   4850
          ggtgggcgtg gagagtgtat ctttttttgg ggtgtgtgtg tatatgtgtg   4900
          tgtgtatgtg tgtgtgtgtt taatagttct gtttgtaaac tcttttaata   4950
          aaagttgtgc ctcaccatac ttgaagctcc caggacaagg gttgagaggc   5000
          tcaaccctc  tttcagcttc tatgtggtgt tggaggtgct ggtatcgtgt   5050
          tcacacaaaa aaaaaaaaaa aaaaaaaaaa aaaaaaaaaa aaaaaaaaaa   5100
          aaaaaaaaaa aaaaaaaaaa aaaaa                              5125
```

<210> SEQ ID NO 5
<211> LENGTH: 648
<212> TYPE: PRT
<213> ORGANISM: Homo sapiens

<400> SEQUENCE: 5

```
    Met Glu Lys Tyr His Val Leu Glu Met Ile Gly Glu Gly Ser Phe
    1               5                  10                  15
    Gly Arg Val Tyr Lys Gly Arg Arg Lys Tyr Ser Ala Gln Val Val
                   20                  25                  30
    Ala Leu Lys Phe Ile Pro Lys Leu Gly Arg Ser Glu Lys Glu Leu
                   35                  40                  45
    Arg Asn Leu Gln Arg Glu Ile Glu Ile Met Arg Gly Leu Arg His
                   50                  55                  60
    Pro Asn Ile Val His Met Leu Asp Ser Phe Glu Thr Asp Lys Glu
                   65                  70                  75
    Val Val Val Val Thr Asp Tyr Ala Glu Gly Glu Leu Phe Gln Ile
                   80                  85                  90
    Leu Glu Asp Asp Gly Lys Leu Pro Glu Asp Gln Val Gln Ala Ile
                   95                 100                 105
    Ala Ala Gln Leu Val Ser Ala Leu Tyr Tyr Leu His Ser His Arg
                  110                 115                 120
    Ile Leu His Arg Asp Met Lys Pro Gln Asn Ile Leu Leu Ala Lys
                  125                 130                 135
    Gly Gly Gly Ile Lys Leu Cys Asp Phe Gly Phe Ala Arg Ala Met
                  140                 145                 150
    Ser Thr Asn Thr Met Val Leu Thr Ser Ile Lys Gly Thr Pro Leu
                  155                 160                 165
    Tyr Met Ser Pro Glu Leu Val Glu Glu Arg Pro Tyr Asp His Thr
                  170                 175                 180
    Ala Asp Leu Trp Ser Val Gly Cys Ile Leu Tyr Glu Leu Ala Val
                  185                 190                 195
    Gly Thr Pro Pro Phe Tyr Ala Thr Ser Ile Phe Gln Leu Val Ser
                  200                 205                 210
    Leu Ile Leu Lys Asp Pro Val Arg Trp Pro Ser Thr Ile Ser Pro
                  215                 220                 225
    Cys Phe Lys Asn Phe Leu Gln Gly Leu Leu Thr Lys Asp Pro Arg
                  230                 235                 240
    Gln Arg Leu Ser Trp Pro Asp Leu Leu Tyr His Pro Phe Ile Ala
                  245                 250                 255
    Gly His Val Thr Ile Ile Thr Glu Pro Ala Gly Pro Asp Leu Gly
                  260                 265                 270
    Thr Pro Phe Thr Ser Arg Leu Pro Pro Glu Leu Gln Val Leu Lys
                  275                 280                 285
    Asp Glu Gln Ala His Arg Leu Ala Pro Lys Gly Asn Gln Ser Arg
                  290                 295                 300
    Ile Leu Thr Gln Ala Tyr Lys Arg Met Ala Glu Glu Ala Met Gln
                  305                 310                 315
    Lys Lys His Gln Asn Thr Gly Pro Ala Leu Glu Gln Glu Asp Lys
                  320                 325                 330
    Thr Ser Lys Val Ala Pro Gly Thr Ala Pro Leu Pro Arg Leu Gly
                  335                 340                 345
    Ala Thr Pro Gln Glu Ser Ser Leu Leu Ala Gly Ile Leu Ala Ser
                  350                 355                 360
    Glu Leu Lys Ser Ser Trp Ala Lys Ser Gly Thr Gly Glu Val Pro
                  365                 370                 375
    Ser Ala Pro Arg Glu Asn Arg Thr Thr Pro Asp Cys Glu Arg Ala
                  380                 385                 390
    Phe Pro Glu Glu Arg Pro Glu Val Leu Gly Gln Arg Ser Thr Asp
                  395                 400                 405
    Val Val Asp Leu Glu Asn Gly Glu Pro Asp Ser Asp Asn Glu Trp
                  410                 415                 420
    Gln His Leu Leu Glu Thr Thr Glu Pro Val Pro Ile Gln Leu Lys
                  425                 430                 435
```

```
        Ala Pro Leu Thr Leu Leu Cys Asn Pro Asp Phe Cys Gln Arg Ile
                        440                 445                 450
        Gln Ser Gln Leu His Glu Ala Gly Gly Gln Ile Leu Lys Gly Ile
                        455                 460                 465
        Leu Glu Gly Ala Ser His Ile Leu Pro Ala Phe Arg Val Leu Ser
                        470                 475                 480
        Ser Leu Leu Ser Ser Cys Ser Asp Ser Val Ala Leu Tyr Ser Phe
                        485                 490                 495
        Cys Arg Glu Ala Gly Leu Pro Gly Leu Leu Ser Leu Leu Arg
                        500                 505                 510
        His Ser Gln Glu Ser Asn Ser Leu Gln Gln Ser Trp Tyr Gly
                        515                 520                 525
        Thr Phe Leu Gln Asp Leu Met Ala Val Ile Gln Ala Tyr Phe Ala
                        530                 535                 540
        Cys Thr Phe Asn Leu Glu Arg Ser Gln Thr Ser Asp Ser Leu Gln
                        545                 550                 555
        Val Phe Gln Glu Ala Ala Asn Leu Phe Leu Asp Leu Leu Gly Lys
                        560                 565                 570
        Leu Leu Ala Gln Pro Asp Asp Ser Glu Gln Thr Leu Gln Arg Asp
                        575                 580                 585
        Ser Leu Met Cys Phe Thr Val Leu Cys Glu Ala Met Asp Gly Asn
                        590                 595                 600
        Ser Arg Ala Ile Ser Lys Ala Phe Tyr Ser Ser Leu Leu Thr Thr
                        605                 610                 615
        Gln Gln Val Val Leu Asp Gly Leu Leu His Gly Leu Thr Val Pro
                        620                 625                 630
        Gln Leu Pro Val His Thr Pro Gln Gly Asn Gln Ser Gly Glu Gly
                        635                 640                 645
        Arg Phe Ser
                        648

<210> SEQ ID NO 6
<211> LENGTH: 5252
<212> TYPE: DNA
<213> ORGANISM: Homo sapiens

<400> SEQUENCE: 6
ggagcttgga gctcctaggc tgggggcgtc ccagatgttg tggaactgtc    50
        cctggatcta tagctcttca ccgtctctac tttcttcctt ctaagagatc   100
        ctgaaacctc tgtc atg gaa aag tac cac gtg ttg gag atg       141
                     Met Glu Lys Tyr His Val Leu Glu Met
                       1               5
        att gga gaa ggc tct ttt ggg agg gtg tac aag ggt cga      180
        Ile Gly Glu Gly Ser Phe Gly Arg Val Tyr Lys Gly Arg
         10              15                  20
        aga aaa tac agt gct cag gtc gtg gcc ctg aag ttc atc      219
        Arg Lys Tyr Ser Ala Gln Val Val Ala Leu Lys Phe Ile
                     25                  30                  35
        cca aaa ttg ggg cgc tca gag aag gag ctg agg aat ttg      258
        Pro Lys Leu Gly Arg Ser Glu Lys Glu Leu Arg Asn Leu
                         40                  45
        caa cga gag att gaa ata atg cgg ggt ctg cgg cat ccc      297
        Gln Arg Glu Ile Glu Ile Met Arg Gly Leu Arg His Pro
                     50                  55                  60
        aac att gtg cat atg ctt gac agc ttt gaa act gat aaa      336
        Asn Ile Val His Met Leu Asp Ser Phe Glu Thr Asp Lys
                     65                          70
        gag gtg gtg gtg gtg aca gac tat gct gag gga gag ctc      375
        Glu Val Val Val Val Thr Asp Tyr Ala Glu Gly Glu Leu
         75                  80                  85
        ttt cag atc cta gaa gat gac gga aaa ctt cct gaa gac      414
        Phe Gln Ile Leu Glu Asp Asp Gly Lys Leu Pro Glu Asp
                     90                  95                 100
        cag gtt cag gcc att gct gcc cag ttg gtg tca gcc ctg      453
        Gln Val Gln Ala Ile Ala Ala Gln Leu Val Ser Ala Leu
                         105                 110
        tac tat ctg cat tcc cac cgc atc cta cac cga gat atg      492
        Tyr Tyr Leu His Ser His Arg Ile Leu His Arg Asp Met
                     115                 120                 125
        aag cct cag aac atc ctc ctc gcc aag ggt ggt ggc atc      531
        Lys Pro Gln Asn Ile Leu Leu Ala Lys Gly Gly Gly Ile
                         130                 135
        aag ctc tgt gac ttt gga ttt gcc cgg gct atg agc acc      570
        Lys Leu Cys Asp Phe Gly Phe Ala Arg Ala Met Ser Thr
        140                 145                 150
        aat aca atg gtg ctg aca tcc atc aaa ggc aca cca ctc      609
        Asn Thr Met Val Leu Thr Ser Ile Lys Gly Thr Pro Leu
```

-continued

```
                155                      160                      165
tat atg tct cca gag ctg gtg gag gag cga cca tac gac   648
Tyr Met Ser Pro Glu Leu Val Glu Glu Arg Pro Tyr Asp
                      170                      175
cac aca gcg gac ctc tgg tct gtt ggc tgc ata cta tat   687
His Thr Ala Asp Leu Trp Ser Val Gly Cys Ile Leu Tyr
180                      185                      190
gaa ctg gca gta ggc acc cct ccc ttc tat gct aca agc   726
Glu Leu Ala Val Gly Thr Pro Pro Phe Tyr Ala Thr Ser
                195                      200
atc ttt cag ctg gtc agc ctc att ctc aag gac cct gtg   765
Ile Phe Gln Leu Val Ser Leu Ile Leu Lys Asp Pro Val
205                      210                      215
cgc tgg ccc tca acc atc agt ccc tgc ttt aag aac ttc   804
Arg Trp Pro Ser Thr Ile Ser Pro Cys Phe Lys Asn Phe
                220                      225                      230
ctg cag gga ctg ctc acc aaa gac cca cgg cag cga ctg   843
Leu Gln Gly Leu Leu Thr Lys Asp Pro Arg Gln Arg Leu
                      235                      240
tcc tgg cca gac ctc tta tat cac ccc ttt att gct ggt   882
Ser Trp Pro Asp Leu Leu Tyr His Pro Phe Ile Ala Gly
            245                      250                      255
cat gtc acc ata ata act gag cca gca ggc cca gat ttg   921
His Val Thr Ile Ile Thr Glu Pro Ala Gly Pro Asp Leu
                  260                      265
ggg acc cca ttc acc agc cgc cta ccc cca gaa ctt cag   960
Gly Thr Pro Phe Thr Ser Arg Leu Pro Pro Glu Leu Gln
270                      275                      280
gtc cta aag gac gaa cag gcc cat cgg ttg gcc ccc aag   999
Val Leu Lys Asp Glu Gln Ala His Arg Leu Ala Pro Lys
            285                      290                      295
ggt aat cag tct cgc atc ttg act cag gcc tat aaa cgc   1038
Gly Asn Gln Ser Arg Ile Leu Thr Gln Ala Tyr Lys Arg
                  300                      305
atg gct gag gag gcc atg cag aag aaa cat cag aac aca   1077
Met Ala Glu Glu Ala Met Gln Lys Lys His Gln Asn Thr
310                      315                      320
gga cct gcc ctt gag caa gag gac aag acc agc aag gtg   1116
Gly Pro Ala Leu Glu Gln Glu Asp Lys Thr Ser Lys Val
                325                      330
gct cct ggc aca gcc cct ctg ccc aga ctc ggg gcc act   1155
Ala Pro Gly Thr Ala Pro Leu Pro Arg Leu Gly Ala Thr
335                      340                      345
cct cag gaa tca agc ctc ctg gcc ggg atc tta gcc tca   1194
Pro Gln Glu Ser Ser Leu Leu Ala Gly Ile Leu Ala Ser
                350                      355                      360
gaa ttg aag agc agc tgg gct aaa tca ggg act gga gag   1233
Glu Leu Lys Ser Ser Trp Ala Lys Ser Gly Thr Gly Glu
                      365                      370
gtg ccc tct gca cct cgg gaa aac cgg acc acc cca gat   1272
Val Pro Ser Ala Pro Arg Glu Asn Arg Thr Thr Pro Asp
375                      380                      385
tgt gaa cga gca ttc cca gag gag agg cca gag gtg ctg   1311
Cys Glu Arg Ala Phe Pro Glu Glu Arg Pro Glu Val Leu
                      390                      395
ggc cag cgg agc act gat gta gtg gac ctg gaa aat gag   1350
Gly Gln Arg Ser Thr Asp Val Val Asp Leu Glu Asn Glu
400                      405                      410
gag cca gac agt gac aat gag tgg cag cac ctg cta gag   1389
Glu Pro Asp Ser Asp Asn Glu Trp Gln His Leu Leu Glu
                415                      420                      425
acc act gag cct gtg cct att caa ctg aag gct cct ctc   1428
Thr Thr Glu Pro Val Pro Ile Gln Leu Lys Ala Pro Leu
                      430                      435
acc ttg ctg tgt aat cct gac ttc tgc cag cgc atc cag   1467
Thr Leu Leu Cys Asn Pro Asp Phe Cys Gln Arg Ile Gln
440                      445                      450
agt cag ctg cat gaa gct gga ggg cag atc ctg aaa ggc   1506
Ser Gln Leu His Glu Ala Gly Gly Gln Ile Leu Lys Gly
                455                      460
atc ttg gag ggt gct tcc cac atc ctg cct gca ttc cgg   1545
Ile Leu Glu Gly Ala Ser His Ile Leu Pro Ala Phe Arg
465                      470                      475
gtc ctg agc agt ctt ctc tcc agc tgc agt gat tct gtt   1584
Val Leu Ser Ser Leu Leu Ser Ser Cys Ser Asp Ser Val
                480                      485                      490
gcc ttg tat tcc ttc tgc cgg gag gca ggg ctt cct ggg   1623
Ala Leu Tyr Ser Phe Cys Arg Glu Ala Gly Leu Pro Gly
                      495                      500
```

```
ctg ctg ctg agt cta ctc agg cac agt cag gag agc aac   1662
Leu Leu Leu Ser Leu Leu Arg His Ser Gln Glu Ser Asn
        505                 510                 515
agc ctc cag cag caa tct tgg tat ggg acc ttc tta cag   1701
Ser Leu Gln Gln Gln Ser Trp Tyr Gly Thr Phe Leu Gln
            520                 525
gac ctg atg gct gtg att cag gcc tac ttt gcc tgt acc   1740
Asp Leu Met Ala Val Ile Gln Ala Tyr Phe Ala Cys Thr
530                 535                 540
ttc aat ctg gag agg agc cag aca agt gac agc ctg cag   1779
Phe Asn Leu Glu Arg Ser Gln Thr Ser Asp Ser Leu Gln
            545                 550                 555
gtg ttt cag gag gct gcc aac ctt ttt ctg gac ctg ttg   1818
Val Phe Gln Glu Ala Ala Asn Leu Phe Leu Asp Leu Leu
                560                 565
ggg aaa ctg ctg gcc caa cca gat gac tct gag cag act   1857
Gly Lys Leu Leu Ala Gln Pro Asp Asp Ser Glu Gln Thr
570                 575                 580
ttg cgg agg gac agc ctt atg tgc ttt act gtc ctg tgc   1896
Leu Arg Arg Asp Ser Leu Met Cys Phe Thr Val Leu Cys
            585                 590
gaa gcc atg gat ggg aac agc cgg gcc atc tcc aaa gcc   1935
Glu Ala Met Asp Gly Asn Ser Arg Ala Ile Ser Lys Ala
595                 600                 605
ttt tac tcc agc ttg ctg acg aca cag cag gtt gtc ttg   1974
Phe Tyr Ser Ser Leu Leu Thr Thr Gln Gln Val Val Leu
            610                 615                 620
gat ggg ctc ctt cat ggc ttg aca gtt cca cag ctc cct   2013
Asp Gly Leu Leu His Gly Leu Thr Val Pro Gln Leu Pro
                625                 630
gtc cac act ccc caa ggt tcc cta ctc ctg ctg cca tgt   2052
Val His Thr Pro Gln Gly Ser Leu Leu Leu Leu Pro Cys
        635                 640                 645
cgg tga g t actggtgcta ttgtctaggg caagagcctc          2090
Arg Xaa
    648
aggcctttgg  agt tac tct ttg ctt ttc tcc aca gga gcc   2130
            Ser Tyr Ser Leu Leu Phe Ser Thr Gly Ala
                1               5                 10
ccg caa gtg agc cag cca ctg cga gag cag agt gag gat   2169
Pro Gln Val Ser Gln Pro Leu Arg Glu Gln Ser Glu Asp
            15                  20
ata cct gga gcc att tcc tct gcc ctg gca gcc ata tgc   2208
Ile Pro Gly Ala Ile Ser Ser Ala Leu Ala Ala Ile Cys
        25                  30                  35
act gct cct gtg gga ctg ccc gac tgc tgg gat gcc aag   2247
Thr Ala Pro Val Gly Leu Pro Asp Cys Trp Asp Ala Lys
                40                  45
gag cag gtc tgt tgg cat ttg gca aat cag cta act gaa   2286
Glu Gln Val Cys Trp His Leu Ala Asn Gln Leu Thr Glu
50                  55                  60
gac agc agc cag ctc agg cca tcc ctc atc tct ggc ctg   2325
Asp Ser Ser Gln Leu Arg Pro Ser Leu Ile Ser Gly Leu
            65                  70                  75
cag cat ccc atc ctg tgc ctg cac ctt ctc aag gtt cta   2364
Gln His Pro Ile Leu Cys Leu His Leu Leu Lys Val Leu
                80                  85
tac tcc tgc tgc ctt gtc agt gag ggc ctg tgc cgt ctt   2403
Tyr Ser Cys Cys Leu Val Ser Glu Gly Leu Cys Arg Leu
        90                  95                  100
ctg ggg cag gag ccc ctg gcc ttg gaa tcc ctg ttt atg   2442
Leu Gly Gln Glu Pro Leu Ala Leu Glu Ser Leu Phe Met
                105                 110
ttg att cag ggc aag gta aaa gta gta gat tgg gaa gag   2481
Leu Ile Gln Gly Lys Val Lys Val Val Asp Trp Glu Glu
115                 120                 125
tct act gaa gtg aca ctc tac ttc ctc tcc ctt ctt gtc   2520
Ser Thr Glu Val Thr Leu Tyr Phe Leu Ser Leu Leu Val
            130                 135                 140
ttt cgg ctc caa aac ctg cct tgt gga atg gag aag cta   2559
Phe Arg Leu Gln Asn Leu Pro Cys Gly Met Glu Lys Leu
                145                 150
ggc agt gac gtt gct act ctc ttt acc cat tcg cat gtc   2598
Gly Ser Asp Val Ala Thr Leu Phe Thr His Ser His Val
155                 160                 165
gtc tct ctt gtg agt gca gca gcc tgt cta ttg gga cag   2637
Val Ser Leu Val Ser Ala Ala Ala Cys Leu Leu Gly Gln
            170                 175
ctt ggt cag caa ggg gtg acc ttt gac ctc cag ccc atg   2676
```

```
       Leu Gly Gln Gln Gly Val Thr Phe Asp Leu Gln Pro Met
       180                 185                 190
gaa tgg atg gct gca gcc aca cat gcc ttg tct gcc cct      2715
Glu Trp Met Ala Ala Ala Thr His Ala Leu Ser Ala Pro
        195                 200                 205
gca gag ctc ctc act gag gta cag atg gat ctt ggg atg      2754
Ala Glu Leu Leu Thr Glu Val Gln Met Asp Leu Gly Met
                    210                 215
gat ggg aag taaagag agaggaactg ggcattttgg ggagcctctg     2800
Asp Gly Lys
    220 221
gaccagagga atgaagaagc aacccacagc cttccctctc aagctactgt   2850
gcctgtgata gccttggaac ttccccgcct gccctcagta ctgacccttt   2900
gaaggaaacc attcgctgcg tcccctggga tccagtggga gataaaatga   2950
attccctggg tttcagcaga catacacatg agttgtgagg tcagagggtt   3000
aaggtttgat aagaaaatga aataagacga cagggaaata ctaggtggga   3050
aagcggaagg aattatttct gggacttcct ttacttgtaa gtcagggaca   3100
ggaatgaata aaagcatttg gattcctgac ttctgtcttt cccccgccc    3150
tctttcactt ttatctctag caggggaagg ctagcctaat caggggatatg  3200
tccagttcag aaatgtggac cgttttgtgg caccgcttct ccatggtcct   3250
gaggctcccc gaggaggcat ctgcacagga agggagctt cgctatcca     3300
gtccaccaag ccctgagcca gactggacac tgatttctcc ccagggcatg   3350
gcagccctgc tgagcctggc catggccacc tttacccagg agccccagtt   3400
atgcctgagc tgcctgtccc agcatggaag tatcctcatg tccatcctga   3450
agcatctgct tgccccagc ttcctgaatc aactgcgcca ggcgcctcat    3500
gggtctgagt ttctccctgt cgtggtgctc tctgtctgcc agctcctttg   3550
cttccccttt gcgctggaca tgatgctga cctccttata ggtgtcttgg    3600
ccgacctcag ggactcagaa gttgcagccc atctgctgca ggtctgctgc   3650
taccatcttc cgttgatgca agtggagctg cccatcagcc ttctcacacg   3700
cctggccctc atggatccca cctctctcaa ccagtttgtg aacacagtgt   3750
ctgcctcccc tagaaccatc gtctcgtttc tctcagttgc cctcctgagt   3800
gaccagccac tgttgacctc cgaccttctc tctctgctgg cccatactgt   3850
cagggtcctg tctcccagcc acttgtcctt tatccaagag cttctggctg   3900
gctctgatga atcctatcgg ccctgcgca gcctcctggg ccacccagag    3950
aattctgtgc gggcacacac ttataggctc tgggacact tgctccaaca    4000
cagcatggcc ctgcgtgggg cactgcagag ccagtctgca ctgctcagcc   4050
ttctgctgct tgggcttgga gacaaggatc ctgttgtgcg gtgcagtgcc   4100
agctttgctg tgggcaatgc agcctaccag gctggtcctc tgggacctgc   4150
cctggcagct gcagtgccca gtatgaccca gctgcttgga gatcctcagg   4200
ctggtatccg gcgcaatgtt gcatcagctc tgggcaactt gggacctgaa   4250
ggtttgggag aggagctgtt acagtgcgaa gtaccccagc ggctcctaga   4300
aatggcatgt ggagacccc agccaaatgt gaaggaggct gccctcattg    4350
ccctccggag cctgcaacag gagcctggca tccatcaggt actggtgtcc   4400
ctgggtgcca gtgagaaact atccttgctc tctctgggga atcagtcact   4450
gccacacagc agtcctaggc ctgcctctgc caaacactgc aggaaactca   4500
ttcacctcct gaggccagcc catagcatgt gattccagat tcctgcggtc   4550
cagcctccaa ctttggttgc cagctctttc ttattctact acacaagccg   4600
ccaactcaac tgagagctaa agagactaga aaagagataa gctgccaact   4650
caactgagaa caagaaacta gaagagattt atatataaag cttcttcctt   4700
ctcccagatg caggatgttt tcaaccagta aattttattg ctgttggtgc   4750
cagagaagag tcctttcttc tctacatcca ggggccttt ctccaataat    4800
gtgcctttaa ctctagggac ctgcctcacg gaccttaggg aaaaacctca   4850
acctgaaaga tctcttcctt tctggagctc ctttaatctt cccagcaggt   4900
ttttgcctta gacgtgctgg ccccaggaca gtgatgaaga cagagcctgt   4950
ctcagctcta ggctgtgggg atcaatgcca tcagtccctg ttattgaggg   5000
attatccctt agccaacatt cctatctgtg ggtgggcgtg gagagtgtat   5050
cttttttgg ggtgtgtgtg tatatgtgtg tgtgtatgtg tgtgtgtgtt    5100
taatagttct gtttgtaaac tcttttaata aaagttgtgc ctcaccatac   5150
ttgaagctcc caggacaagg gttgagaggc tcaacccctc tttcagcttc   5200
tatgtggtgt tggaggtgct ggtatcgtgt tcacacaaaa aaaaaaaaaa   5250
aa                                                      5252
```

<210> SEQ ID NO 7
<211> LENGTH: 647
<212> TYPE: PRT
<213> ORGANISM: Homo sapiens

<400> SEQUENCE: 7

```
Met Glu Lys Tyr His Val Leu Glu Met Ile Gly Glu Gly Ser Phe
  1               5                  10                  15
Gly Arg Val Tyr Lys Gly Arg Arg Lys Tyr Ser Ala Gln Val Val
                 20                  25                  30
Ala Leu Lys Phe Ile Pro Lys Leu Gly Arg Ser Glu Lys Glu Leu
                 35                  40                  45
Arg Asn Leu Gln Arg Glu Ile Glu Ile Met Arg Gly Leu Arg His
                 50                  55                  60
Pro Asn Ile Val His Met Leu Asp Ser Phe Glu Thr Asp Lys Glu
```

```
                        65                    70                    75
    Val Val Val Val Thr Asp Tyr Ala Glu Gly Glu Leu Phe Gln Ile
                            80                    85                    90
    Leu Glu Asp Asp Gly Lys Leu Pro Glu Asp Gln Val Gln Ala Ile
                            95                   100                   105
    Ala Ala Gln Leu Val Ser Ala Leu Tyr Tyr Leu His Ser His Arg
                           110                   115                   120
    Ile Leu His Arg Asp Met Lys Pro Gln Asn Ile Leu Leu Ala Lys
                           125                   130                   135
    Gly Gly Gly Ile Lys Leu Cys Asp Phe Gly Phe Ala Arg Ala Met
                           140                   145                   150
    Ser Thr Asn Thr Met Val Leu Thr Ser Ile Lys Gly Thr Pro Leu
                           155                   160                   165
    Tyr Met Ser Pro Glu Leu Val Glu Glu Arg Pro Tyr Asp His Thr
                           170                   175                   180
    Ala Asp Leu Trp Ser Val Gly Cys Ile Leu Tyr Glu Leu Ala Val
                           185                   190                   195
    Gly Thr Pro Pro Phe Tyr Ala Thr Ser Ile Phe Gln Leu Val Ser
                           200                   205                   210
    Leu Ile Leu Lys Asp Pro Val Arg Trp Pro Ser Thr Ile Ser Pro
                           215                   220                   225
    Cys Phe Lys Asn Phe Leu Gln Gly Leu Leu Thr Lys Asp Pro Arg
                           230                   235                   240
    Gln Arg Leu Ser Trp Pro Asp Leu Leu Tyr His Pro Phe Ile Ala
                           245                   250                   255
    Gly His Val Thr Ile Ile Thr Glu Pro Ala Gly Pro Asp Leu Gly
                           260                   265                   270
    Thr Pro Phe Thr Ser Arg Leu Pro Pro Glu Leu Gln Val Leu Lys
                           275                   280                   285
    Asp Glu Gln Ala His Arg Leu Ala Pro Lys Gly Asn Gln Ser Arg
                           290                   295                   300
    Ile Leu Thr Gln Ala Tyr Lys Arg Met Ala Glu Glu Ala Met Gln
                           305                   310                   315
    Lys Lys His Gln Asn Thr Gly Pro Ala Leu Glu Gln Glu Asp Lys
                           320                   325                   330
    Thr Ser Lys Val Ala Pro Gly Thr Ala Pro Leu Pro Arg Leu Gly
                           335                   340                   345
    Ala Thr Pro Gln Glu Ser Ser Leu Leu Ala Gly Ile Leu Ala Ser
                           350                   355                   360
    Glu Leu Lys Ser Ser Trp Ala Lys Ser Gly Thr Gly Glu Val Pro
                           365                   370                   375
    Ser Ala Pro Arg Glu Asn Arg Thr Thr Pro Asp Cys Glu Arg Ala
                           380                   385                   390
    Phe Pro Glu Glu Arg Pro Glu Val Leu Gly Gln Arg Ser Thr Asp
                           395                   400                   405
    Val Val Asp Leu Glu Asn Glu Glu Pro Asp Ser Asp Asn Glu Trp
                           410                   415                   420
    Gln His Leu Leu Glu Thr Thr Glu Pro Val Pro Ile Gln Leu Lys
                           425                   430                   435
    Ala Pro Leu Thr Leu Leu Cys Asn Pro Asp Phe Cys Gln Arg Ile
                           440                   445                   450
    Gln Ser Gln Leu His Glu Ala Gly Gly Gln Ile Leu Lys Gly Ile
                           455                   460                   465
    Leu Glu Gly Ala Ser His Ile Leu Pro Ala Phe Arg Val Leu Ser
                           470                   475                   480
    Ser Leu Leu Ser Ser Cys Ser Asp Ser Val Ala Leu Tyr Ser Phe
                           485                   490                   495
    Cys Arg Glu Ala Gly Leu Pro Gly Leu Leu Ser Leu Leu Arg
                           500                   505                   510
    His Ser Gln Glu Ser Asn Ser Leu Gln Gln Ser Trp Tyr Gly
                           515                   520                   525
    Thr Phe Leu Gln Asp Leu Met Ala Val Ile Gln Ala Tyr Phe Ala
                           530                   535                   540
    Cys Thr Phe Asn Leu Glu Arg Ser Gln Thr Ser Asp Ser Leu Gln
                           545                   550                   555
    Val Phe Gln Glu Ala Ala Asn Leu Phe Leu Asp Leu Leu Gly Lys
                           560                   565                   570
    Leu Leu Ala Gln Pro Asp Asp Ser Glu Gln Thr Leu Arg Arg Asp
                           575                   580                   585
    Ser Leu Met Cys Phe Thr Val Leu Cys Glu Ala Met Asp Gly Asn
                           590                   595                   600
    Ser Arg Ala Ile Ser Lys Ala Phe Tyr Ser Ser Leu Leu Thr Thr
                           605                   610                   615
    Gln Gln Val Val Leu Asp Gly Leu Leu His Gly Leu Thr Val Pro
                           620                   625                   630
    Gln Leu Pro Val His Thr Pro Gln Gly Ser Leu Leu Leu Leu Pro
                           635                   640                   645
    Cys Arg
    647
```

```
<210> SEQ ID NO 8
<211> LENGTH: 32
<212> TYPE: DNA
<213> ORGANISM: artificial sequence
<220> FEATURE:
<223> OTHER INFORMATION: artificial sequence

<400> SEQUENCE: 8
caatacaatg gtgctgacat ccatcaaagg ca            32

<210> SEQ ID NO 9
<211> LENGTH: 23
<212> TYPE: DNA
<213> ORGANISM: artificial sequence
<220> FEATURE:
<223> OTHER INFORMATION: artificial sequence

<400> SEQUENCE: 9
gaagggaggg gtgcctactg cca                      23

<210> SEQ ID NO 10
<211> LENGTH: 38
<212> TYPE: DNA
<213> ORGANISM: artificial sequence
<220> FEATURE:
<223> OTHER INFORMATION: artificial sequence

<400> SEQUENCE: 10
ctccagctct ggagacatat agagtggtgt gcctttga      38

<210> SEQ ID NO 11
<211> LENGTH: 60
<212> TYPE: DNA
<213> ORGANISM: artificial sequence
<220> FEATURE:
<223> OTHER INFORMATION: artificial sequence

<400> SEQUENCE: 11
ccatcgatgt acccatacga cgtcccagac tacgctgaaa agtaccacgt    50
     gttggagatg                                                60

<210> SEQ ID NO 12
<211> LENGTH: 32
<212> TYPE: DNA
<213> ORGANISM: artificial sequence
<220> FEATURE:
<223> OTHER INFORMATION: artificial sequence

<400> SEQUENCE: 12
gctctagact aaggggcagg tcctgtgttc tg            32

<210> SEQ ID NO 13
<211> LENGTH: 21
<212> TYPE: DNA
<213> ORGANISM: artificial sequence
<220> FEATURE:
<223> OTHER INFORMATION: artificial sequence

<400> SEQUENCE: 13
ctgacgacac agcaggttgt c                        21

<210> SEQ ID NO 14
<211> LENGTH: 21
<212> TYPE: DNA
<213> ORGANISM: artificial sequence
```

```
<220> FEATURE:
<223> OTHER INFORMATION: artificial sequence

<400> SEQUENCE: 14
cagatgcttc aggatggaca t                                    21

<210> SEQ ID NO 15
<211> LENGTH: 19
<212> TYPE: DNA
<213> ORGANISM: artificial sequence
<220> FEATURE:
<223> OTHER INFORMATION: artificial sequence

<400> SEQUENCE: 15
agagtagcaa cgtcactgc                                       19

<210> SEQ ID NO 16
<211> LENGTH: 21
<212> TYPE: DNA
<213> ORGANISM: artificial sequence
<220> FEATURE:
<223> OTHER INFORMATION: artificial sequence

<400> SEQUENCE: 16
cctcactgac aaggcagcag g                                    21

<210> SEQ ID NO 17
<211> LENGTH: 21
<212> TYPE: DNA
<213> ORGANISM: artificial sequence
<220> FEATURE:
<223> OTHER INFORMATION: artificial sequence

<400> SEQUENCE: 17
cccgaggagg catctgcaca g                                    21

<210> SEQ ID NO 18
<211> LENGTH: 21
<212> TYPE: DNA
<213> ORGANISM: artificial sequence
<220> FEATURE:
<223> OTHER INFORMATION: artificial sequence

<400> SEQUENCE: 18
cagaacttca ggtcctaaag g                                    21

<210> SEQ ID NO 19
<211> LENGTH: 32
<212> TYPE: DNA
<213> ORGANISM: artificial sequence
<220> FEATURE:
<223> OTHER INFORMATION: artificial sequence

<400> SEQUENCE: 19
tcgacaagca gggaacaccc aagtagaagc tc                        32

<210> SEQ ID NO 20
<211> LENGTH: 32
<212> TYPE: DNA
<213> ORGANISM: artificial sequence
<220> FEATURE:
<223> OTHER INFORMATION: artificial sequence

<400> SEQUENCE: 20
tcgacaagca gggaagtggg aagtagaagc tc                        32
```

```
<210> SEQ ID NO 21
<211> LENGTH: 685
<212> TYPE: PRT
<213> ORGANISM: Homo sapiens

<400> SEQUENCE: 21

Ser Tyr Ser Leu Leu Phe Ser Thr Gly Ala Pro Gln Val Ser Gln
      1               5                  10                  15
     Pro Leu Arg Glu Gln Ser Glu Asp Ile Pro Gly Ala Ile Ser Ser
                     20                  25                  30
     Ala Leu Ala Ala Ile Cys Thr Ala Pro Val Gly Leu Pro Asp Cys
                     35                  40                  45
     Trp Asp Ala Lys Glu Gln Val Cys Trp His Leu Ala Asn Gln Leu
                     50                  55                  60
     Thr Glu Asp Ser Ser Gln Leu Arg Pro Ser Leu Ile Ser Gly Leu
                     65                  70                  75
     Gln His Pro Ile Leu Cys Leu His Leu Leu Lys Val Leu Tyr Ser
                     80                  85                  90
     Cys Cys Leu Val Ser Glu Gly Leu Cys Arg Leu Leu Gly Gln Glu
                     95                 100                 105
     Pro Leu Ala Leu Glu Ser Leu Phe Met Leu Ile Gln Gly Lys Val
                    110                 115                 120
     Lys Val Val Asp Trp Glu Glu Ser Thr Glu Val Thr Leu Tyr Phe
                    125                 130                 135
     Leu Ser Leu Leu Val Phe Arg Leu Gln Asn Leu Pro Cys Gly Met
                    140                 145                 150
     Glu Lys Leu Gly Ser Asp Val Ala Thr Leu Phe Thr His Ser His
                    155                 160                 165
     Val Val Ser Leu Val Ser Ala Ala Cys Leu Leu Gly Gln Leu
                    170                 175                 180
     Gly Gln Gln Gly Val Thr Phe Asp Leu Gln Pro Met Glu Trp Met
                    185                 190                 195
     Ala Ala Ala Thr His Ala Leu Ser Ala Pro Ala Glu Val Arg Leu
                    200                 205                 210
     Thr Pro Pro Gly Ser Cys Gly Phe Tyr Asp Gly Leu Leu Ile Leu
                    215                 220                 225
     Leu Leu Gln Leu Leu Thr Glu Gln Gly Lys Ala Ser Leu Ile Arg
                    230                 235                 240
     Asp Met Ser Ser Ser Glu Met Trp Thr Val Leu Trp His Arg Phe
                    245                 250                 255
     Ser Met Val Leu Arg Leu Pro Glu Glu Ala Ser Ala Gln Glu Gly
                    260                 265                 270
     Glu Leu Ser Leu Ser Ser Pro Ser Pro Glu Pro Asp Trp Thr
                    275                 280                 285
     Leu Ile Ser Pro Gln Gly Met Ala Ala Leu Leu Ser Leu Ala Met
                    290                 295                 300
     Ala Thr Phe Thr Gln Glu Pro Gln Leu Cys Leu Ser Cys Leu Ser
                    305                 310                 315
     Gln His Gly Ser Ile Leu Met Ser Ile Leu Lys His Leu Leu Cys
                    320                 325                 330
     Pro Ser Phe Leu Asn Gln Leu Arg Gln Ala Pro His Gly Ser Glu
                    335                 340                 345
     Phe Leu Pro Val Val Val Leu Ser Val Cys Gln Leu Leu Cys Phe
                    350                 355                 360
     Pro Phe Ala Leu Asp Met Asp Ala Asp Leu Leu Ile Val Val Leu
                    365                 370                 375
     Ala Asp Leu Arg Asp Ser Glu Val Ala Ala His Leu Leu Gln Val
                    380                 385                 390
     Cys Cys Tyr His Leu Pro Leu Met Gln Val Glu Leu Pro Ile Ser
                    395                 400                 405
     Leu Leu Thr Arg Leu Ala Leu Met Asp Pro Thr Ser Leu Asn Gln
                    410                 415                 420
     Phe Val Asn Thr Val Ser Ala Ser Pro Arg Thr Ile Val Ser Phe
                    425                 430                 435
     Leu Ser Val Ala Leu Leu Ser Asp Gln Pro Leu Leu Thr Ser Asp
                    440                 445                 450
     Leu Leu Ser Leu Leu Ala His Thr Ala Arg Val Leu Ser Pro Ser
                    455                 460                 465
     His Leu Ser Phe Ile Gln Glu Leu Leu Ala Gly Ser Asp Glu Ser
                    470                 475                 480
     Tyr Arg Pro Leu Arg Ser Leu Leu Gly His Pro Glu Asn Ser Val
                    485                 490                 495
     Arg Ala His Thr Tyr Arg Leu Leu Gly His Leu Leu Gln His Ser
                    500                 505                 510
     Met Ala Leu Arg Gly Ala Leu Gln Ser Gln Ser Gly Leu Leu Ser
                    515                 520                 525
     Leu Leu Leu Leu Gly Leu Gly Asp Lys Asp Pro Val Val Arg Cys
```

```
                    530                    535                    540
    Ser Ala Ser Phe Ala Val Gly Asn Ala Ala Tyr Gln Ala Gly Pro
                        545                    550                    555
    Leu Gly Pro Ala Leu Ala Ala Val Pro Ser Met Thr Gln Leu
                        560                    565                    570
    Leu Gly Asp Pro Gln Ala Gly Ile Arg Arg Asn Val Ala Ser Ala
                        575                    580                    585
    Leu Gly Asn Leu Gly Pro Glu Gly Leu Gly Glu Glu Leu Leu Gln
                        590                    595                    600
    Cys Glu Val Pro Gln Arg Leu Leu Glu Met Ala Cys Gly Asp Pro
                        605                    610                    615
    Gln Pro Asn Val Lys Glu Ala Ala Leu Ile Ala Leu Arg Ser Leu
                        620                    625                    630
    Gln Gln Glu Pro Gly Ile His Gln Val Leu Val Ser Leu Gly Ala
                        635                    640                    645
    Ser Glu Lys Leu Ser Leu Leu Ser Leu Gly Asn Gln Ser Leu Pro
                        650                    655                    660
    His Ser Ser Pro Arg Pro Ala Ser Ala Lys His Cys Arg Lys Leu
                        665                    670                    675
    Ile His Leu Leu Arg Pro Ala His Ser Met
                        680                    685
```

<210> SEQ ID NO 22
<211> LENGTH: 221
<212> TYPE: PRT
<213> ORGANISM: Homo sapiens

<400> SEQUENCE: 22

```
    Ser Tyr Ser Leu Leu Phe Ser Thr Gly Ala Pro Gln Val Ser Gln
      1               5                   10                  15
    Pro Leu Arg Glu Gln Ser Glu Asp Ile Pro Gly Ala Ile Ser Ser
                        20                  25                  30
    Ala Leu Ala Ala Ile Cys Thr Ala Pro Val Gly Leu Pro Asp Cys
                        35                  40                  45
    Trp Asp Ala Lys Glu Gln Val Cys Trp His Leu Ala Asn Gln Leu
                        50                  55                  60
    Thr Glu Asp Ser Ser Gln Leu Arg Pro Ser Leu Ile Ser Gly Leu
                        65                  70                  75
    Gln His Pro Ile Leu Cys Leu His Leu Leu Lys Val Leu Tyr Ser
                        80                  85                  90
    Cys Cys Leu Val Ser Glu Gly Leu Cys Arg Leu Leu Gly Gln Glu
                        95                  100                 105
    Pro Leu Ala Leu Glu Ser Leu Phe Met Leu Ile Gln Gly Lys Val
                        110                 115                 120
    Lys Val Val Asp Trp Glu Glu Ser Thr Glu Val Thr Leu Tyr Phe
                        125                 130                 135
    Leu Ser Leu Leu Val Phe Arg Leu Gln Asn Leu Pro Cys Gly Met
                        140                 145                 150
    Glu Lys Leu Gly Ser Asp Val Ala Thr Leu Phe Thr His Ser His
                        155                 160                 165
    Val Val Ser Leu Val Ser Ala Ala Ala Cys Leu Leu Gly Gln Leu
                        170                 175                 180
    Gly Gln Gln Gly Val Thr Phe Asp Leu Gln Pro Met Glu Trp Met
                        185                 190                 195
    Ala Ala Ala Thr His Ala Leu Ser Ala Pro Ala Glu Leu Leu Thr
                        200                 205                 210
    Glu Val Gln Met Asp Leu Gly Met Asp Gly Lys
                        215                 220 221
```

<210> SEQ ID NO 23
<211> LENGTH: 795
<212> TYPE: PRT
<213> ORGANISM: Drosophila virilis

<400> SEQUENCE: 23

```
    Met Asp Arg Tyr Ala Val Ser Ser Leu Val Gly Gln Gly Ser Phe
      1               5                   10                  15
    Gly Cys Val Tyr Lys Ala Gln Arg Arg Asp Asp Asp Lys Val Val
                        20                  25                  30
    Ala Ile Lys Val Ile Ser Lys Arg Gly Arg Ser Asn Arg Glu Leu
                        35                  40                  45
    Lys Asn Leu Arg Arg Glu Cys Asp Ile Gln Ala Arg Leu Lys His
                        50                  55                  60
    Pro His Val Ile Glu Met Val Glu Ser Phe Glu Ser Lys Phe Asp
                        65                  70                  75
```

-continued

```
Leu Phe Val Val Thr Glu Phe Ala Leu Met Asp Leu His Arg Tyr
              80                  85                  90
Leu Ser Phe Asn Gly Ala Met Pro Glu Glu His Ala Gln Arg Val
              95                 100                 105
Val Cys His Leu Val Ser Ala Leu Tyr Tyr Leu His Ser Asn Arg
             110                 115                 120
Ile Leu His Arg Asp Leu Lys Pro Gln Asn Val Leu Leu Asp Lys
             125                 130                 135
Asn Met His Ala Lys Leu Cys Asp Phe Gly Leu Ala Arg Asn Met
             140                 145                 150
Thr Met Gly Thr His Val Leu Thr Ser Ile Lys Gly Thr Pro Leu
             155                 160                 165
Tyr Met Ala Pro Glu Leu Leu Ala Glu Gln Pro Tyr Asp His Gln
             170                 175                 180
Ala Asp Met Trp Ser Leu Gly Cys Ile Ala Tyr Glu Ser Met Ala
             185                 190                 195
Gly Gln Pro Pro Phe Cys Ala Thr Ser Ile Leu His Leu Val Lys
             200                 205                 210
Leu Ile Lys His Glu Asp Val Lys Trp Pro Ser Thr Leu Ser Ser
             215                 220                 225
Glu Cys Arg Ser Phe Leu Gln Gly Leu Leu Glu Lys Asp Pro Ser
             230                 235                 240
Met Arg Ile Ser Trp Thr Gln Leu Leu Cys His Pro Phe Val Glu
             245                 250                 255
Gly Lys Leu Tyr Ile Ala Glu Val Gln Ala Ala Gln Thr Ser Pro
             260                 265                 270
Phe Ile Asn Pro Gln Leu Ala Lys Asp Thr Lys Lys Ser Gln Gln
             275                 280                 285
Leu Arg His Val Gly Ala Asp Leu Gly Asp Val Leu Ala Ala Leu
             290                 295                 300
Lys Leu Ser Asp Val Ala Asn Glu Asn Leu Ser Thr Ser Arg Asp
             305                 310                 315
Ser Ile Asn Ala Ile Ala Pro Ser Asp Ile Glu Gln Leu Glu Thr
             320                 325                 330
Asp Val Glu Asp Asn Val His Arg Leu Ile Val Pro Phe Ala Asp
             335                 340                 345
Ile Ser Tyr Arg Glu Leu Pro Cys Gly Thr Ala Ala Ala Ala Arg
             350                 355                 360
Arg Ala Gly Ala Met Pro Leu Ile Asn Ser Gln Thr Cys Phe Val
             365                 370                 375
Ser Gly Asn Ser Asn Met Ile Leu Asn His Leu Asn Asp Asn Phe
             380                 385                 390
Ala Ile Glu Ala Pro Ala Ser Ser Ala Thr Lys Ser Met Lys Ser
             395                 400                 405
Lys Leu Lys Leu Ala Leu Asn Ile Lys Gln Ser Arg Ser Lys Asp
             410                 415                 420
Leu Glu Lys Arg Lys Leu Ser Gln Asn Leu Asp Asn Phe Ser Leu
             425                 430                 435
Arg Leu Gly Gln Ser Ile Asp Ile Glu Val Gln Arg Lys Thr Thr
             440                 445                 450
Glu Met Leu Thr Gln Gln Ser Gln Ala Gln Gln Leu Gln Asp Arg
             455                 460                 465
Lys Thr Gln Gln Leu Lys Gln Ser Met His Ser Thr Asn Asp Glu
             470                 475                 480
Lys Leu Ser Ser Asp Asn Ser Pro Pro Cys Leu Leu Pro Gly Trp
             485                 490                 495
Asp Ser Cys Asp Glu Ser Gln Ser Pro Ile Glu Asn Asp Glu
             500                 505                 510
Trp Leu Ala Phe Leu His Arg Ser Ile Gln Glu Leu Leu Asp Gly
             515                 520                 525
Glu Phe Asp Ser Leu Lys Gln His Asn Leu Val Ser Ile Ile Val
             530                 535                 540
Ala Pro Leu Arg Asn Ser Lys Ala Ile Pro Lys Val Leu Gln Ser
             545                 550                 555
Val Ala Gln Leu Leu Ser Leu Pro Phe Val Leu Ala Glu Gln His
             560                 565                 570
Leu Val Ala Glu Ala Ile Lys Gly Val Tyr Ile Asp Val Lys Leu
             575                 580                 585
Val Pro Asn Leu Met Tyr Ala Cys Lys Leu Leu Ser Gln Arg
             590                 595                 600
His Leu Thr Asp Ser Ala Ala Ser Leu Pro Ala Gly Thr Gly Val
             605                 610                 615
Ser Leu Ser Arg Thr Val Arg Ser Cys Ser Asp Leu Ser Ala Glu
             620                 625                 630
Glu Met Ser Thr Ala Cys Ser Leu Tyr Glu Leu Val Cys His Leu
             635                 640                 645
Val His Gln Gln Gln Gln Phe Leu Thr Gln Phe Cys Asp Ala Val
             650                 655                 660
Ala Ile Leu Ala Val Asn Asp Met Phe Ile Asn Phe Leu Thr His
```

```
                              665                 670                 675
         Asp Phe Lys Asp Ser Arg Pro Val Arg Leu Ala Ser Cys Met Leu
                              680                 685                 690
         Ala Leu Phe Cys Cys Val Leu Arg Glu Leu Pro Glu Asn Ala Glu
                              695                 700                 705
         Leu Val Glu Lys Ile Val Phe Asp Ser Arg Leu Gln Leu Ala Val
                              710                 715                 720
         Leu Leu Gln Ser Arg His His Leu Arg Gln Arg Ala Cys Gln
                              725                 730                 735
         Met Leu Leu Leu Ala Arg Phe Ser Leu Arg Gly Val Gln Cys
                              740                 745                 750
         Ile Trp Ser Gly Glu Leu Lys Ser Ala Leu Gln Ala Trp Pro Met
                              755                 760                 765
         Gln Gln Thr Cys Gln Ser Leu Arg Leu Glu Ala Ala Gln Thr Leu
                              770                 775                 780
         Asp Glu Leu Ser Gln Phe Ser Phe Val Ala Gln Ala Thr Ala
                              785                 790                 795

<210> SEQ ID NO 24
<211> LENGTH: 260
<212> TYPE: PRT
<213> ORGANISM: Homo sapiens

<400> SEQUENCE: 24

Met Glu Lys Tyr His Val Leu Glu Met Ile Gly Glu Gly Ser Phe
           1               5                  10                  15
         Gly Arg Val Tyr Lys Gly Arg Arg Lys Tyr Ser Ala Gln Val Val
                              20                  25                  30
         Ala Leu Lys Phe Ile Pro Lys Leu Gly Arg Ser Glu Lys Glu Leu
                              35                  40                  45
         Arg Asn Leu Gln Arg Glu Ile Glu Ile Met Arg Gly Leu Arg His
                              50                  55                  60
         Pro Asn Ile Val His Met Leu Asp Ser Phe Glu Thr Asp Lys Glu
                              65                  70                  75
         Val Val Val Val Thr Asp Tyr Ala Glu Gly Glu Leu Phe Gln Ile
                              80                  85                  90
         Leu Glu Asp Asp Gly Lys Leu Pro Glu Asp Gln Val Gln Ala Ile
                              95                 100                 105
         Ala Ala Gln Leu Val Ser Ala Leu Tyr Tyr Leu His Ser His Arg
                             110                 115                 120
         Ile Leu His Arg Asp Met Lys Pro Gln Asn Ile Leu Leu Ala Lys
                             125                 130                 135
         Gly Gly Gly Ile Lys Leu Cys Asp Phe Gly Phe Ala Arg Ala Met
                             140                 145                 150
         Ser Thr Asn Thr Met Val Leu Thr Ser Ile Lys Gly Thr Pro Leu
                             155                 160                 165
         Tyr Met Ser Pro Glu Leu Val Glu Glu Arg Pro Tyr Asp His Thr
                             170                 175                 180
         Ala Asp Leu Trp Ser Val Gly Cys Ile Leu Tyr Glu Leu Ala Val
                             185                 190                 195
         Gly Thr Pro Pro Phe Tyr Ala Thr Ser Ile Phe Gln Leu Val Ser
                             200                 205                 210
         Leu Ile Leu Lys Asp Pro Val Arg Trp Pro Ser Thr Ile Ser Pro
                             215                 220                 225
         Cys Phe Lys Asn Phe Leu Gln Gly Leu Leu Thr Lys Asp Pro Arg
                             230                 235                 240
         Gln Arg Leu Ser Trp Pro Asp Leu Leu Tyr His Pro Phe Ile Ala
                             245                 250                 255
         Gly His Val Thr Ile
                             260

<210> SEQ ID NO 25
<211> LENGTH: 1315
<212> TYPE: PRT
<213> ORGANISM: artificial sequence
<220> FEATURE:
<223> OTHER INFORMATION: artificial sequence

<400> SEQUENCE: 25

Met Glu Lys Tyr His Val Leu Glu Met Ile Gly Glu Gly Ser Phe
           1               5                  10                  15
         Gly Arg Val Tyr Lys Gly Arg Arg Lys Tyr Ser Ala Gln Val Val
                              20                  25                  30
         Ala Leu Arg Phe Ile Pro Lys Leu Gly Arg Ser Glu Lys Glu Leu
                              35                  40                  45
```

```
Arg Asn Leu Gln Arg Glu Ile Glu Ile Met Arg Gly Leu Arg His
                50                       55                      60
Pro Asn Ile Val His Met Leu Asp Ser Phe Glu Thr Asp Lys Glu
                65                       70                      75
Val Val Val Val Thr Asp Tyr Ala Glu Gly Glu Leu Phe Gln Ile
                80                       85                      90
Leu Glu Asp Asp Gly Lys Leu Pro Glu Asp Gln Val Gln Ala Ile
                95                      100                     105
Ala Ala Gln Leu Val Ser Ala Leu Tyr Tyr Leu His Ser His Arg
               110                      115                     120
Ile Leu His Arg Asp Met Lys Pro Gln Asn Ile Leu Leu Ala Lys
               125                      130                     135
Gly Gly Gly Ile Lys Leu Cys Asp Phe Gly Phe Ala Arg Ala Met
               140                      145                     150
Ser Thr Asn Thr Met Val Leu Thr Ser Ile Lys Gly Thr Pro Leu
               155                      160                     165
Tyr Met Ser Pro Glu Leu Val Glu Glu Arg Pro Tyr Asp His Thr
               170                      175                     180
Ala Asp Leu Trp Ser Val Gly Cys Ile Leu Tyr Glu Leu Ala Val
               185                      190                     195
Gly Thr Pro Pro Phe Tyr Ala Thr Ser Ile Phe Gln Leu Val Ser
               200                      205                     210
Leu Ile Leu Lys Asp Pro Val Arg Trp Pro Ser Thr Ile Ser Pro
               215                      220                     225
Cys Phe Lys Asn Phe Leu Gln Gly Leu Leu Thr Lys Asp Pro Arg
               230                      235                     240
Gln Arg Leu Ser Trp Pro Asp Leu Leu Tyr His Pro Phe Ile Ala
               245                      250                     255
Gly His Val Thr Ile Ile Thr Glu Pro Ala Gly Pro Asp Leu Gly
               260                      265                     270
Thr Pro Phe Thr Ser Arg Leu Pro Pro Glu Leu Gln Val Leu Lys
               275                      280                     285
Asp Glu Gln Ala His Arg Leu Ala Pro Lys Gly Asn Gln Ser Arg
               290                      295                     300
Ile Leu Thr Gln Ala Tyr Lys Arg Met Ala Glu Glu Ala Met Gln
               305                      310                     315
Lys Lys His Gln Asn Thr Gly Pro Ala Leu Glu Gln Glu Asp Lys
               320                      325                     330
Thr Ser Lys Val Ala Pro Gly Thr Ala Pro Leu Pro Arg Leu Gly
               335                      340                     345
Ala Thr Pro Gln Glu Ser Ser Leu Leu Ala Gly Ile Leu Ala Ser
               350                      355                     360
Glu Leu Lys Ser Ser Trp Ala Lys Ser Gly Thr Gly Glu Val Pro
               365                      370                     375
Ser Ala Pro Arg Glu Asn Arg Thr Thr Pro Asp Cys Glu Arg Ala
               380                      385                     390
Phe Pro Glu Glu Arg Pro Glu Val Leu Gly Gln Arg Ser Thr Asp
               395                      400                     405
Val Val Asp Leu Glu Asn Glu Glu Pro Asp Ser Asp Asn Glu Trp
               410                      415                     420
Gln His Leu Leu Glu Thr Thr Glu Pro Val Pro Ile Gln Leu Lys
               425                      430                     435
Ala Pro Leu Thr Leu Cys Asn Pro Asp Phe Cys Gln Arg Ile
               440                      445                     450
Gln Ser Gln Leu His Glu Ala Gly Gly Gln Ile Leu Lys Gly Ile
               455                      460                     465
Leu Glu Gly Ala Ser His Ile Leu Pro Ala Phe Arg Val Leu Ser
               470                      475                     480
Ser Leu Leu Ser Ser Cys Ser Asp Ser Val Ala Leu Tyr Ser Phe
               485                      490                     495
Cys Arg Glu Ala Gly Leu Pro Gly Leu Leu Leu Ser Leu Leu Arg
               500                      505                     510
His Ser Gln Glu Ser Asn Ser Leu Gln Gln Gln Ser Trp Tyr Gly
               515                      520                     525
Thr Phe Leu Gln Asp Leu Met Ala Val Ile Gln Ala Tyr Phe Ala
               530                      535                     540
Cys Thr Phe Asn Leu Glu Arg Ser Gln Thr Ser Asp Ser Leu Gln
               545                      550                     555
Val Phe Gln Glu Ala Ala Asn Leu Phe Asp Leu Leu Gly Lys
               560                      565                     570
Leu Leu Ala Gln Pro Asp Asp Ser Glu Gln Thr Leu Arg Arg Asp
               575                      580                     585
Ser Leu Met Cys Phe Thr Val Leu Cys Glu Ala Met Asp Gly Asn
               590                      595                     600
Ser Arg Ala Ile Ser Lys Ala Phe Tyr Ser Ser Leu Leu Thr Thr
               605                      610                     615
Gln Gln Val Val Leu Asp Gly Leu Leu His Gly Leu Thr Val Pro
               620                      625                     630
Gln Leu Pro Val His Thr Pro Gln Gly Ala Pro Gln Val Ser Gln
```

-continued

```
                635                 640                 645
Pro Leu Arg Glu Gln Ser Glu Asp Ile Pro Gly Ala Ile Ser Ser
                650                 655                 660
Ala Leu Ala Ala Ile Cys Thr Ala Pro Val Gly Leu Pro Asp Cys
                665                 670                 675
Trp Asp Ala Lys Glu Gln Val Cys Trp His Leu Ala Asn Gln Leu
                680                 685                 690
Thr Glu Asp Ser Ser Gln Leu Arg Pro Ser Leu Ile Ser Gly Leu
                695                 700                 705
Gln His Pro Ile Leu Cys Leu His Leu Leu Lys Val Leu Tyr Ser
                710                 715                 720
Cys Cys Leu Val Ser Glu Gly Leu Cys Arg Leu Leu Gly Gln Glu
                725                 730                 735
Pro Leu Ala Leu Glu Ser Leu Phe Met Leu Ile Gln Gly Lys Val
                740                 745                 750
Lys Val Val Asp Trp Glu Glu Ser Thr Glu Val Thr Leu Tyr Phe
                755                 760                 765
Leu Ser Leu Leu Val Phe Arg Leu Gln Asn Leu Pro Cys Gly Met
                770                 775                 780
Glu Lys Leu Gly Ser Asp Val Ala Thr Leu Phe Thr His Ser His
                785                 790                 795
Val Val Ser Leu Val Ser Ala Ala Cys Leu Leu Gly Gln Leu
                800                 805                 810
Gly Gln Gln Gly Val Thr Phe Asp Leu Gln Pro Met Glu Trp Met
                815                 820                 825
Ala Ala Ala Thr His Ala Leu Ser Ala Pro Ala Glu Val Arg Leu
                830                 835                 840
Thr Pro Pro Gly Ser Cys Gly Phe Tyr Asp Gly Leu Leu Ile Leu
                845                 850                 855
Leu Leu Gln Leu Leu Thr Glu Gln Gly Lys Ala Ser Leu Ile Arg
                860                 865                 870
Asp Met Ser Ser Ser Glu Met Trp Thr Val Leu Trp His Arg Phe
                875                 880                 885
Ser Met Val Leu Arg Leu Pro Glu Glu Ala Ser Ala Gln Glu Gly
                890                 895                 900
Glu Leu Ser Leu Ser Ser Pro Pro Ser Pro Glu Pro Asp Trp Thr
                905                 910                 915
Leu Ile Ser Pro Gln Gly Met Ala Ala Leu Leu Ser Leu Ala Met
                920                 925                 930
Ala Thr Phe Thr Gln Glu Pro Gln Leu Cys Leu Ser Cys Leu Ser
                935                 940                 945
Gln His Gly Ser Ile Leu Met Ser Ile Leu Lys His Leu Leu Cys
                950                 955                 960
Pro Ser Phe Leu Asn Gln Leu Arg Gln Ala Pro His Gly Ser Glu
                965                 970                 975
Phe Leu Pro Val Val Val Leu Ser Val Cys Gln Leu Leu Cys Phe
                980                 985                 990
Pro Phe Ala Leu Asp Met Asp Ala Asp Leu Leu Ile Val Val Leu
                995                1000                1005
Ala Asp Leu Arg Asp Ser Glu Val Ala Ala His Leu Leu Gln Val
               1010                1015                1020
Cys Cys Tyr His Leu Pro Leu Met Gln Val Glu Leu Pro Ile Ser
               1025                1030                1035
Leu Leu Thr Arg Leu Ala Leu Met Asp Pro Thr Ser Leu Asn Gln
               1040                1045                1050
Phe Val Asn Thr Val Ser Ala Ser Pro Arg Thr Ile Val Ser Phe
               1055                1060                1065
Leu Ser Val Ala Leu Leu Ser Asp Gln Pro Leu Leu Thr Ser Asp
               1070                1075                1080
Leu Leu Ser Leu Leu Ala His Thr Ala Arg Val Leu Ser Pro Ser
               1085                1090                1095
His Leu Ser Phe Ile Gln Glu Leu Leu Ala Gly Ser Asp Glu Ser
               1100                1105                1110
Tyr Arg Pro Leu Arg Ser Leu Leu Gly His Pro Glu Asn Ser Val
               1115                1120                1125
Arg Ala His Thr Tyr Arg Leu Leu Gly His Leu Leu Gln His Ser
               1130                1135                1140
Met Ala Leu Arg Gly Ala Leu Gln Ser Gln Ser Gly Leu Leu Ser
               1145                1150                1155
Leu Leu Leu Gly Leu Gly Asp Lys Asp Pro Val Val Arg Cys
               1160                1165                1170
Ser Ala Ser Phe Ala Val Gly Asn Ala Ala Tyr Gln Ala Gly Pro
               1175                1180                1185
Leu Gly Pro Ala Leu Ala Ala Val Pro Ser Met Thr Gln Leu
               1190                1195                1200
Leu Gly Asp Pro Gln Ala Gly Ile Arg Arg Asn Val Ala Ser Ala
               1205                1210                1215
Leu Gly Asn Leu Gly Pro Glu Gly Leu Gly Glu Glu Leu Leu Gln
               1220                1225                1230
```

```
          Cys Glu Val Pro Gln Arg Leu Leu Glu Met Ala Cys Gly Asp Pro
                      1235                1240                1245
          Gln Pro Asn Val Lys Glu Ala Ala Leu Ile Ala Leu Arg Ser Leu
                      1250                1255                1260
          Gln Gln Glu Pro Gly Ile His Gln Val Leu Val Ser Leu Gly Ala
                      1265                1270                1275
          Ser Glu Lys Leu Ser Leu Leu Ser Leu Gly Asn Gln Ser Leu Pro
                      1280                1285                1290
          His Ser Ser Pro Arg Pro Ala Ser Ala Lys His Cys Arg Lys Leu
                      1295                1300                1305
          Ile His Leu Leu Arg Pro Ala His Ser Met
                      1310                1315
```

<210> SEQ ID NO 26
<211> LENGTH: 4586
<212> TYPE: DNA
<213> ORGANISM: Drosophila virilis

<400> SEQUENCE: 26

```
          tgcagagtct gggccatcgg ctagctctgt agatgtgtaa tagaggcatc   50
          ttcgcgcgca gcatcgattc gcgctccagt tggttgagat gccgaatgtt  100
          ggtgcgcgtc tcaaagatga cgccgacatg gtgcatatac agaaaaaaga  150
          aacccgagcc taatggccgc gtattatcgc tgaggcggcc ggcgattttc  200
          aacaaatgct acttaccaat tagcgcgtgc gataaaatta cgtacaaatt  250
          ggcgtcgcgc atatttctgg cgtttgtgtt gcgtgtatct agttagtggg  300
          ctcgtctatt cattatttac ttttggggcg tctgttttgat caaattagca  350
          gtgtctccta tgatatgcct gcagctttta cccgtaaaca aaattatttg  400
          ccacagctga tttattcgtt gccatgtaga ttaatcagct gtttcgcaat  450
          ttttaaaacc aggtgacttt ttaaaattgt accagctgtg tgtatcgatg  500
          tgcaagcata ctcattacgc catatgctgg tatatttata tcgaatataa  550
          acggttttgg tatttttaata atcttaaaga agaaatagtt atgtgctgtg  600
          tatatgttca tcaagaactg ttcaaaatgt gcgccatact gatgttaatt  650
          ttgttttgct ggtttttttt gggaaaataa attgacgtgt tgatgtctcc  700
          gaatatatcg atacaatagc tatcattcgg acaagatatc gatatgtgga  750
          gtgtgttcgg tattttgcct ttagttttttt gttttttaaat tgcagtcaca  800
          ctgcggctta ttgaatttaa ggcacttcaa agcgcatttt actgtagaaa  850
          gttgagttct atttgcggtg acaatggacc gctacgcggt tagctctctg  900
          gtaggacaag gctcatttgg ctgtgtgtac aaggcccagc ggcgcgatga  950
          tgacaaagtg gtggccatca aagtcatatc aaaggtgagc tcaattgcat 1000
          cccggcttag ctgaataaaa gagtattcta cgaattggcg tgttctttgt 1050
          ttgcagcgtg gtcgttccaa tcgcgagctt aagaacctgc gtcgcgaatg 1100
          tgacattcag gcgcgtctca agcatccgca tgttatagaa atggtggagt 1150
          cgttcgaatc caaattcgat ttgttcgtgg tcaccgagtt cgctctaatg 1200
          gacttgcatc gatatttgtc ctttaatggc gccatgcccg aggagcacgc 1250
          acagcgtgtt gtctgtcatt tggtgtcggc gctctattat ctgcactcga 1300
          atcgcatact gcatcgggat ctaaagccgc aaaatgtgct gttggacaaa 1350
          aacatgcacg ccaagctctg cgacttgggg ctggcacgca acatgacgat 1400
          gggcacacat gtgttgactt ccataaaggg cacgccgctt tatatggcgc 1450
          cggagctgct ggctgagcag ccgtacgatc accaggcaga tatgtggtcg 1500
          ctgggatgca ttgcctatga gagtatggcg ggccagccgc cgttctgcgc 1550
          aacctctata ctgcatctgg tgaagctgat caagcacgag gacgtcaaat 1600
          ggccgagcac gctgagcagc gagtgccgtt cctttttgca gggcttgctc 1650
          gagaaggatc ctagcatgcg catctcatgg acgcagctgc tttgccatcc 1700
          ttttgtcgag ggcaagctat acatagccga ggtacaggca gcacaaactt 1750
          cgccctttat aaatccccag ctggccaagg acaccaaaaa atcacagcaa 1800
          ttgaggtgcg tttataacgt gtactgtagc cagctccact tatcgttcaa 1850
          tttttatgta ggcatgtagg cgcagatttg ggcgatgtct tggcagcgtt 1900
          aaagttgagc gatgtggcca atgaaaactt gagcacatcg cgagatagta 1950
          tcaatgccat tgcgccgagt gacattgagc agctggaaac cgatgttgag 2000
          gataatgtgc atcggcttat agtgccattt gcagatattt cctacagaga 2050
          gttgccatgc ggcactgcag cagctgctcg tcgagctggt gccatgccac 2100
          tgattaattc gcaaacctgc tttgtaagtg gcaactccaa tatgatactc 2150
          aatcatctga acgacaattt tgcaatcgaa gcgcctgctt cgagcgcaac 2200
          caagtccatg aagtcgaagc tgaagctggc tctcaatata aaacagtcgc 2250
          gtagcaagga tttggaaaag cgtaagctga gtcaaaattt ggataacttt 2300
          tcgctgcgcc tgggacagag cattgacata gaagtgcagc gcaaaacaac 2350
          tgagatgctc acgcagcaat cgcaggcaca acagctgcag gataggaaga 2400
          cacagcagct gaagcaatcg atgcattcca ccaacgacga gaaattgagc 2450
          agcgagtgag taatgcatc catatttaaa agtgaagctc tctaaagcta 2500
          tttggtttat aatagcaatt cgccgccttg tctgttgccc ggttgggaca 2550
          gctgcgatga atctcagagc ccgcccattg agaatgacga gtggctggcg 2600
          ttcttgcatc gctccataca ggagctgctg gacggcgaat ttgattcgct 2650
          gaagcagcac aatctagtca gcataattgt ggcgccattg cgaaactcca 2700
          aggccatacc caaggtgctg cagagctgtg cgcagctgct gtcgctgccc 2750
          tttgtgctgg ccgaacagca tttggtagcg gaggccataa aaggagttta 2800
          tattgatgtc aagctggtgc ccaacttaat gtacgcctgc aagctgcttc 2850
          tctcgcagcg ccaccttacc gattcggctg cttcactgcc agccggcacg 2900
```

-continued

```
ggcgtctccc tgagtcgaac cgtacgcagc tgctccgacc tgagtgccga  2950
ggagatgagc accgcctgca gcctgtacga gctggtctgc catctggtcc  3000
atcagcagca gcagttcctc acccagttct gtgacgctgt ggcaatactc  3050
gccgtcaacg acatgttcat aaattttctt acacatggtg agcagctggc  3100
tggacacagt gtgagacgca agcttaacca ttccttgctt tgcagatttt  3150
aaggatagca ggccggtgcg actcgctagc tgcatgctgg cattgttctg  3200
ttgcgttttg cgtgaactac ccgagaacgc cgagctggtg gagaaaattg  3250
tatttgactc gcgcctacag ctggccgtcc tgctgcagag ccgtcatcat  3300
ttgttgcgtc agcgcgcctg tcaaatgctg ttgctattgg cacgctttag  3350
cctgcgcggc gtacagtgca tctggagtgg ggagctgaag agtgcgctcc  3400
aggcgtggcc gatgcagcaa acgtgtcaat cattgcgact ggaagccgcc  3450
caaacgctgg atgagcttag ccagttcagc ttctttgttg ctcaggcaac  3500
tgcttagtct ttattaataa ttgtacttgt atttgtttaa taaatcttaa  3550
tccttgtcta gccgaacaga ccttccaaat tgccttgaaa gtagtcgagc  3600
agctcgtcca gatagctgct aaagccatca aagcccaaaa ggtagctacc  3650
attacagtcc tgctcgtaca tctcgtttag tttcgaaata tccttatccg  3700
acagccgcgc gctggcccag tgaggcatac ggatcctaat gataatagca  3750
tgcattatta ttattttttca caatgtgtta ttcgtttaat acttataaaa  3800
ccttaaattg tatgcatgta tgtatctatc ttatacctaa ttaatgaatg  3850
aaatttatta acttgtctat ggatgtatgt gcatgtatgt atgtatgtat  3900
gtatgcataa aaatgtatgt tcatttataa caaacgcaga caaagataac  3950
gatctgctgc tctacttccc gaatctcata aattcaagta cgccccgcag  4000
atttcacgag tacatcacaa gtgtttttt ttaacaagta atgttggtat  4050
gtatttatgt atatatgtat ttaagtatgt atgtatttat gtatgtatgt  4100
atgtatttat gtatgtatgt atttatgtat gtatgtattt atgtatgtat  4150
gtatttatgt atgtatttat ttatgtatat atgtatttaa gtatgtatgt  4200
atgtatttat gcatttatgt atttatgtat gtatgtataa gagtatgtgt  4250
gtgtgtagat acatgtatgt atgtatgtat gtatgcgtgt atatttattt  4300
atagtaaaca taccaacttt acttccgct gccttgcgaa tttaaaataa  4350
cgtattttta aatgatgccc tactcctcga ttctcaaaca tttaagtaag  4400
ctctacaggt ttttccgatt tgattgtttt gtaaagttgt gttttttttt  4450
ctgctcgatc tcttgtgtat tctctactct ttgtgtgcct ctctttagtt  4500
ttctctcctt ctctcttgct ctcccctgtt ctctctctat ctctctccct  4550
ccctctttcc acctatctca ttctctttct aagctt                 4586
```

<210> SEQ ID NO 27
<211> LENGTH: 1055
<212> TYPE: PRT
<213> ORGANISM: Homo sapiens

<400> SEQUENCE: 27

```
Ile Thr Glu Pro Ala Gly Pro Asp Leu Gly Thr Pro Phe Thr Ser
 1               5                  10                  15
Arg Leu Pro Pro Glu Leu Gln Val Leu Lys Asp Glu Gln Ala His
                20                  25                  30
Arg Leu Ala Pro Lys Gly Asn Gln Ser Arg Ile Leu Thr Gln Ala
                35                  40                  45
Tyr Lys Arg Met Ala Glu Glu Ala Met Gln Lys Lys His Gln Asn
                50                  55                  60
Thr Gly Pro Ala Leu Glu Gln Glu Asp Lys Thr Ser Lys Val Ala
                65                  70                  75
Pro Gly Thr Ala Pro Leu Pro Arg Leu Gly Ala Thr Pro Gln Glu
                80                  85                  90
Ser Ser Leu Leu Ala Gly Ile Leu Ala Ser Glu Leu Lys Ser Ser
                95                 100                 105
Trp Ala Lys Ser Gly Thr Gly Glu Val Pro Ser Ala Pro Arg Glu
               110                 115                 120
Asn Arg Thr Thr Pro Asp Cys Glu Arg Ala Phe Pro Glu Glu Arg
               125                 130                 135
Pro Glu Val Leu Gly Gln Arg Ser Thr Asp Val Asp Leu Glu
               140                 145                 150
Asn Glu Glu Pro Asp Ser Asp Asn Glu Trp Gln His Leu Leu Glu
               155                 160                 165
Thr Thr Glu Pro Val Pro Ile Gln Leu Lys Ala Pro Leu Thr Leu
               170                 175                 180
Leu Cys Asn Pro Asp Phe Cys Gln Arg Ile Gln Ser Gln Leu His
               185                 190                 195
Glu Ala Gly Gly Gln Ile Leu Lys Gly Ile Leu Glu Gly Ala Ser
               200                 205                 210
His Ile Leu Pro Ala Phe Arg Val Leu Ser Ser Leu Leu Ser Ser
               215                 220                 225
Cys Ser Asp Ser Val Ala Leu Tyr Ser Phe Cys Arg Glu Ala Gly
               230                 235                 240
Leu Pro Gly Leu Leu Leu Ser Leu Leu Arg His Ser Gln Glu Ser
               245                 250                 255
Asn Ser Leu Gln Gln Gln Ser Trp Tyr Gly Thr Phe Leu Gln Asp
               260                 265                 270
```

-continued

```
Leu Met Ala Val Ile Gln Ala Tyr Phe Ala Cys Thr Phe Asn Leu
            275                 280                 285
Glu Arg Ser Gln Thr Ser Asp Ser Leu Gln Val Phe Gln Glu Ala
            290                 295                 300
Ala Asn Leu Phe Leu Asp Leu Leu Gly Lys Leu Leu Ala Gln Pro
            305                 310                 315
Asp Asp Ser Glu Gln Thr Leu Arg Arg Asp Ser Leu Met Cys Phe
            320                 325                 330
Thr Val Leu Cys Glu Ala Met Asp Gly Asn Ser Arg Ala Ile Ser
            335                 340                 345
Lys Ala Phe Tyr Ser Ser Leu Leu Thr Thr Gln Gln Val Val Leu
            350                 355                 360
Asp Gly Leu Leu His Gly Leu Thr Val Pro Gln Leu Pro Val His
            365                 370                 375
Thr Pro Gln Gly Ala Pro Gln Val Ser Gln Pro Leu Arg Glu Gln
            380                 385                 390
Ser Glu Asp Ile Pro Gly Ala Ile Ser Ser Ala Leu Ala Ala Ile
            395                 400                 405
Cys Thr Ala Pro Val Gly Leu Pro Asp Cys Trp Asp Ala Lys Glu
            410                 415                 420
Gln Val Cys Trp His Leu Ala Asn Gln Leu Thr Glu Asp Ser Ser
            425                 430                 435
Gln Leu Arg Pro Ser Leu Ile Ser Gly Leu Gln His Pro Ile Leu
            440                 445                 450
Cys Leu His Leu Leu Lys Val Leu Tyr Ser Cys Cys Leu Val Ser
            455                 460                 465
Glu Gly Leu Cys Arg Leu Leu Gly Gln Glu Pro Leu Ala Leu Glu
            470                 475                 480
Ser Leu Phe Met Leu Ile Gln Gly Lys Val Lys Val Val Asp Trp
            485                 490                 495
Glu Glu Ser Thr Glu Val Thr Leu Tyr Phe Leu Ser Leu Leu Val
            500                 505                 510
Phe Arg Leu Gln Asn Leu Pro Cys Gly Met Glu Lys Leu Gly Ser
            515                 520                 525
Asp Val Ala Thr Leu Phe Thr His Ser His Val Val Ser Leu Val
            530                 535                 540
Ser Ala Ala Ala Cys Leu Leu Gly Gln Leu Gly Gln Gln Gly Val
            545                 550                 555
Thr Phe Asp Leu Gln Pro Met Glu Trp Met Ala Ala Thr His
            560                 565                 570
Ala Leu Ser Ala Pro Ala Glu Val Arg Leu Thr Pro Pro Gly Ser
            575                 580                 585
Cys Gly Phe Tyr Asp Gly Leu Leu Ile Leu Leu Leu Gln Leu Leu
            590                 595                 600
Thr Glu Gln Gly Lys Ala Ser Leu Ile Arg Asp Met Ser Ser Ser
            605                 610                 615
Glu Met Trp Thr Val Leu Trp His Arg Phe Ser Met Val Leu Arg
            620                 625                 630
Leu Pro Glu Glu Ala Ser Ala Gln Glu Gly Glu Leu Ser Leu Ser
            635                 640                 645
Ser Pro Pro Ser Pro Glu Pro Asp Trp Thr Leu Ile Ser Pro Gln
            650                 655                 660
Gly Met Ala Ala Leu Leu Ser Leu Ala Met Ala Thr Phe Thr Gln
            665                 670                 675
Glu Pro Gln Leu Cys Leu Ser Cys Leu Ser Gln His Gly Ser Ile
            680                 685                 690
Leu Met Ser Ile Leu Lys His Leu Leu Cys Pro Ser Phe Leu Asn
            695                 700                 705
Gln Leu Arg Gln Ala Pro His Gly Ser Glu Phe Leu Pro Val Val
            710                 715                 720
Val Leu Ser Val Cys Gln Leu Leu Cys Phe Pro Phe Ala Leu Asp
            725                 730                 735
Met Asp Ala Asp Leu Leu Ile Val Val Leu Ala Asp Leu Arg Asp
            740                 745                 750
Ser Glu Val Ala Ala His Leu Leu Gln Val Cys Cys Tyr His Leu
            755                 760                 765
Pro Leu Met Gln Val Glu Leu Pro Ile Ser Leu Leu Thr Arg Leu
            770                 775                 780
Ala Leu Met Asp Pro Thr Ser Leu Asn Gln Phe Val Asn Thr Val
            785                 790                 795
Ser Ala Ser Pro Arg Thr Ile Val Ser Phe Leu Ser Val Ala Leu
            800                 805                 810
Leu Ser Asp Gln Pro Leu Leu Thr Ser Asp Leu Leu Ser Leu Leu
            815                 820                 825
Ala His Thr Ala Arg Val Leu Ser Pro Ser His Leu Ser Phe Ile
            830                 835                 840
Gln Glu Leu Leu Ala Gly Ser Asp Glu Ser Tyr Arg Pro Leu Arg
            845                 850                 855
Ser Leu Leu Gly His Pro Glu Asn Ser Val Arg Ala His Thr Tyr
```

-continued

```
                  860                    865                    870
     Arg Leu Leu Gly His Leu Leu Gln His Ser Met Ala Leu Arg Gly
                  875                    880                    885
     Ala Leu Gln Ser Gln Ser Gly Leu Leu Ser Leu Leu Leu Leu Gly
                  890                    895                    900
     Leu Gly Asp Lys Asp Pro Val Val Arg Cys Ser Ala Ser Phe Ala
                  905                    910                    915
     Val Gly Asn Ala Ala Tyr Gln Ala Gly Pro Leu Gly Pro Ala Leu
                  920                    925                    930
     Ala Ala Ala Val Pro Ser Met Thr Gln Leu Leu Gly Asp Pro Gln
                  935                    940                    945
     Ala Gly Ile Arg Arg Asn Val Ala Ser Ala Leu Gly Asn Leu Gly
                  950                    955                    960
     Pro Glu Gly Leu Gly Glu Glu Leu Leu Gln Cys Glu Val Pro Gln
                  965                    970                    975
     Arg Leu Leu Glu Met Ala Cys Gly Asp Pro Gln Pro Asn Val Lys
                  980                    985                    990
     Glu Ala Ala Leu Ile Ala Leu Arg Ser Leu Gln Gln Glu Pro Gly
                  995                   1000                   1005
     Ile His Gln Val Leu Val Ser Leu Gly Ala Ser Glu Lys Leu Ser
                 1010                   1015                   1020
     Leu Leu Ser Leu Gly Asn Gln Ser Leu Pro His Ser Ser Pro Arg
                 1025                   1030                   1035
     Pro Ala Ser Ala Lys His Cys Arg Lys Leu Ile His Leu Leu Arg
                 1040                   1045                   1050
     Pro Ala His Ser Met
                 1055
```